United States Patent
Ledeboer et al.

(10) Patent No.: US 11,504,389 B2
(45) Date of Patent: Nov. 22, 2022

(54) TAU MODULATORS AND METHODS AND COMPOSITIONS FOR DELIVERY THEREOF

(71) Applicants: Sangamo Therapeutics, Inc., Richmond, CA (US); The General Hospital Corporation, Boston, MA (US)

(72) Inventors: Annemarie Ledeboer, Richmond, CA (US); Bryan Zeitler, Richmond, CA (US); H. Steve Zhang, Richmond, CA (US); Sarah DeVos, Boston, MA (US); Bradley T. Hyman, Boston, MA (US); Susanne Wegmann, Boston, MA (US)

(73) Assignees: Sangamo Therapeutics, Inc., Brisbane, CA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/828,931

(22) Filed: Dec. 1, 2017

(65) Prior Publication Data
US 2018/0153921 A1    Jun. 7, 2018

Related U.S. Application Data

(60) Provisional application No. 62/428,871, filed on Dec. 1, 2016, provisional application No. 62/450,895, filed on Jan. 26, 2017, provisional application No. 62/466,198, filed on Mar. 2, 2017, provisional application No. 62/500,807, filed on May 3, 2017, provisional application No. 62/584,342, filed on Nov. 10, 2017.

(51) Int. Cl.
| | |
|---|---|
| C07H 21/04 | (2006.01) |
| A61K 38/00 | (2006.01) |
| A61K 31/70 | (2006.01) |
| A61K 48/00 | (2006.01) |
| A61K 31/7105 | (2006.01) |
| C12N 15/86 | (2006.01) |
| A61P 25/28 | (2006.01) |
| A61K 38/17 | (2006.01) |
| C07K 14/47 | (2006.01) |
| C12N 15/864 | (2006.01) |
| A01K 67/00 | (2006.01) |

(52) U.S. Cl.
CPC ...... *A61K 31/7105* (2013.01); *A61K 38/1709* (2013.01); *A61P 25/28* (2018.01); *C07K 14/4702* (2013.01); *C07K 14/4711* (2013.01); *C12N 15/86* (2013.01); *C12N 15/8645* (2013.01); *C12N 2750/14143* (2013.01)

(58) Field of Classification Search
CPC ........... A61K 31/7105; C12N 15/86; C12N 15/8645; C12N 2750/14143; A61P 25/28; C07K 14/4702; C07K 14/4711
See application file for complete search history.

(56) References Cited

U.S. PATENT DOCUMENTS

| | | | |
|---|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,789,538 A | 8/1998 | Rebar et al. |
| 5,925,523 A | 7/1999 | Dove et al. |
| 6,007,988 A | 12/1999 | Choo et al. |
| 6,008,336 A | 12/1999 | Hanson et al. |
| 6,013,453 A | 1/2000 | Choo et al. |
| 6,140,081 A | 10/2000 | Barbas |
| 6,200,759 B1 | 3/2001 | Dove et al. |
| 6,309,634 B1 | 10/2001 | Bankiewicz et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,746,838 B1 | 6/2004 | Choo et al. |
| 6,824,978 B1 | 11/2004 | Cox, III et al. |
| 6,866,997 B1 | 3/2005 | Choo et al. |
| 6,903,185 B2 | 6/2005 | Kim et al. |
| 6,933,113 B2 | 8/2005 | Case et al. |
| 6,953,575 B2 | 10/2005 | Bankiewicz et al. |
| 6,979,539 B2 | 12/2005 | Cox, III et al. |
| 7,013,219 B2 | 3/2006 | Case et al. |
| 7,074,596 B2 | 7/2006 | Daryznkiewicz et al. |
| 7,153,949 B2 | 12/2006 | Kim et al. |
| 7,163,824 B2 | 1/2007 | Cox, III et al. |
| 7,182,944 B2 | 2/2007 | Bankiewicz |
| 7,198,951 B2 | 4/2007 | Gao et al. |

(Continued)

FOREIGN PATENT DOCUMENTS

| | | |
|---|---|---|
| EP | 3 080 611 A1 | 10/2016 |
| RU | 2582916 | 4/2016 |

(Continued)

OTHER PUBLICATIONS

Ando, et al., "Stabilization of Microtubule-Unbound Tau Via Tau Phosphorylation at SER262/356 by PAR-l/Mark Contributes To Augmentation of Ad-Related Phosphorylation and AB42-Induced Tau Toxicity," *PLoS Genet* 12(3):1-26, e1005917 (2016).

(Continued)

*Primary Examiner* — Quang Nguyen
(74) *Attorney, Agent, or Firm* — Steptoe & Johnson LLP; Z. Ying Li; Benjamin M. Schuman

(57) ABSTRACT

The present disclosure is in the field of diagnostics and therapeutics for Alzheimer's Disease.

31 Claims, 34 Drawing Sheets
Specification includes a Sequence Listing.

(56) References Cited

U.S. PATENT DOCUMENTS

| | | | |
|---|---|---|---|
| 7,241,573 B2 | 7/2007 | Choo et al. | |
| 7,241,574 B2 | 7/2007 | Choo et al. | |
| 7,837,668 B2 | 11/2010 | Gasmi et al. | |
| 7,888,121 B2 | 2/2011 | Umov et al. | |
| 7,914,796 B2 | 3/2011 | Miller et al. | |
| 8,034,598 B2 | 10/2011 | Miller | |
| 8,092,429 B2 | 1/2012 | Gasmi et al. | |
| 8,153,773 B2 | 4/2012 | Jemielity et al. | |
| 8,309,355 B2 | 11/2012 | Bankiewicz et al. | |
| 8,337,458 B2 | 12/2012 | Bankiewicz et al. | |
| 8,409,861 B2 | 4/2013 | Guschin et al. | |
| 8,586,526 B2 | 11/2013 | Gregory et al. | |
| 8,597,912 B2 | 12/2013 | Collingwood et al. | |
| 8,623,618 B2 | 1/2014 | Doyon et al. | |
| 8,647,631 B2 | 2/2014 | Pfeifer et al. | |
| 8,703,489 B2 | 4/2014 | Wang | |
| 8,956,828 B2 | 2/2015 | Bonini et al. | |
| 9,050,299 B2 | 6/2015 | Bankiewicz | |
| 9,089,667 B2 | 7/2015 | Bankiewicz | |
| 9,200,266 B2 | 12/2015 | Wang | |
| 9,458,205 B2 | 10/2016 | Gregory et al. | |
| 9,585,971 B2 | 3/2017 | Deverman et al. | |
| 9,885,039 B2* | 2/2018 | Huang | A61K 31/7088 |
| 10,563,184 B2* | 2/2020 | Miller | A61K 35/28 |
| 10,793,856 B2 | 10/2020 | Kordasiewicz et al. | |
| 2003/0021776 A1 | 1/2003 | Rebar et al. | |
| 2006/0239966 A1 | 10/2006 | Tornøe et al. | |
| 2009/0068164 A1 | 3/2009 | Segal et al. | |
| 2009/0111119 A1 | 4/2009 | Doyon et al. | |
| 2011/0016539 A1 | 1/2011 | Weinstein et al. | |
| 2011/0082093 A1 | 4/2011 | Gregory et al. | |
| 2011/0301073 A1 | 12/2011 | Gregory et al. | |
| 2012/0195936 A1 | 8/2012 | Rudolph et al. | |
| 2013/0130347 A1 | 5/2013 | Delisa et al. | |
| 2013/0196373 A1 | 8/2013 | Gregory et al. | |
| 2013/0253040 A1 | 9/2013 | Miller et al. | |
| 2014/0357530 A1 | 12/2014 | Zhang et al. | |
| 2015/0056177 A1* | 2/2015 | Liu | C12N 9/22 |
| | | | 424/94.3 |
| 2015/0056705 A1 | 2/2015 | Conway et al. | |
| 2015/0267205 A1 | 9/2015 | Froelich et al. | |
| 2015/0335708 A1 | 11/2015 | Froelich et al. | |
| 2015/0353917 A1 | 12/2015 | Miller | |
| 2016/0201089 A1 | 7/2016 | Gersbach et al. | |
| 2016/0333063 A1* | 11/2016 | Hyman | C07K 16/18 |
| 2017/0035860 A1* | 2/2017 | Flynn | A61K 38/465 |
| 2017/0119906 A1 | 5/2017 | Riley | |
| 2018/0087072 A1 | 3/2018 | Miller et al. | |
| 2018/0142215 A1 | 5/2018 | Eguchi et al. | |
| 2020/0101133 A1 | 4/2020 | Riley et al. | |
| 2020/0109406 A1 | 4/2020 | Miller et al. | |

FOREIGN PATENT DOCUMENTS

| | | | | |
|---|---|---|---|---|
| WO | WO 95/19431 A1 | 7/1995 | | |
| WO | WO 96/06166 A1 | 2/1996 | | |
| WO | WO 98/53057 A1 | 11/1998 | | |
| WO | WO 98/53058 A1 | 11/1998 | | |
| WO | WO 98/53059 A1 | 11/1998 | | |
| WO | WO 98/53060 A1 | 11/1998 | | |
| WO | WO 98/54311 A1 | 12/1998 | | |
| WO | WO 00/27878 A1 | 5/2000 | | |
| WO | WO 01/60970 A2 | 8/2001 | | |
| WO | WO 01/88197 A2 | 11/2001 | | |
| WO | WO 02/016536 A1 | 2/2002 | | |
| WO | WO 02/099084 A2 | 12/2002 | | |
| WO | WO 03/016496 A2 | 2/2003 | | |
| WO | WO 2010/079430 A1 | 7/2010 | | |
| WO | WO-2010076939 A1 * | 7/2010 | | C12N 9/22 |
| WO | 2011/139349 | 11/2011 | | |
| WO | 2013/130824 | 9/2013 | | |
| WO | 2015153760 A2 | 10/2015 | | |
| WO | 2017/011556 | 1/2017 | | |
| WO | 2017/197141 A2 | 11/2017 | | |
| WO | 2018/039471 A2 | 3/2018 | | |
| WO | 2018/049009 A2 | 3/2018 | | |
| WO | 2021/151012 | 7/2021 | | |

OTHER PUBLICATIONS

Bannister, et al., "Regulation of Chromatin by Histone Modifications," Cell Research 21(3):381-395 (2011).
Benussi, et al., "Phenotypic Heterogeneity of Monogenic Frontotemporal Dementia," Front Ag Neuro 7(171):1-19 (2015).
Beurdeley, et al., "Compact Designer Talens for Efficient Genome Engineering," Nat Commun 4(1762):1-8. doi:10.1038/ncomms2782 (2013).
Boch, et al., "Breaking the Code of DNA Binding Specificity of Tal-Type III Effectors," Science 326:1509-1512 (2009).
Bodea, et al., "Tau Physiology and Pathomechanisms in Frontotemporal Lobar Degeneration," J of Neurochem 138(Suppl 1):71-94 (2016).
Boissel, et al., "MEGATALS: A Rare-Cleaving Nuclease Architecture for Therapeutic Genome Engineering," Nucleic Acids Research 42(4):2591-2601. doi:10.1093/nar/gkt1224 (2013).
Bonas, et al., "Genetic and Structural Characterization of the Avirulence Gene AVRBS3 From Xanthomonas Campestris Pv. Vesicatoria," Mol Gen Genet 218:127-136 (1989).
Brouns, et al., "Small CRISPR RNAs Guide Antiviral Defense in Prokaryotes," Science 321:960-964 (2008).
Cong, et al., "Multiplex Genome Engineering Using CRISPR/CAS Systems," Science 339(6121): 819-823 doi: 10.1126/science. 1231143 (2013).
De Calignon, et al., "Propagation of Tau Pathology in a Model of Early Alzheimer's Disease," Neuron 73:685-697 (2012).
DeVos, et al., "Antisense Reduction of Tau in Adult Mice Protects Against Seizures," JJournal of NeuroScience 33(31):12887-12897 (2013).
Esvelt, et al., "Orthogonal CAS9 Proteins for RNA-Guided Gene Regulation and Editing," Nature Methods 10(11):1116 (2013).
Fonfara, et al., "Phylogeny of CAS9 Determines Functional Exchangeability of Dual-RNA and CAS9 Among Orthologous Type II CRISPR-CAs Systems," Nucleic Acids Research 42(4):2377-2590 (2013).
Fu, et al., "Improving CRISPR-CAS Nuclease Specificity Using Truncated Guide RNAs," Nature Biotechnol 32(3):279-284 (2014).
Gheyara, et al., "Tau Reduction Prevents Disease in a Mouse Model of Dravet Syndrome," Ann Neurol 76(3):443-456 (2014).
Godde, et al., "The Repetitive Dna Elements Called Crisprs and Their Associated Genes: Evidence of Horizontal Transfer Among Prokaryotes," J Mol Evol 62:718-729 (2006).
Gurda, et al., "Evaluation of AAV-mediated Gene Therapy for Central Nervous System Disease in Canine Mucopolysaccharidosis VII," Molecular Therapy 24(2):206-216 (2016).
Haft, et al., "A Guild of 45 Crispr-Associated (Cas) Protein Families and Multiple Crispr/Cas Subtypes Exist in Prokaryotic Genomes," PLoS Computational Biology 1(6)e60:474-483 (2005).
Hale, et al., "Prokaryotic Silencing (PSI)RNAs in Pyrococcus Furiosus," RNA 14:2572-2579 (2008).
Hardy, et al., "The Amyloid Hypothesis of Alzheimer'S Disease: Progress and Problems on the Road to Therapeutics," Science 297:353-356 (2002).
Heuer, et al., "Repeat Domain Diversity of AVRBS3-LIKE Genes in Ralstonia Solanacearum Strains and Association With Host Preferences in the Field," Applied and Environmental Microbiology 73(13):4379-4384 (2007).
Hilton, et al., "Epigenome Editing by a CRISPR/CAS9-Based Acetyltransferase Activates Genes From Promoters and Enhancers," Nat Biotechnol 33(5):510-517 (2015).
Hsiao, et al., "Upregulation of Haploinsufficient Gene Expression in the Brain by Targeting a Long Non-Coding RNA Improves Seizure Phenotype in a Model of Dravet Syndrome," EBioMedicine 9:257-277 (2016).
Hsu, et al., "DNA Targeting Specificity of RNA-Guided CAS9 Nucleases," Nat Biotechnol 31(9):827-832, doi:10.1038/nbt.2647 (2013).
Hwang, et al., "Efficient in Vivo Genome Editing Using RNA-Guided Nucleases," Nat Biotechnol 31(3):227-229 (2013).

(56) References Cited

OTHER PUBLICATIONS

Hyman, "Tau Propagation, Different Tau Phenotypes, and Prion-Like Properties of Tau," *Neuron* 82:1189-1190 (2014).
Jackson, et al., "Initial Gene Vector Dosing for Studying Symptomatology of Amyotrophic Lateral Sclerosis in Non-Human Primates," *J. Med Primatol* 44(2):66-75 (2015).
Jansen, et al., "Identification of Genes That are Associated With DNA Repeats in Prokaryotes," *Molecular Microbiology* 43(6):1565-1575 (2002).
Jinek, et al., "A Programmable Dual-RNA-Guided DNA Endonuclease in Adaptive Bacterial Immunity," *Science* 337:816-821 (2012).
Johnston, et al., "Symptomatic Models of Parkinson's Disease and L-Dopa-Induced Dyskinesia in Non-Human Primates," *Curr Top Behav Neurosci* 22:221-235 (2015).
Kabadi, et al., "Engineering Synthetic Tale and CRISPR/CAS9 Transcription Factors for Regulating Gene Expression," *Methods* 69(2):188-197 (2014).
Kadiyala, et al., "Spatiotemporal Differences in the C-Fos Pathway Between C57BL/6J and DBA/2J Mice Following Flurothyl-Induced Seizures: A Dissociation of Hippocampal FOS From Seizure Activity," *Epilepsy Res* 109:183-196 (2015).
Kay, et al., "A Bacterial Effector Acts as a Plant Transcription Factor and Induces a Cell Size Regulator," *Science* 318:648-651 (2007).
Kimura, et al., "Physiological and Pathological Phosphorylation of Tau by CDK5," *Frontiers in Molecular Neuroscience* 7(65): 1-10. doi: 10.3389/fnmol.2014.00065 (2014).
Kormann, et al., "Expression of Therapeutic Proteins After Delivery of Chemically Modified MRNA in Mice," *Nature Biotechnology* 29(2):154-157 (2011).
Kouzarides, "Chromatin Modifications and Their Function," *Cell* 128(4):693-705 (2007).
Laganiere, et al., "An Engineered Zinc Finger Protein Activator of the Endogenous Glial Cell Line-Derived Neurotrophic Factor Gene Provides Functional Neuroprotection in a Rat Model of Parkinson's Disease," *Journal of Neuroscience* 30(49):16469-16474 (2010).
Li, et al., "Application of APP/OS1 Transgenic Mouse Model for Alzheimer'S Disease," *J Alzheimers Dis Parkin* 5(3):4 pgs., doi: 10.4172/2161-0460.1000201 (2015).
Lillestøl, et al., "A Putative Viral Defence Mechanism in Archaeal Cells," *Archaea* 2:59-72 (2006).
Liu, et al., "Regulation of an Endogenous Locus Using a Panel of Designed Zinc Finger Proteins Targeted to Accessible Chromatin Regions," *Journal of Biological Chemistry* 276(14):11323-11334 (2001).
Liu, et al., "Vectored Intracerebral Immunization With the Anti-Tau Monoclonal Antibody PHF1 Markedly Reduces Tau Pathology in Mutant Tau Transgenic Mice," *Journal Neuroscience* 36(49):12425-12435 (2016).
Makarova, et al., "A DNA Repair System Specific for Thermophilic Archaea and Bacteria Predicted by Genomic Context Anlysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic Rnai, and Hypothetical Mechanisms of Action," *Biology Direct* 1(7):1-26 (2006).
Moscou, et al., "A Simple Cipher Governs DNA Recognition by Tal Effectors," *Science* 326:1501 (2009).
Noble, et al., "The Importance of Tau Phosphorylation for Neurodegenerative Diseases," *Frontiers in Neurology* 4(83):1-11. doi: 10.3389/fneur.2013.00083 (2013).
Olsson, et al., "Characterization of Intermediate Steps in Amyloid Beta (AP) Production Under Near-Native Conditions," *Journal of Biological Chemistry* 289(3):1540-1550 (2014).
Ong, et al., "Enhancer Function: New Insights Into the Regulation of Tissue-Specific Gene Expression," *Nat Rev Genetics* 12(4):283-293 (2011).

Park, et al., "Quantitative Expression Analysis of App Pathway and Tau Phosphorylation-Related Genes in the ICV STZ-Induced Non-Human Primate Model of Sporadic Alzheimer's Disease," *Int J Mol Sci* 16(2):2386-2402 (2015).
Polydoro, et al., "Reversal of Neurofibrillary Tangles and Tau-Associated Phenotype in the RTGTAUEC Model of Early Alzheimer'S Disease," *Journal of Neuroscience* 33(33):13300-13311 (2013).
Pooler, et al., "Amyloid Accelerates Tau Propagation and Toxicity in a Model of Early Alzheimer'S Disease," *Acta Neuropathologica Communications* 3(14):1, doi:10.1186/s40478-015-0199-x (2015).
Ramalingam, et al., "Generation and Genetic Engineering of Human Induced Pluripotent Stem Cells Using Designed Zinc Finger Nucleases," *Stem Cells and Development* 22(4):595-610 (2013).
Sander, et al., "CRISPR-CAS Systems for Genome Editing, Regulation and Targeting," *Nature Biotechnol* 32(4):347-355 (2014).
Scholz, et al., "Genetics Underlying Atypical Parkinsonism and Related Neurodegenerative Disorders," *Int J. Mol Sci* 16(10):24629-24655 (2015).
Schornack, et al., "Gene-For-Gene-Mediated Recognition of Nuclear-Targeted AVRBS3-Like Bacterial Effector Proteins," *Journal of Plant Physiology* 163(3):256-272 (2006).
Schutt, et al., "Dogs With Cognitive Dysfunction as a Spontaneous Model for Early Alzheimer's Disease: A Translational Study of Neuropathological and Inflammatory Markers," *J Alzheimer's Dis* 52(2):433-449 (2016).
Sheng, et al., "Structure-Based Cleavage Mechanism of Thermus Thermophilus Argonaute DNA Guide Strand-Mediated DNA Target Cleavage," *Proc. Natl. Acad. Sci. U.S.A.* 111(2):652-657 (2014).
Sorek, et al., "CRISPR—A Widespread System That Provides Acquired Resistance Against Phages in Bacteria and Archaea," *Nature Reviews Microbiology* 6:181-186 (2008).
Sorrentino, et al., "The Dark Sides of Amyloid in Alzheimer'S Disease Pathogenesis," *FEBS Lett* 588:641-652 (2014).
Spires-Jones, et al., "The Intersection of Amyloid Beta and Tau at Synapses in Alzheimer's Disease," *Neuron* 82(4):756-771 (2014).
Swarts, et al., "DNA-Guided Dna Interference by a Prokaryotic Argonaute," *Nature* 507(7491):258-261 (2014).
Takeda, et al., "Neuronal Uptake and Propagation of a Rare Phosphorylated High-Molecular-Weight Tau Derived From Alzheimer's Disease Brain," *Nature Communications* 6:8490, doi:10.1038/ncomms9490 (2015).
Tang, et al., "Identification of 86 Candidates for Small Non-Messenger RNAs From the Archaeon Archaeoglobus Fulgidus," *Proc. Natl. Acad. Sci.* 99(11):7536-7541 (2002).
Tang, et al., "Identification of Novel Non-Coding RNAs as Potential Antisense Regulators in the Archaeon Sulfolobus Solfataricus," *Molecular Microbiology* 55(2):469-481 (2005).
Van Dijk, et al., "Integrative Neurobiology of Metabolic Diseases, Neuroinflammation, and Neurodegeneration," *Frontiers in Neuroscience* 9(173): 1-19 (2015).
Varatharajah, et al., "Seizure Forecasting and the Preictal State in Canine Epilepsy," *Int J Neural Syst* 27(1):1650046 (2017).
Wang, et al., "RBFOX3/NEUN is Required for Hippocampal Circuit Balance and Function," *Sci Reports* 5(17383):1-16. doi 10.1038/sprel7383 (2015).
Webster, et al., "Using Mice to Model Alzheimer's Dementia: An Overview of the Clinical Disease and the Preclinical Behavioral Changes in 10 Mouse Models," *Front Genet* 5(99): 1-23, doi:10.3389f/gene.2014.00088 (2014).
Wegmann, et al., "Removing Endogenous Tau Does Not Prevent Tau Propagation yet Reduces Its Neurotoxicity," *EMBO J.* 34(24):3028-3041 (2015).
Wu, et al., "Genome-Wide Binding of the CRISPR Endonuclease CAS9 in Mammalian Cells," *Nature Biotechnology* doi: 10.1038/nbt2889 (2014).
Yang, et al., "Towards a Transgenic Model of Huntington's Disease in a Non-Human Primate," *Nature* 453(7197):921-924 (2008).
Zhang, et al., "A Designed Zinc-Finger Transcriptional Repressor of Phospholamban Improves Function of the Failing Heart," *Mol Ther* 20(8):1508-1515 (2012).

(56) References Cited

OTHER PUBLICATIONS

Gersbach, et al., "Synthetic Zinc Finger Proteins: The Advent of Targeted Gene Regulation and Genome Modification Technologies," Accounts of Chemical Research, vol. 47, No. 8, pp. 2309-2318 (2014).

Heman-Ackah, et al., "Precision Modulation of Neurodegenerative Disease-Related Gene Expression in Human IPSC-Derived Neurons," Scientific Reports, vol. 6, No. 28420, pp. 1-12 (2016).

Nimsanor, et al., "Generation of an Isogenic, Gene-Corrected IPSC Line From a Pre-Symptomatic 28-Year-Old Woman With the R406W Mutation in the Microtubule Associated Protein Tau (MAPT) Gene," Stem Cell Research, vol. 17, No. 3, pp. 600-602 (2016).

Burstein et al., "New CRISPR-Cas Systems from Uncultivated Microbes," Nature (2017) 542(7640):237-241.

Carstens et al., "Perineuronal Nets Suppress Plasticity of Excitatory Synapses on Ca2 Pyramidal Neurons," J Neurosci. (2016) 36(23):6312-6320.

Cebrian-Serrano et al., "CRISPR-Cas Orthologues and Variants: Optimizing the Repertoire, Specificity and Delivery of Genome Engineering Tools," Mamm Genome (2017) 28(7):247-261.

Conrad et al., "A Polymorphic Gene Nested Within an Intron of The Tau Gene: Implications for Alzheimer's Disease," Proc Natl Acad Sci USA (2002) 99(11):7751-7756.

Fagerlund et al., "The Cpf1 CRISPR-Cas protein expands genome-editing tools," Genome Biology (2015) 16:251.

Ferraro et al., "Mapping Murine Loci for Seizure Response to Kainic Acid," Mamm Genome (1997) 8(3):200-208.

Kleinstiver et al., "High-Fidelity CRISPR-Cas9 Variants with Undetectable Genome-Wide Off-Targets," Nature (2016) 529(7587):490-495.

Ma et al., "Rational Design of Mini-Cas9 for Transcriptional Activation," ACS Synth Biol. (2018) 7(4):978-985.

Myers et al., "Effects of Acute and Chronic Paleocerebellar Stimulation on Experimental Models of Epilepsy in the Cat: Studies with Enflurane, Pentylenetetrazol, Penicillin, and Chloralose," Epilepsia (1975) 16(2):257-67.

Remacle et al., "New Mode of DNA Binding of Multi-Zinc Finger Transcription Factors: DeltaEF1 Family Members Bind with Two Hands to Two Target Sites," EMBO Journal (1999) 18(18):5073-5084.

Troung et al., "Development of an Intein-Mediated Split-Cas9 System for Gene Therapy," Nucl Acid Res. (2015) 43(13):6450-8.

Zeitler et al., "Allele-Selective Transcriptional Repression of Mutant HTT for the Treatment of Huntington's Disease," Nature Medicine (2019) 25(7):1131-1142.

Zetsche et al., "A Split-Cas9 Architecture for Inducible Genome Editing and Transcription Modulation," Nat Biotechnol. (2015) 33(2):139-142.

Asokan et al., "The AAV Vector Toolkit: Poised at the Clinical Crossroads," (2012) Molecular Therapy 20(4) 699-708.

Zeitler, et al., "Sustained Tau Reduction via Zinc Finger Protein Transcription Factors as a Potential Next-Generation Therapy for Alzheimer's Disease and Other Tauopathies," ASGCT 20th Annual Meeting (2017) XP055800066.

Caillet-Boudin et al., "Regulation of Human MAPT Gene Expression," Molecular Neurodegeneration (2015) 10[1]:1-14.

Golebiowski, et al., "Direct Intracranial Injection of AAVrh8 Encoding Monkey β-N-Acetylhexosaminidase Causes Neurotoxicity in the Primate Brain," Human Gene Therapy (2017) 28(6): 510-22.

Perez, et al., "Management of Neuroinflammatory Responses to AAV-Mediated Gene Therapies for Neurodegenerative Diseases," Brain Sci. (2020) 10(2): 119.

Wegmann, et al. "Persistent repression of tau in the brain using engineered zinc finger protein transcription factors," Sci. Adv. (2021) 7(eabe1611):1-19.

Hocquemiller, et al., "Adeno-Associated Virus-Based Gene Therapy for CNS Diseases," Human Gene Therapy (2016) 27(7):478-97.

Yamamoto, et al., "Genome Editing with Programmable Site-Specific Nucleases," Uirusu (Virus) (2014) 64(1):75-82.

\* cited by examiner

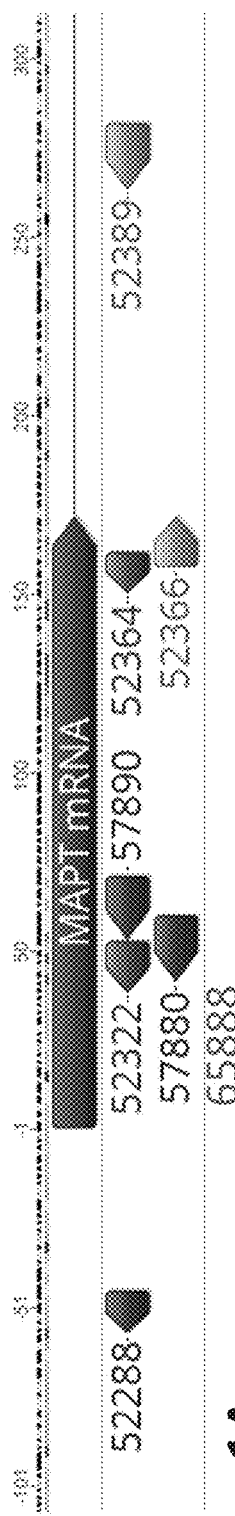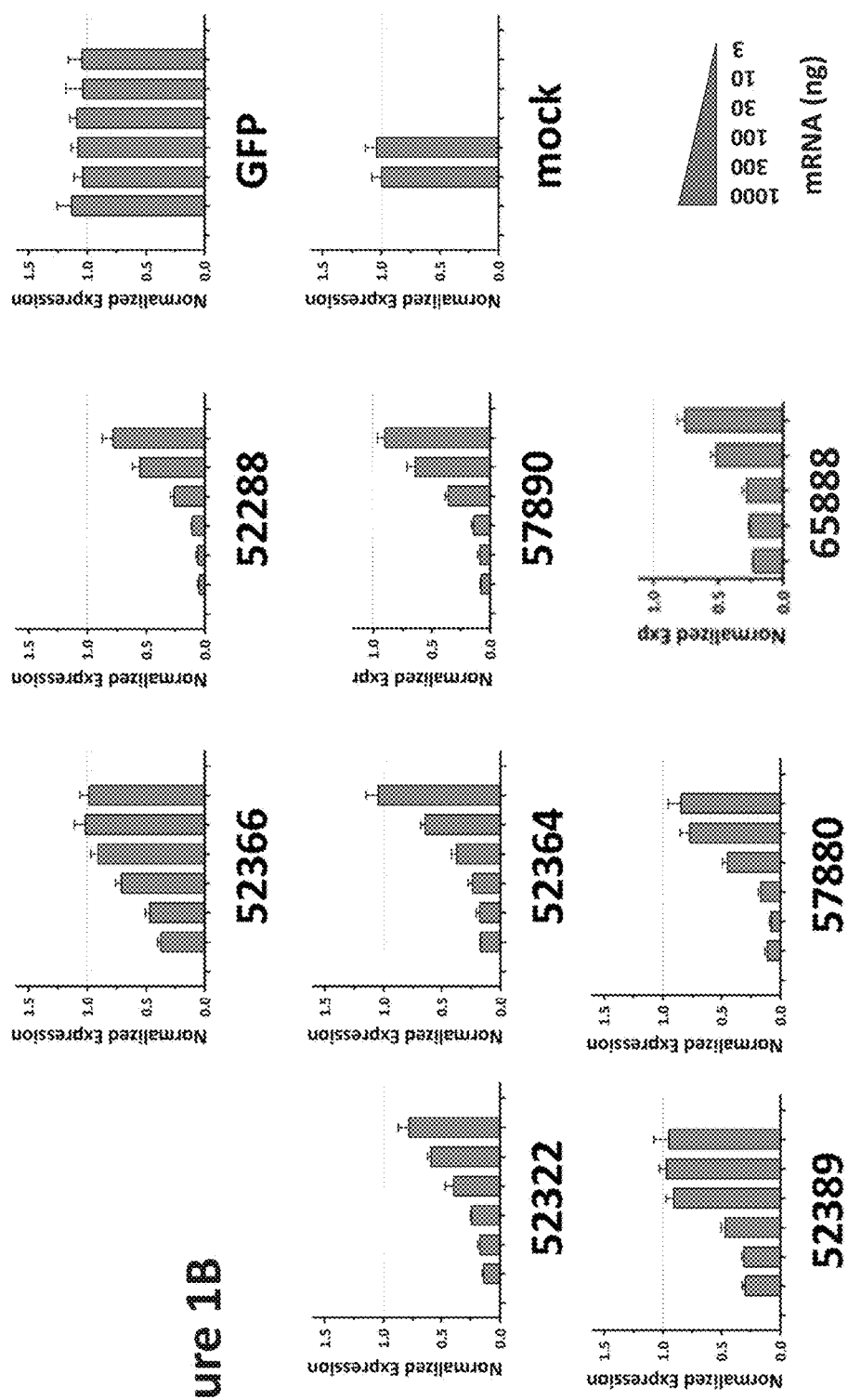
Figure 1A
Figure 1B

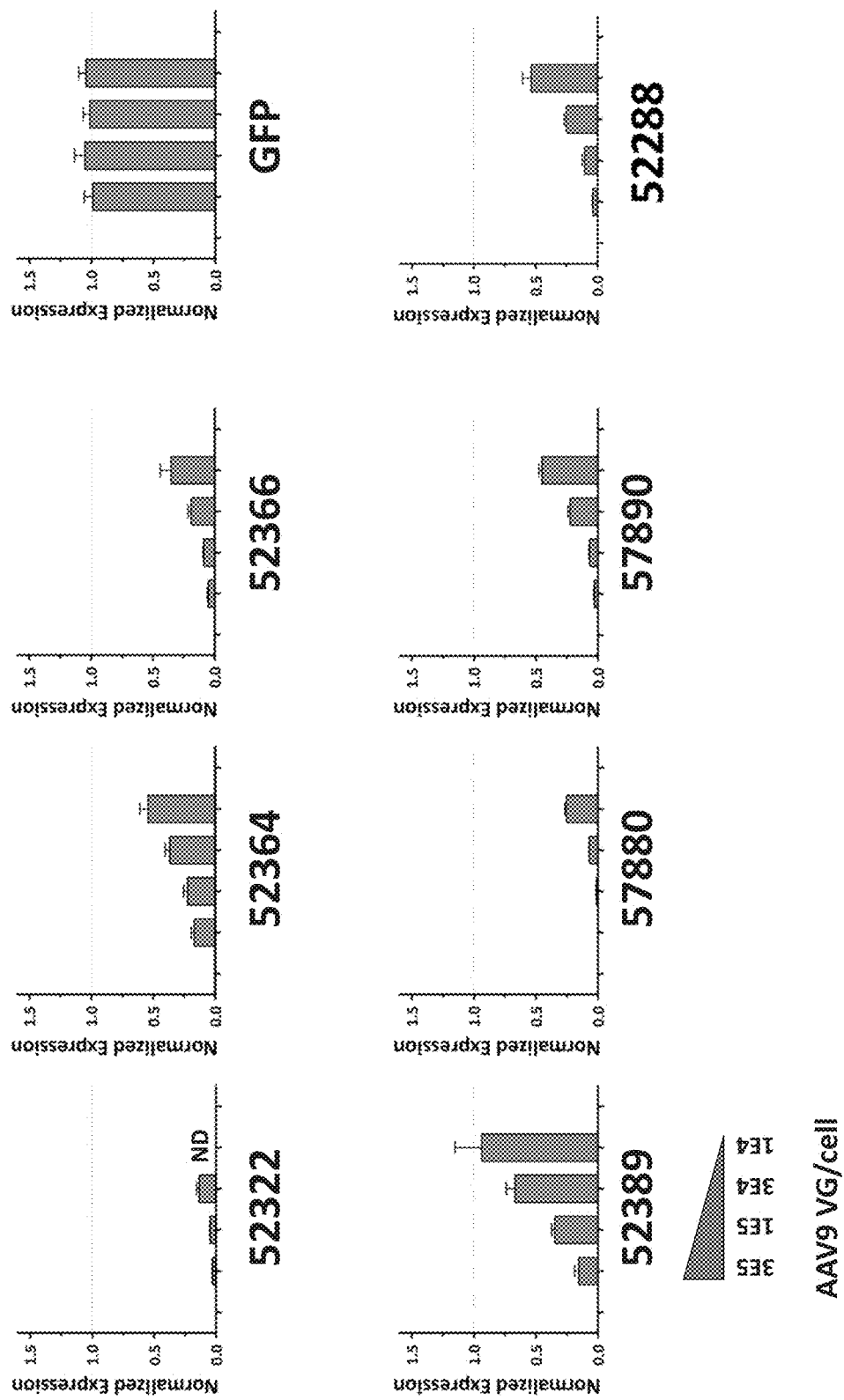

Figure 5A
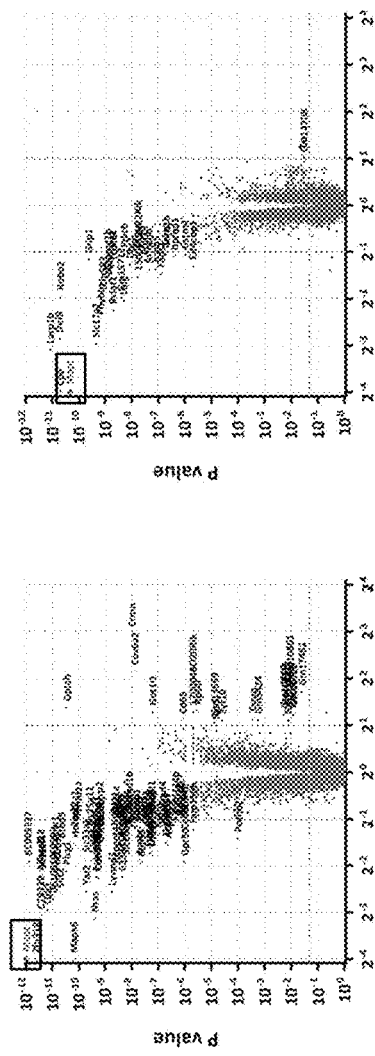
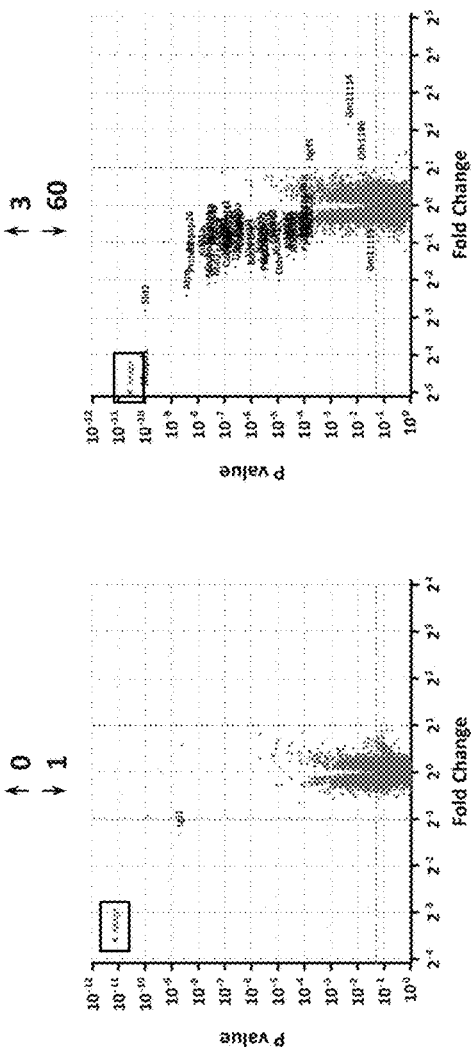

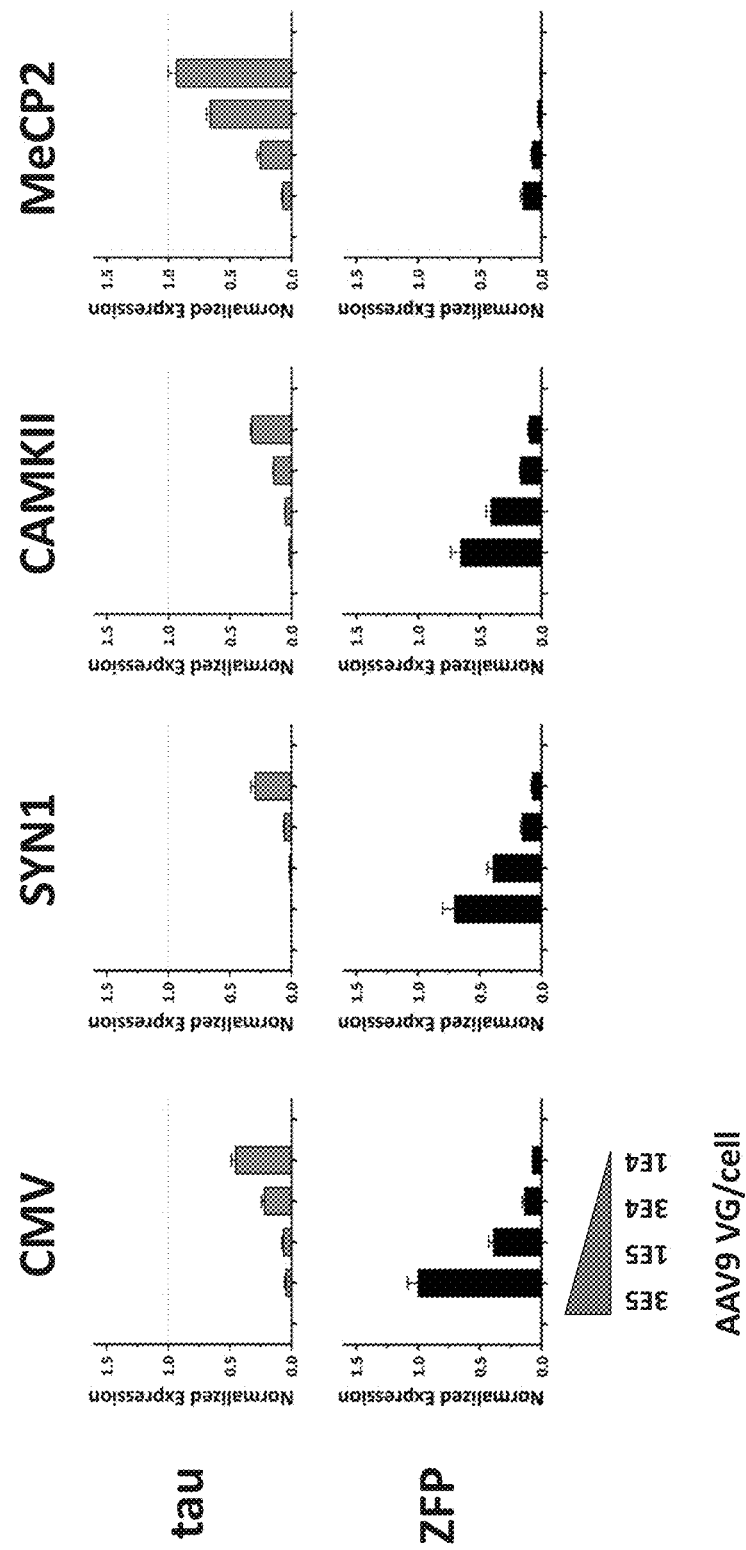

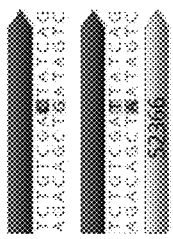
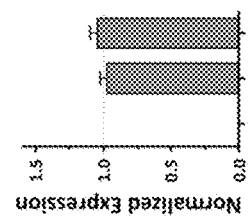
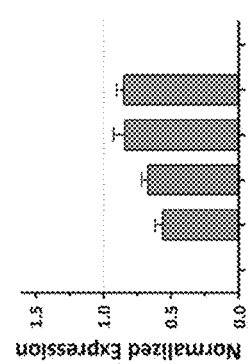
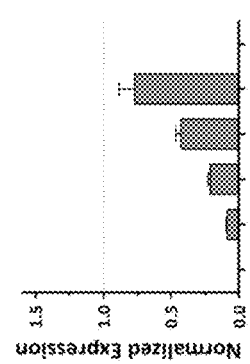
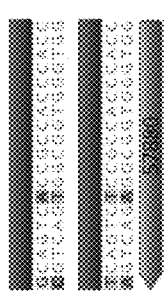
Figure 7A
Figure 7B

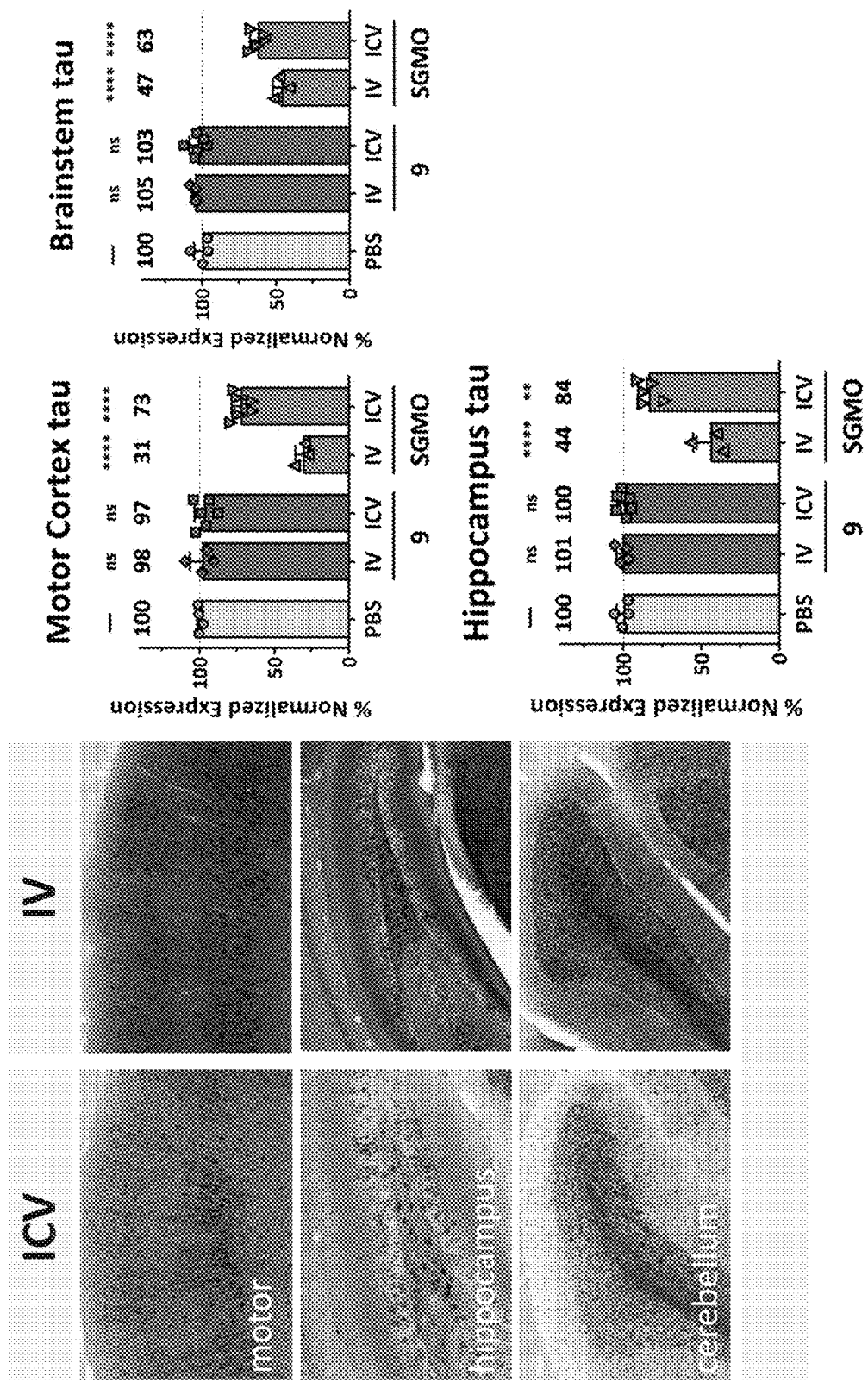

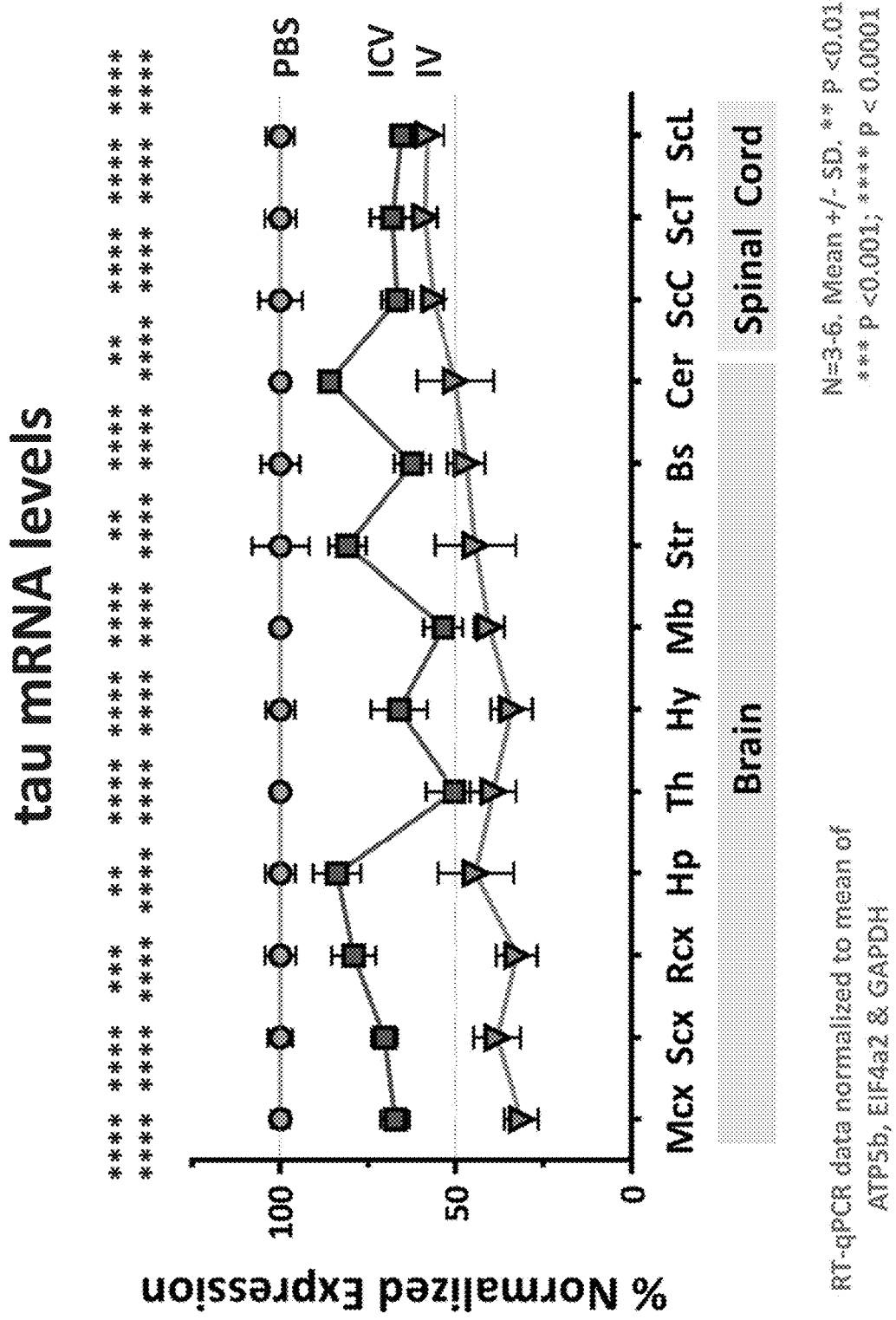

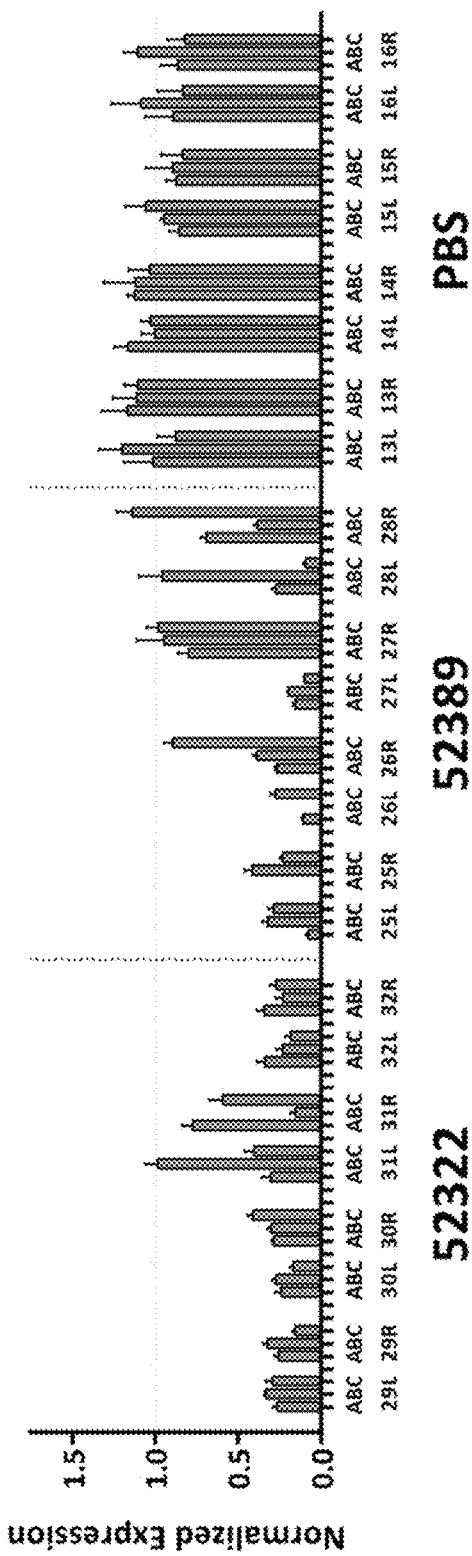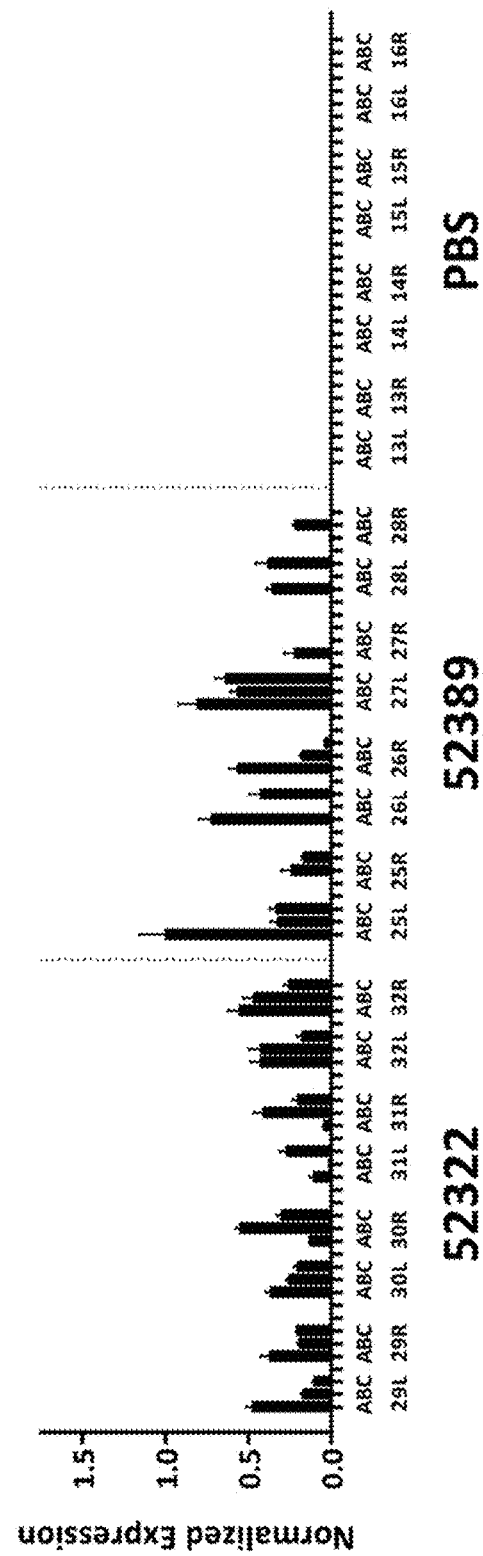

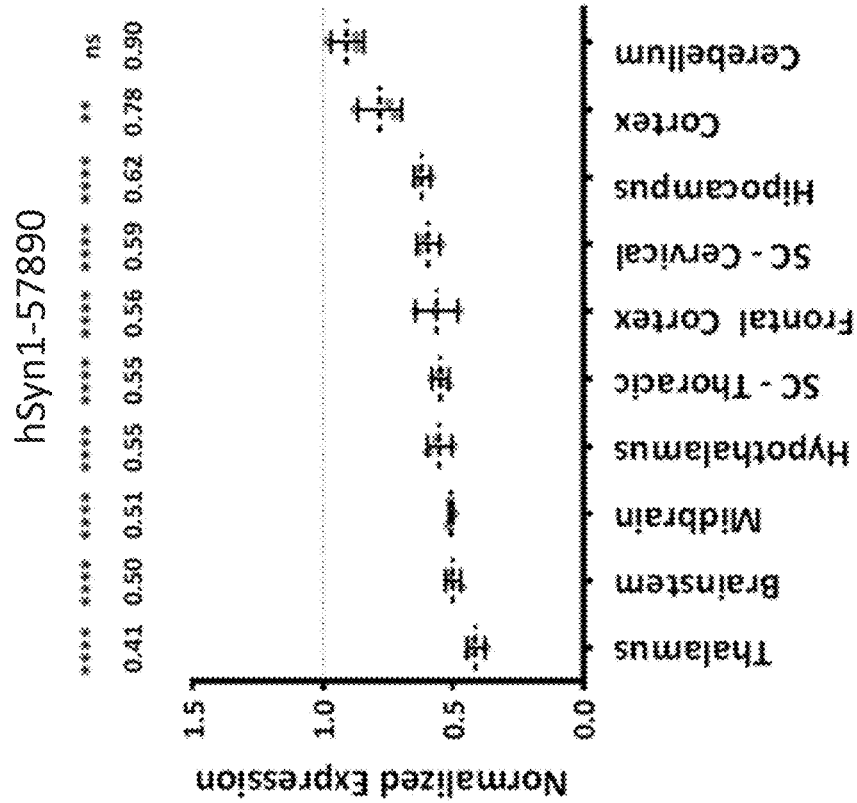
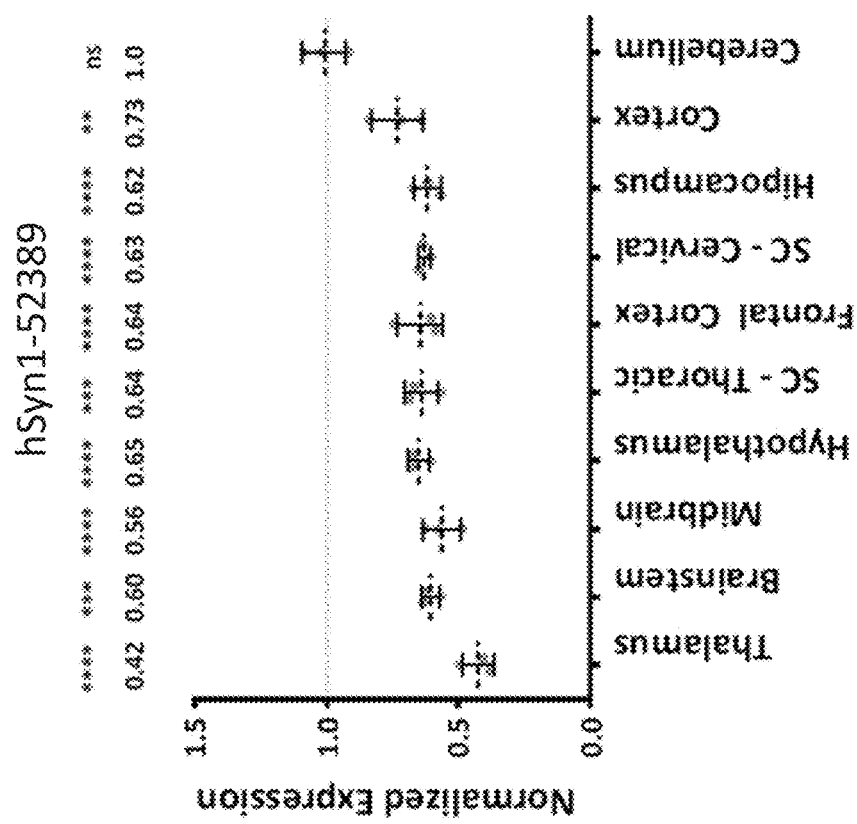
Figure 8F

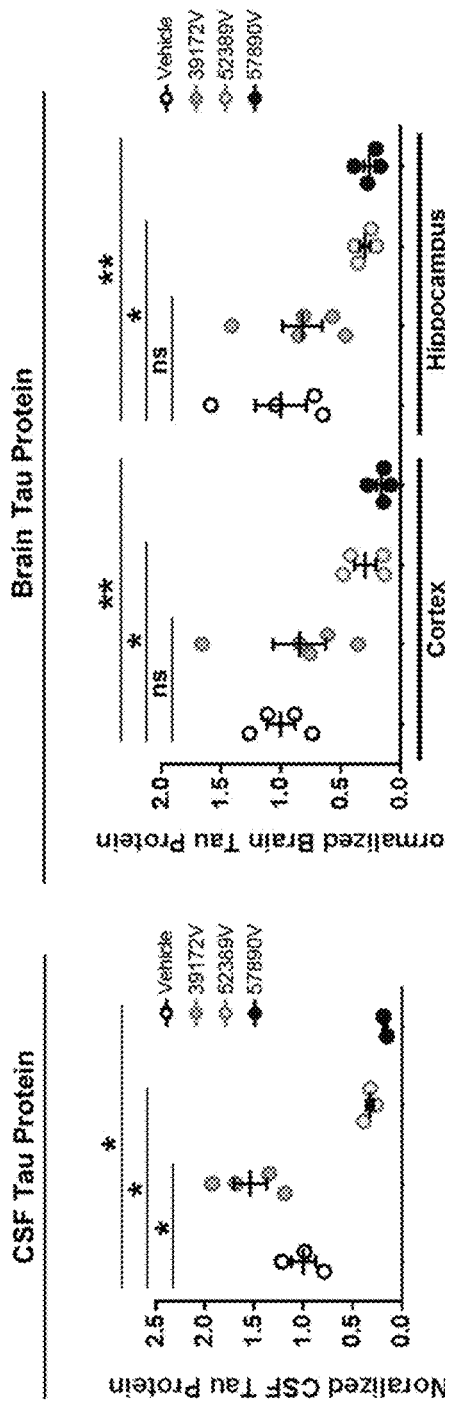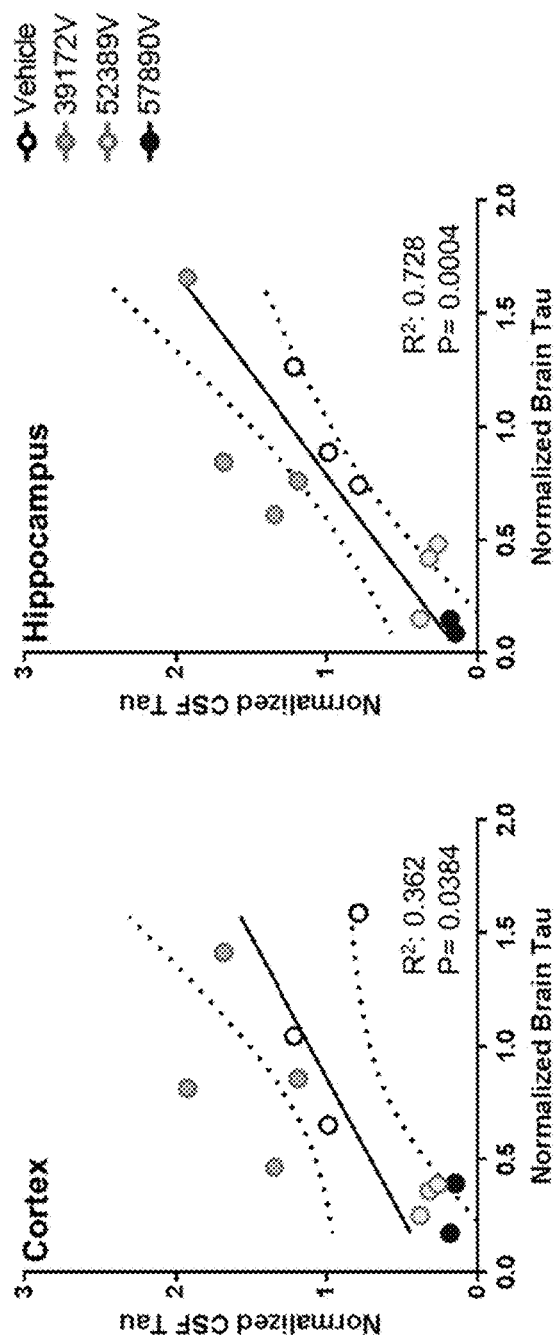
Figure 8H

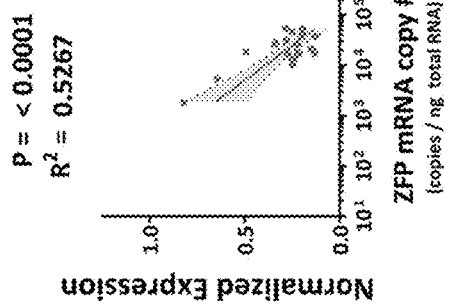
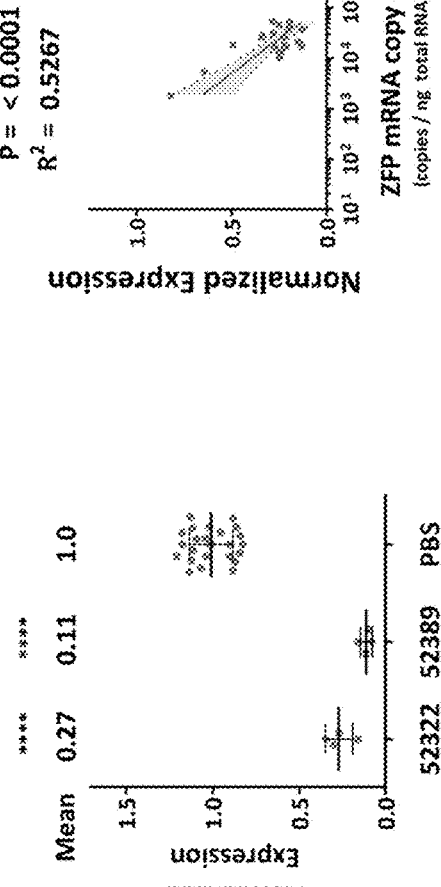
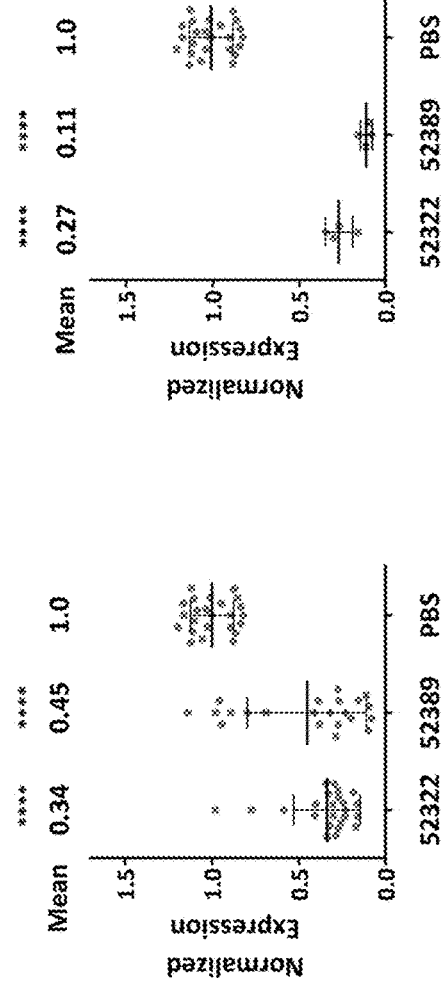
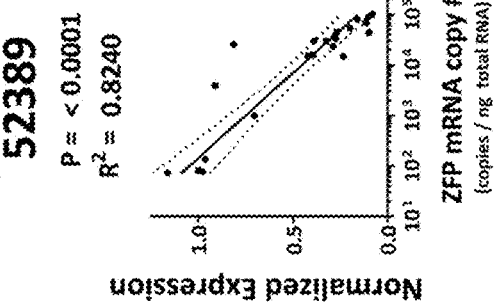
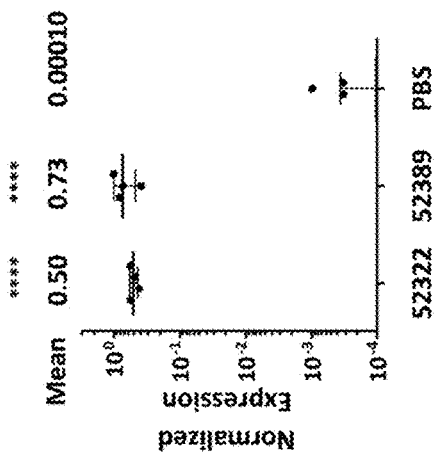
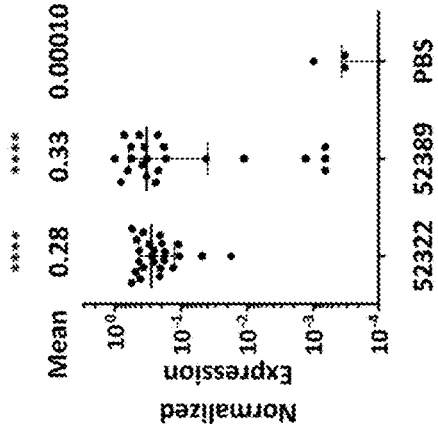

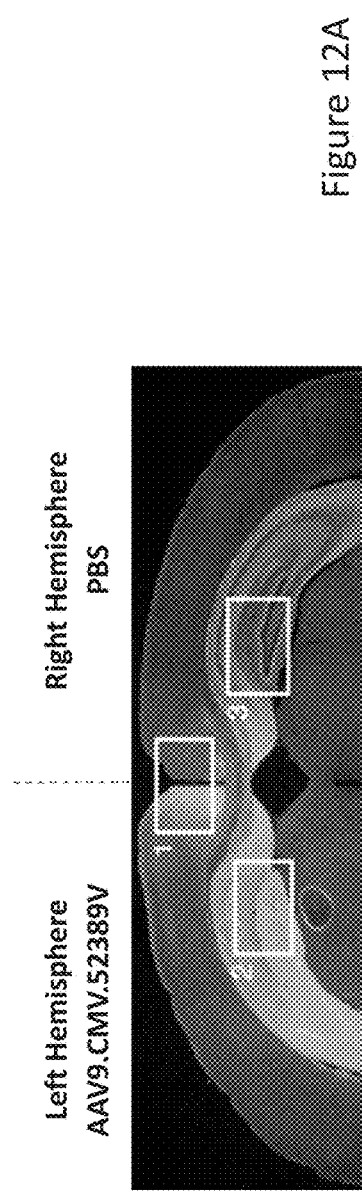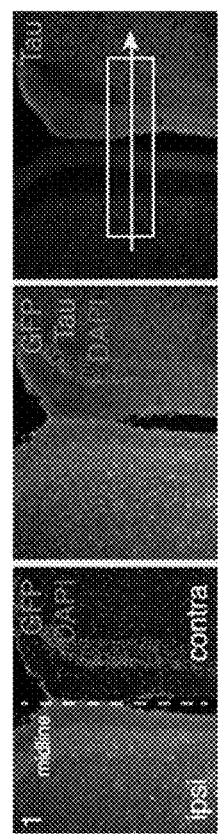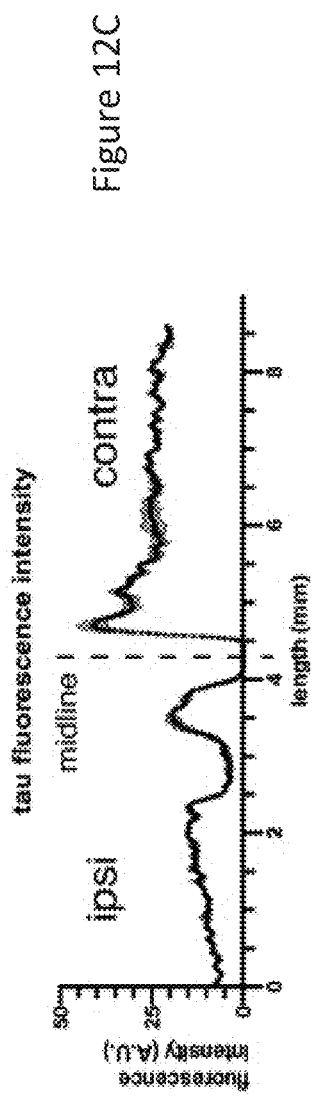
Figure 12A
Figure 12B
Figure 12C

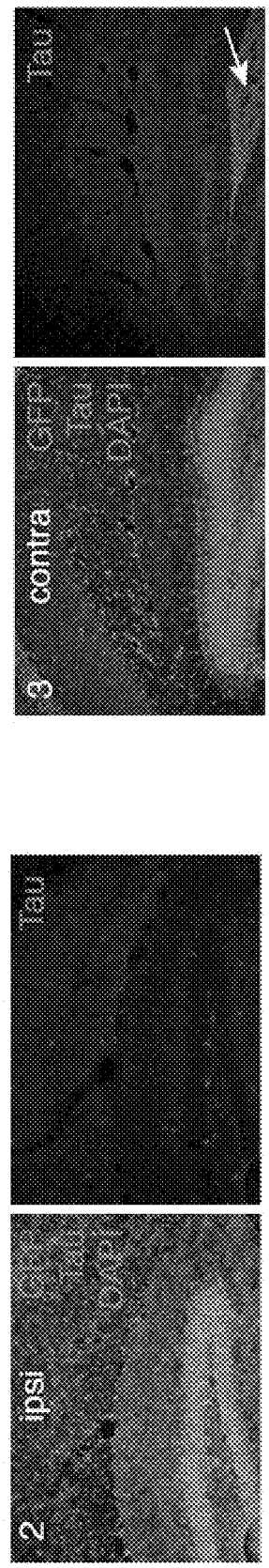
Figure 12D
Figure 12E
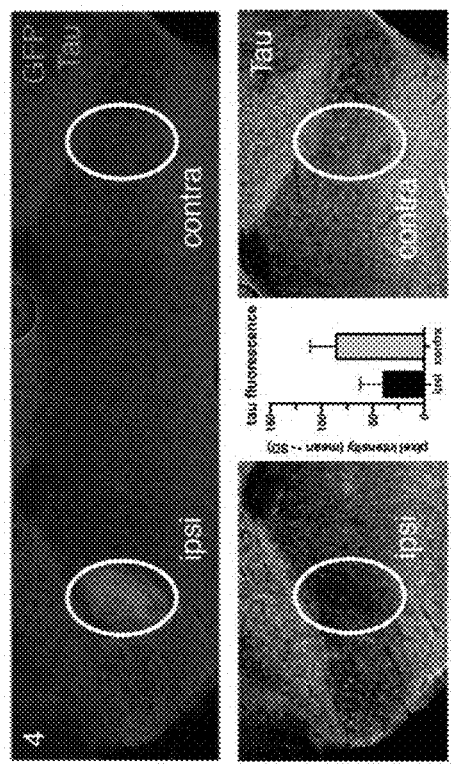
Figure 12F

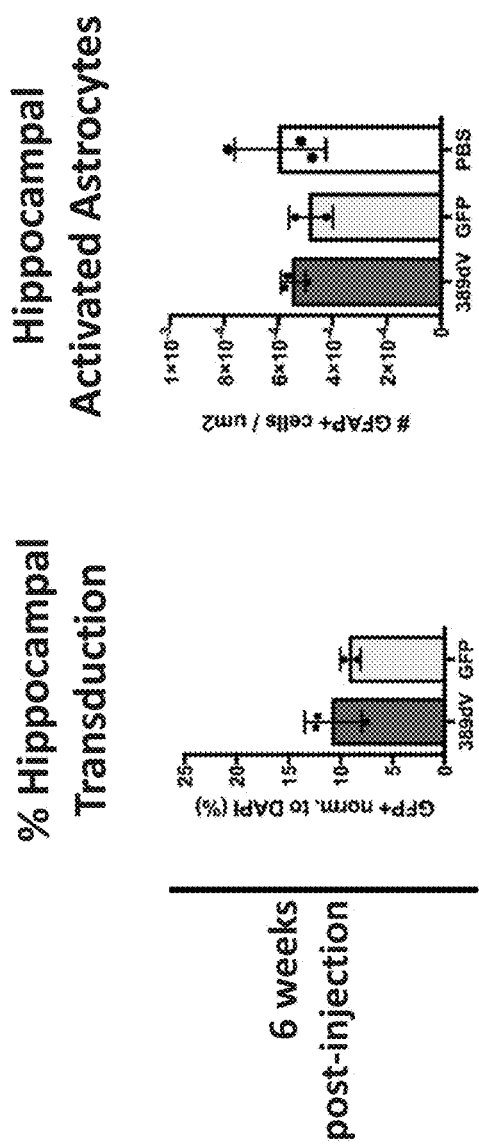
Figure 13A, Figure 13B, Figure 13C, Figure 13D, Figure 13E, Figure 13F

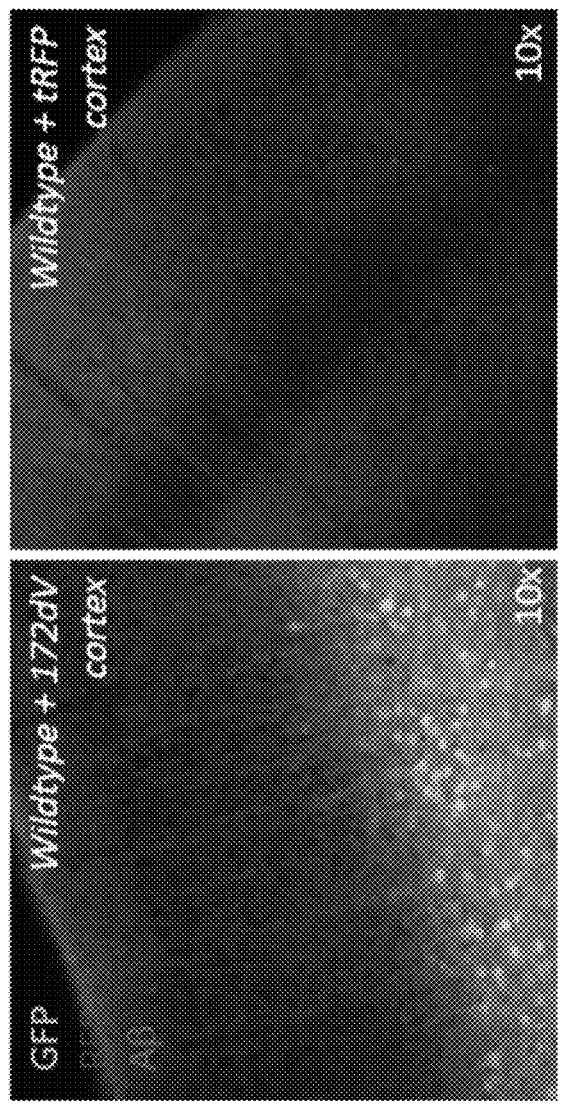
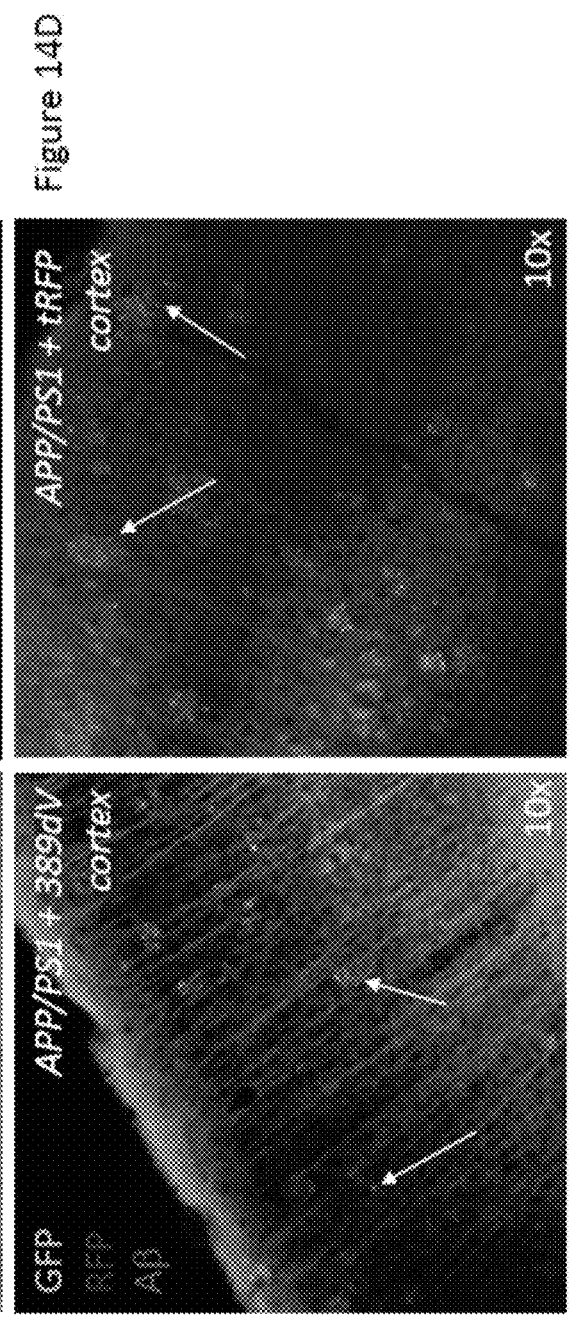
Figure 14A
Figure 14B
Figure 14C
Figure 14D

TAU MODULATORS AND METHODS AND COMPOSITIONS FOR DELIVERY THEREOF

CROSS-REFERENCE TO RELATED APPLICATIONS

The present application claims the benefit of U.S. Provisional Application No. 62/428,871, filed Dec. 1, 2016; U.S. Provisional Application No. 62/450,895, filed Jan. 26, 2017; U.S. Provisional Application No. 62/466,198, filed Mar. 2, 2017; U.S. Provisional Application No. 62/500,807, filed May 3, 2017; and U.S. Provisional Application No. 62/584,342, filed Nov. 10, 2017, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 28, 2017, is named 8325-0140_SL.txt and is 10,420 bytes in size.

TECHNICAL FIELD

The present disclosure is in the field of diagnostics and therapeutics for tauopathies such as Alzheimer's Disease.

BACKGROUND

Many, perhaps most physiological and pathophysiological processes can be associated by the aberrant up or down regulation of gene expression. Examples include the inappropriate expression of proinflamatory cytokines in rheumatoid arthritis, under expression of the hepatic LDL receptor in hypercholesteremia, over expression of proangiogenic factors and under expression of antiangiogenic factors in solid tumor growth, to name just a few. In addition, pathogenic organisms such as viruses, bacteria, fungi, and protozoa could be controlled by altering gene expression.

Promoter regions of genes typically comprise proximal, core and downstream elements, and transcription can be regulated by multiple enhancers. These sequences contain multiple binding sites for a variety of transcription factors and can activate transcription independent of location, distance or orientation with respect to the promoter sequence. In order to achieve gene expression regulation, enhancer-bound transcription factors loop out the intervening sequences and contact the promoter region. In addition, activation of eukaryotic genes can require de-compaction of the chromatin structure, which can be carried out by recruitment of histone modifying enzymes or ATP-dependent chromatin remodeling complexes such that chromatin structure is altered and the accessibility of the DNA to other proteins involved in gene expression is increased (Ong and Corces (2011) *Nat Rev Genetics* 12:283).

Perturbation of chromatin structure can occur by several mechanisms-some which are localized for a specific gene, and others that are genome wide and occur during cellular processes such as mitosis where condensation of the chromatin is required. Lysine residues on histones may become acetylated, effectively neutralizing the charge interaction between the histone proteins and the chromosomal DNA. This has been observed at the hyperacetylated and highly transcribed β-globin locus which has also been shown to be DNAse sensitive, a hallmark of general accessibility. Other types of histone modifications that have been observed include methylation, phosphorylation, deamination, ADP ribosylation, addition of β-N-acetlyglucosamine sugars, ubiquitylation and sumoylation (see Bannister and Kouzarides (2011) *Cell Res* 21:381).

Repression or activation of disease associate genes has been accomplished through the use of engineered transcription factors. Methods of designing and using engineered zinc finger transcription factors (ZFP-TF) are well documented (see for example U.S. Pat. No. 6,534,261), and more recently both transcription activator like effector transcription factors (TALE-TF) and clustered regularly interspaced short palindromic repeat Cas based transcription factors (CRISPR-Cas-TF) have also been described (see review Kabadi and Gersbach (2014) *Methods* 69(2): 188-197). Non-limiting examples of targeted genes include phospholamban (Zhang et al., (2012) *Mol Ther* 20(8): 1508-1515), GDNF (Laganiere et al., (2010) *J. Neurosci* 30(49): 16469) and VEGF (Liu et al., (2001) *J Biol Chem* 276:11323-11334). In addition, activation of genes has been achieved by use of a CRIPSR/Cas-acetyltransferase fusion (Hilton et al., (2015) *Nat Biotechnol* 33(5):510-517). Engineered TFs that repress gene expression (repressors) have also been shown to be effective in treating trinucleotide disorders such as Huntingtin's Disease (HD). See, e.g., U.S. Pat. No. 8,956,828 and U.S. Patent Publication No. 2015/0335708.

Alzheimer's Disease (AD), is a complex, multifactorial disease characterized by several distinct disease mechanisms that are not completely understood, and may interact with each other in as of yet poorly understood ways. An estimated 5.3 million Americans of all ages have AD, making it one of the top ten causes of death in America, and it is estimated that by the year 2050, there will be 106.2 million people worldwide with the disease (van Dijk et al., (2015) *Front Neurosci* 9, art. 173). The disease is more prevalent in women (two thirds of cases) and also people of African or Hispanic descent are more likely to develop AD than people of Caucasian descent. The causes of AD appear to be related to genetics (especially for early onset, 5% of cases) and environmental and lifestyle factors. Typically, the disease is diagnosed in a person's mid-sixties although by the time a diagnosis is made, the disease has been progressing for years or even decades. The disease continues to be progressive over time, and thus far no therapeutic interventions have been identified that curtail or reverse the effects of the disease.

The hallmark of the disease is a loss of synapses in the brain, which leads to cognitive decline. In a healthy brain, synaptic plasticity is thought to be what allows learning and memory formation. During the course of AD, synaptic plasticity is altered and many of the mechanisms involved in maintaining that plasticity are dysregulated, leading to synapse dysfunction and collapse (Spires-Jones and Hyman (2014) *Neuron* 82:756).

Although it appears that there are many molecular factors that influence the onset and progression of AD, most of the scientific focus has been on two main players in the disease. The first is a 40-42 amino acid fragment of the amyloid precursor protein (APP) called amyloid β (Aβ), which is generated via proteolytic cleavage by beta secretase and gamma secretase (Olsson et al., (2014) *J Biol Chem* 289(3): 1540-1550). Insoluble Aβ fragments accumulate in 'senile' plaques in the brain although there does not seem to be a strict correlation between the presence of these plaques and neurodegeneration.

The other actor, Tau, has also received a great deal of attention. Tau is a microtubule-associated protein that was originally thought to stabilize microtubules. In AD patients, and in the elderly in general but to a lesser extent, tau can accumulate in neurofibrillary tangles (NFT). During the course of the disease, tau becomes hyperphosphorylated and detaches from microtubules and accumulates in filaments. In contrast to the Aβ plaques, there is a direct correlation between the presence of NFT and cognitive decline (Spires-Jones and Hyman, ibid).

Interestingly, both tau and Aβ appear to have important roles in normal synaptic function. Tau appears to play an important role in transporting mitochondria in the cell to the synapse and it has been shown that overexpression of tau inhibits this transport. Impairment of mitochondrial transport is thought to cause synapse loss due to the essential roles mitochondria play in ATP production and calcium buffering. Aβ appears to play role in synapse plasticity in a healthy cell. However, the accumulation of these two proteins in plaques and tangles is associated with AD progression. In fact, it appears that the appearance of the amyloid plaques is important in the earliest stages of AD and this leads to the appearance of the NFT, and that the two proteins actually act synergistically with each other to speed progression of the disease (Pooler et al., (2015) *Acta Neuropath Comm* 3(14):1). It is becoming more apparent however that the soluble forms of these proteins contribute to toxicity (Spires-Jones and Hyman, ibid).

In fact, abnormal levels and/or aggregation of tau has been implicated in a number of conditions, collectively referred to as tauopathies. These include Alzheimer's Disease AD, Frontotermporal dementia (FTD, see Benussi et al., (2015) *Front Ag Neuro* 7, art. 171)), Progressive Supranuclear Palsy (PSP), intractable genetic epilepsies (e.g. Dravat syndrome, see Gheyara et al., (2014) *Ann Neurol* 76:443-456) and Corticobasal degeneration (CBD, see Scholz and Bras 2015, *Intl. Mot Sci* 16(10): 24629-24655). Reduction of tau expression in adult mice using antisense oligonucleotides directly to the cerebral spinal fluid (CSF) caused a complete or partial reduction in tau levels and also protected the treated mice from chemical induced seizures in terms of seizure severity (DeVos et al., (2013) *J of NeuroSci* 33(31): 12887).

AD has been shown to proceed through the brain in a hierarchical pattern, starting at the entorhinal cortex and then spreading through the hippocampal formation, limbic and association cortices, and finally affecting most brain areas in the late stages of the disease. Interestingly, progression of AD is marked by the appearance of NFT, implicating tau in the later stages of the disease. It has even been suggested that tau may have prion like properties, as work showing that misfolded, highly phosphorylated tau protein is more easily taken up by neurons and may propagate the disease through the brain, and that this misfolded tau isolated from brains of AD patients can be readily taken up by mouse neurons (Takeda et al., (2015) *Nat Comm* doi:10.1038/ncomms9490; Hyman (2014) *Neuron* 82:1189). In addition, work done with a transgenic mouse model showed that expression of a human tau mutant that is linked to tangle formation only in the entorhinal cortex of the mouse brain led to the misfolding of mouse tau and aggregation of that tau in neurons without any detectable human tau expression (de Calignon et al., (2012) *Neuron* 73:685-697), suggesting that the misfolded human protein is able to 'seed' misfolding and cause aggregation of the mouse proteins. Further, genetic reduction or loss of endogenous mouse tau is protective against neuropathological toxicity caused by overexpression of a mutant human tau transgene (Wegmann et al., (2015) *EMBO J*. 34(24):3028-41).

Thus, there remains a need for methods for the prevention and/or treatment of tauopathies, including AD, FTD, PSP CBD and seizures; including for modalities that exhibit widespread delivery to the brain.

SUMMARY

Disclosed herein are methods and compositions for diagnosing, preventing and/or treating one or more taupathies, such as Alzheimer's Disease (AD). In particular, provided herein are methods and compositions for modifying (e.g., modulating expression of) a tau allele so as to treat at least one tauopathy such as AD, including engineered transcription factor repressors (that repress tau expression). Further, these methods and compositions can be used to modify a tau allele for the treatment and/or prevention of other tauopathies, including AD, FTD, PSP CBD and/or seizures. In particular, provided herein are methods and compositions for detecting, reducing and/or eliminating tau aggregates in a subject with a tauopathy.

Thus, described herein are genetic modulators of a microtubule associated protein tau (MAPT) gene, the modulator comprising: a DNA-binding domain that binds to a target site of at least 12 nucleotides in the MAPT gene; and functional domain (e.g., a transcriptional regulatory domain (such as a repression domain or an activation domain) or nuclease domain). Any DNA-binding domain can be used, including but not limited to, a zinc finger protein (ZFP), a TAL-effector domain protein (TALE), a single guide RNA (of a CRISPR systems), an Argonaute protein and the like. One or more polynucleotides, including viral and non-viral gene delivery vehicles (e.g., as mRNA, plasmids, AAV vectors, lentiviral vectors, Ad vectors) encoding the genetic modulators as described herein (or one or more components thereof on the same or different polynucleotides) are also provided. In certain embodiments, the gene delivery vehicle comprises an AAV vector, including, but not limited, to AAV1, AAV2, AAV3, AAV4, AAV5, AAV6, AAV8, AAV 8.2, AAV9, AAV rh10, pseudotypes of these vectors (e.g., as AAV2/8, AAV2/5, AAV2/6, AAV2/9, etc.), including AAV vector variants known in the art (e.g. U.S. Pat. No. 9,585,971 and U.S. Provisional Patent Application No. 62/503,121). Pharmaceutical compositions and isolated cells comprising one or more of the genetic modulators, one or more polynucleotides, and/or one or more gene delivery vehicles are also provided. The invention also provides methods and uses for modulating MAPT expression in a subject in need thereof, including by providing to the subject one or more polynucleotides, one or more gene delivery vehicles, and/or a pharmaceutical composition as described herein. In certain embodiments, the compositions described herein are used to repress MAPT expression in the subject, including for treatment and/or prevention of a tauopathy (e.g., by reducing the amount of tau in the subject). The compositions described herein reduce tau levels for sustained periods of time (6 months to year or more) in the brain (including but not limited to frontal cortex, anterior cortex, posterior cortex, hippocampus, brain stem, striatum, thalamus, midbrain, cerebellum) and spinal cord (including but not limited to lumbar, thoracic and cervical regions). The compositions described herein may be provided to the subject by any administration means, including but not limited to, intracerebroventricular, intrathecal, intracranial, intravenous, orbital (retro-orbital (RO)) and/or intracisternal administration. Kits comprising one or more of the compositions (e.g., genetic modulators, polynucleotides, pharmaceutical compositions and/or cells) as described herein as well as instructions for use of these compositions are also provided.

Thus, in one aspect, engineered (non-naturally occurring) genetic modulators (e.g., repressors) of one or more tau genes are provided. The genetic tau modulators may comprise systems (e.g., zinc finger proteins, TAL effector (TALE) proteins or CRISPR/dCas-TF) that modulate (e.g., repress) expression of a tau allele. Engineered zinc finger proteins or TALEs are non-naturally occurring zinc finger or TALE proteins whose DNA binding domains (e.g., recognition helices or RVDs) have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). Similarly, any of the TALE proteins described herein may include any number of TALE RVDs. In some embodiments, at least one RVD has non-specific DNA binding characteristics. In some embodiments, at least one recognition helix (or RVD) is non-naturally occurring. A CRISPR/Cas-TF includes a single guide RNA that binds to a target sequence. In certain embodiments, the engineered transcription factor binds to (e.g., via a ZFP, TALE or sgRNA DNA binding domain) to an at least 12 base pair target site in a tau-encoding gene, for example a target site comprising at least 12 base pairs (e.g., 12, 13, 14, 15, 16, 17, 18 or more) of Tables 1 through 3 (SEQ ID Nos:1 to 6, 33 and 44-46), including contiguous or non-contiguous sequences within these target sites. In certain embodiments, the zinc finger proteins DNA-binding domains have the recognition helices in the proteins shown in any of Tables 1 to 3, including the ZFPs designated 52288, 52322, 52366, 57890, 57880, 65888, 52364, 52389, 65894, 57930, 65918, 65920, 65887, 57947, 65968, 65976 or 65860 of Tables 1, 2 and 3. In certain embodiments, the genetic modulator is a genetic repressor that comprises a DNA-binding domain (ZFP, TALE, single guide RNA) as described herein operably linked to a transcriptional repression domain. In other embodiments, the genetic modulator is a genetic repressor comprising a DNA-binding domain (ZFP, TALE, single guide RNA) as described herein operably linked to at least one nuclease domain (e.g., one, two or more nuclease domains). The resulting nuclease is capable of genetically modifying (by insertions and/or deletions) the target gene, for example, within the DNA-binding domain target sequence(s); within the cleavage site(s); near (1-50 or more base pairs) from the target sequence(s) and/or cleavage site(s); and/or between paired target sites when a pair of nucleases is used for cleavage.

In certain embodiments, the zinc finger proteins (ZFPs), Cas protein of a CRISPR/Cas system or TALE proteins as described herein can be placed in operative linkage with a regulatory domain (or functional domain) as part of a fusion protein. The functional domain can be, for example, a transcriptional activation domain, a transcriptional repression domain and/or a nuclease (cleavage) domain. By selecting either an activation domain or repression domain for use with the DNA-binding domain, such molecules can be used either to activate or to repress tau expression. In certain embodiments, the functional or regulatory domains can play a role in histone post-translational modifications. In some instances, the domain is a histone acetyltransferase (HAT), a histone deacetylase (HDAC), a histone methylase, or an enzyme that sumolyates or biotinylates a histone or other enzyme domain that allows post-translation histone modification regulated gene repression (Kouzarides (2007) Cell 128(4):693-705). In some embodiments, a molecule comprising a ZFP, dCas or TALE targeted to a tau gene (e.g., MAPT) as described herein fused to a transcriptional repression domain that can be used to down-regulate tau expression is provided. In some embodiments, the methods and compositions of the invention are useful for treating eukaryotes. In certain embodiments, the activity of the regulatory domain is regulated by an exogenous small molecule or ligand such that interaction with the cell's transcription machinery will not take place in the absence of the exogenous ligand. Such external ligands control the degree of interaction of the ZFP-TF, CRISPR/Cas-TF or TALE-TF with the transcription machinery. The regulatory domain(s) may be operatively linked to any portion(s) of one or more of the ZFPs, dCas or TALEs, including between one or more ZFPs, dCas or TALEs, exterior to one or more ZFPs, dCas or TALEs and any combination thereof. In preferred embodiments, the regulatory domain results in a repression of gene expression of the targeted tau gene. Any of the fusion proteins described herein may be formulated into a pharmaceutical composition.

In some embodiments, the methods and compositions of the invention include use of two or more fusion proteins as described herein, for instance two or more tau modulators (e.g., tau repressors). The two or more fusion proteins may bind to different target sites and comprise the same or different functional domains. Alternatively, the two or more fusion proteins as described herein may bind to the same target site but include different functional domains. In some instances, three or more fusion proteins are used, in others, four or more fusion proteins are used, while in others, 5 or more fusion proteins are used. In preferred embodiments, the two or more, three or more, four or more, or five or more fusion proteins are delivered to the cell as nucleic acids. In preferred embodiments, the fusion proteins cause a repression of the expression of the targeted gene. In some embodiments, two fusion proteins are given at doses where each protein is active on its own but in combination the repression activity is additive. In preferred embodiments, two fusion proteins are given at doses where neither is active on its own, but in combination, the repression activity is synergistic.

In some embodiments, the engineered DNA binding domains as described herein can be placed in operative linkage with nuclease (cleavage) domains as part of a fusion protein. In some embodiments, the nuclease comprises a Ttago nuclease. In other embodiments, nuclease systems such as the CRISPR/Cas system may be utilized with a specific single guide RNA to target the nuclease to a target location in the DNA. In certain embodiments, such nucleases and nuclease fusions may be utilized for targeting tau alleles in stem cells such as induced pluripotent stem cells (iPSC), human embryonic stem cells (hESC), mesenchymal stem cells (MSC) or neuronal stem cells wherein the activity of the nuclease fusion will result in reduced expression of a tau allele. In certain embodiments, pharmaceutical compositions comprising the modified stem cells are provided.

In yet another aspect, a polynucleotide encoding any of the DNA binding proteins, nucleases and/or transcription factors described herein is provided. In certain embodiments, the polynucleotide comprises at least one AAV vector (or pseudotype or variant thereof), including but not limited to one or more AAV2, AAV2/9, AAV6, or an AAV9 vector, including but not limited to one or more AAV vectors as described in U.S. Pat. No. 9,585,971 or 7,198,951) and/or one or more AAV vectors as described in U.S. Provisional Patent Application No. 62/503,121.

In other aspects, the invention comprises delivery of a donor nucleic acid to a target cell. The donor may be delivered prior to, after, or along with the nucleic acid encoding the nuclease(s). The donor nucleic acid may comprise an exogenous sequence (transgene) to be integrated into the genome of the cell, for example, an endogenous locus. In some embodiments, the donor may comprise a full-length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion. In some embodiments, the donor encodes a transcription factor capable of repressing Tau expression. In other embodiments, the donor encodes a RNA molecule that inhibits expression of the Tau protein.

In some embodiments, the polynucleotide encoding the DNA binding protein is an mRNA. In some aspects, the mRNA may be chemically modified (See e.g. Kormann et al., (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In yet another aspect, a gene delivery vector comprising any of the polynucleotides (e.g., encoding the genetic modulators (repressors)) as described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). In certain embodiments, the AAV vector is an AAV2, AAV6 or AAV9 vector. In some embodiments, the AAV vector is an AAV variant capable of crossing the blood-brain barrier (e.g. U.S. Pat. No. 9,585,971 and U.S. Provisional Patent Application No. 62/503,121). Also provided herein are adenovirus (Ad) vectors, LV or adenovirus associate viral vectors (AAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments, the vector is pseudo-typed with a VSV-G envelope, or with other envelopes.

Additionally, pharmaceutical compositions comprising the nucleic acids (e.g., delivery (e.g., AAV) vectors comprising sequences encoding the artificial transcription factors (tau repressors) described herein) and/or proteins (e.g., ZFPs, Cas or TALEs or fusion proteins comprising the ZFPs, Cas or TALEs) are also provided. For example, certain compositions include a nucleic acid comprising a sequence that encodes one of the ZFPs, Cas or TALEs described herein operably linked to a regulatory sequence, combined with a pharmaceutically acceptable carrier or diluent, wherein the regulatory sequence allows for expression of the nucleic acid in a cell. In certain embodiments, the ZFPs, CRISPR/Cas or TALEs encoded are specific for a mutant tau allele. In some embodiments, pharmaceutical compositions comprise ZFPs, CRISPR/Cas or TALEs that modulate a mutant tau allele and ZFPs, CRISPR/Cas or TALEs that modulate a neurotrophic factor. Protein based compositions include one of more ZFPs, CRISPR/Cas or TALEs as disclosed herein and a pharmaceutically acceptable carrier or diluent.

In yet another aspect also provided is an isolated cell comprising any of the proteins, polynucleotides and/or compositions as described herein.

In another aspect, provided herein are methods for treating and/or preventing a tauopathy such as Alzheimer's Disease or seizure using the methods and compositions described herein. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations comprising a ZFP or TALE, or altered with the ZFNs, TALENs, Ttago or the CRISPR/Cas nuclease system of the invention. Administration of compositions as described herein (proteins, polynucleotides, cells and/or pharmaceutical compositions comprising these proteins, polynucleotides and/or cells) result in a therapeutic (clinical) effect, including, but not limited to, amelioration or elimination of any the clinical symptoms associate with AD, tauopathies or seizure as well as an increase in function and/or number of CNS cells (e.g., neurons, astrocytes, myelin, etc.). In certain embodiments, the compositions and methods described herein reduce tau expression (as compared to controls not receiving the artificial repressors as described herein) by at least 30%, or 40%, preferably by at least 50%, even more preferably by at least 70%. In some embodiments, at least 50% reduction is achieved.

In a still further aspect, described here is a method of delivering a repressor of tau to the brain of a subject (e.g., mammalian subject such as a mouse, human or non-human primate (NHP)) using a viral or non-viral vector. In certain embodiments, the viral vector is an AAV vector, for instance an AAV9 vector, or an AAV vector variant as described in U.S. Pat. No. 9,585,971 or U.S. Provisional Patent Application No. 62/503,121. Delivery may be to any brain region, for example, the hippocampus or entorhinal cortex by any suitable means including via the use of a cannula or any other delivery technology. Any AAV vector that provides widespread delivery of the repressor to brain of the subject, including via anterograde and retrograde axonal transport to brain regions not directly administered the vector (e.g., delivery to the putamen results in delivery to other structures such as the cortex, substantia nigra, thalamus, etc.). In certain embodiments, the subject is a human and in other embodiments, the subject is a non-human primate. The administration may be in a single dose or in multiple administrations (at any timing between administrations).

Thus, in other aspects, described herein is a method of preventing and/or treating a tauopathy (e.g., AD) in a subject, the method comprising administering a repressor of a tau allele to the subject using one or more AAV vectors. In certain embodiments, the AAV encoding the repressor is administered to the CNS (brain and/or CSF) via any delivery method including but not limited to, intracerebroventricular, intrathecal, or intracisternal delivery. In other embodiments, the AAV encoding the repressor is administered directly into the parenchyma (e.g., hippocampus and/or entorhinal cortex) of the subject. In other embodiments, the AAV encoding the repressor is administered intravenously (IV). In any of the methods described herein, the administering may be done once (single administration) or may be done multiple times (with any time between administrations). When administered multiple times, the same or different dosages and/or delivery vehicles of modes of administration may be used (e.g., different AAV vectors administered IV and/or ICV). The methods include methods of reducing the aggregation of tau in the subject (e.g., reducing NFTs characteristic of tau aggregation) for example in AD neurons of a subject with AD; methods of reducing apoptosis in a neuron or population of neurons (e.g., an AD neuron or population of AD neurons); methods of reducing neuronal hyperexcitability; methods of reducing amyloid beta induced toxicity (e.g. synapse loss and/or neuritic dystrophy); and/or methods of reduce loss to one or more cognitive functions in AD subjects, all in comparison with a subject not receiving the method, or in comparison to the subject themselves prior to receiving the methods. Thus, the methods described herein result in reduction in biomarkers and/or symptoms of tauopathies, including one or more the following: neurotoxicity, gliosis, dystrophic neurites, spine loss, excitotoxicity, cortical and hippocampal shrinkage, dendritic tau accumulation, cognitive (e.g., the radial arm maze and the Morris water maze in rodent models, fear conditioning, etc.), and/or motor deficits.

In some aspects, the methods and compositions of the invention for reducing the amount of a pathogenic tau species in a cell are provided. In some embodiments, the methods result in a reduction of hyperphosphorylated tau. In some instances, the reduction of hyperphosphorylated tau results in a reduction of soluble or granular tau. In other embodiments, the reduction of pathogenic tau species decreases tau aggregation and causes a reduction in neurofibrillary tangles (NFTs) as compared to a cell or subject that has not been treated following the methods and/or with the compositions of the invention. In further embodiments, the methods of reversing the amount of NFTs observed in a cell are provided. In still further embodiments, the methods and compositions of the invention cause a slowing of the propagation of pathogenic tau species (NFTs, hyperphosphorylated tau) within the brain of a subject. In some embodiments, propagation of pathogenic tau across the brain is halted, and in other embodiments, propagation of pathogenic tau across the brain is reversed. In further embodiments, the number of dystrophic neurites associated with amyloid β plaques in the brain is reduced. In some embodiments, the number of dystrophic neurites is reduced to the levels found in an age-matched wild type brain. In further embodiments, provided herein are methods and compositions for reducing hyperphosphorylated tau associated with amyloid plaques in the brain of a subject.

In any of the methods described herein, the repressor of the tau allele may be a ZFP-TF, for example a fusion protein comprising a ZFP that binds specifically to a tau allele and a transcriptional repression domain (e.g., KOX, KRAB, etc.). In other embodiments, the repressor of the tau allele may be a TALE-TF, for example a fusion protein comprising a TALE polypeptide that binds specifically to a tau allele and a transcriptional repression domain (e.g., KOX, KRAB, etc.). In some embodiments, the tau allele repressor is a CRISPR/Cas-TF where the nuclease domains in the Cas protein have been inactivated such that the protein no longer cleaves DNA. The resultant Cas RNA-guided DNA binding domain is fused to a transcription repressor (e.g. KOX, KRAB etc.) to repress the tau allele.

In some embodiments, the sequence encoding a genetic modulator (genetic repressor) as described herein (e.g., ZFP-TF, TALE-TF or CRISPR/Cas-TF) is inserted (integrated) into the genome while in other embodiments the sequence encoding the repressor is maintained episomally. In some instances, the nucleic acid encoding the TF fusion is inserted (e.g., via nuclease-mediated integration) at a safe harbor site comprising a promoter such that the endogenous promoter drives expression. In other embodiments, the repressor (TF) donor sequence is inserted (via nuclease-mediated integration) into a safe harbor site and the donor sequence comprises a promoter that drives expression of the repressor. In some embodiments, the sequence encoding the genetic modulator is maintained extrachromosomally (episomally) after delivery, and may include a heterologous promoter. The promoter may be a constitutive or inducible promoter. In some embodiments, the promoter sequence is broadly expressed while in other embodiments, the promoter is tissue or cell/type specific. In preferred embodiments, the promoter sequence is specific for neuronal cells. In especially preferred embodiments, the promoter chosen is characterized in that it has low expression. Non-limiting examples of preferred promoters include the neural specific promoters NSE, Synapsin, CAMKiia and MECPs. Non-limiting examples of ubiquitous promoters include CAS and Ubc. Further embodiments include the use of self-regulating promoters as described in U.S. Patent Publication No. 2015/0267205.

In still further embodiments, the repressor may comprise a nuclease (e.g., ZFN, TALEN and/or CRISPR/Cas system) that represses the tau allele by cleaving and thereby inactivating the tau allele. In certain embodiments, the nuclease introduces an insertion and/or deletion ("indel") via non-homologous end joining (NHEJ) following cleavage by the nuclease. In other embodiments, the nuclease introduces a donor sequence (by homology or non-homology directed methods), in which the donor integration inactivates the tau allele.

In any of the methods described herein, the repressor may be delivered to the subject (e.g., brain) as a protein, polynucleotide or any combination of protein and polynucleotide. In certain embodiments, the repressor(s) is(are) delivered using an AAV vector. In other embodiments, at least one component of the repressor (e.g., sgRNA of a CRISPR/Cas system) is delivered as in RNA form. In other embodiments, the repressor(s) is(are) delivered using a combination of any of the expression constructs described herein, for example one repressor (or portion thereof) on one expression construct (AAV9) and one repressor (or portion thereof) on a separate expression construct (AAV or other viral or non-viral construct).

Furthermore, in any of the methods described herein, the repressors can be delivered at any concentration (dose) that provides the desired effect. In preferred embodiments, the repressor is delivered using an adeno-associated virus (AAV) vector at 10,000-500,000 vector genome/cell (or any value therebetween). In certain embodiments, the repressor is delivered using a lentiviral vector at MOI between 250 and 1,000 (or any value therebetween). In other embodiments, the repressor is delivered using a plasmid vector at 0.01-1,000 ng/100,000 cells (or any value therebetween). In other embodiments, the repressor is delivered as mRNA at 150-1,500 ng/100,000 cells (or any value therebetween).

In any of the methods described herein, the method can yield about 50% or greater, 55% or greater, 60% or greater, 65% or greater, about 70% or greater, about 75% or greater, about 85% or greater, about 90% or greater, about 92% or greater, or about 95% or greater repression of the tau alleles in one or more AD neurons of the subject.

In further aspects, the tau-modulating transcription factors as described herein, such as a tau-modulating transcription factors comprising one or more of a zinc finger protein (ZFP TFs), a TALEs (TALE-TF), and a CRISPR/Cas-TFs for example, ZFP-TFs, TALE-TFs or CRISPR/Cas-TFs are used to repress expression of a mutant or wild type tau allele in of the brain (e.g., neuron) of a subject. The repression can be about 50% or greater, 55% or greater, 60% or greater, 65% or greater, 70% or greater, about 75% or greater, about 85% or greater, about 90% or greater, about 92% or greater, or about 95% or greater repression of the tau alleles in the one or more neurons of the subject as compared to untreated (wild-type) neurons of the subject. In certain embodiments, the tau-modulating transcription factor can be used to achieve one or more of the methods described herein.

Also provided is a kit comprising one or more of the AAV tau-modulators (e.g., repressors) and/or polynucleotides comprising components of and/or encoding the tau-modulators (or components thereof) as described herein. The kits may further comprise cells (e.g., neurons), reagents (e.g., for detecting and/or quantifying tau protein, for example in CSF) and/or instructions for use, including the methods as described herein.

BRIEF DESCRIPTION OF THE DRAWINGS

FIGS. 1A through 1D depict MAPT expression following introduction of engineered MAPT genetic modulators as described herein. FIG. 1A is a schematic showing the target sites within the MAPT gene for the DNA-binding molecule of the genetic modulator. The modulator for these experiments was a repressor. FIG. 1B shows graphs showing MAPT expression 24 hours after administration of the indicated amounts of MAPT repressor (52322, 52364, 52366, 52389, 57880, 57890 and 52288) or GFP or mock controls in mRNA form (at the indicated doses of 1000 ng, 300 ng, 100 ng, 30, ng, 10 ng or 3 ng, left to right respectively) to Neuro 2A cells. FIG. 1C depicts graphs showing MAPT expression 7 days after administration of the MAPT repressor (52322, 52364, 52366, 52389, 57880, 57890 and 52288) or GFP or mock controls using an AAV9 vector (with CMV promoter) at the indicated doses of $3\times10^5$ vg/cell, $1\times10^5$ vg/cell, $3\times10^4$ vg/cell, $1\times10^4$ vg/cell to primary mouse cortical neurons (MCNs). FIG. 1D shows graphs depicting Tau (MAPT) repression and off-target repression by 57880 and two exemplary derivatives (65887 and 65888) comprising mutations in the phosphate contacts in the ZFP backbone.

FIG. 2A is a Western Blot showing proteins levels of the indicated proteins at the indicated AAV9 dosages. FIG. 2B and FIG. 2C are graphs showing the proportion of tau/GAPDH proteins (top panels) and ZFP/GAPDH (bottom panels) at the indicated dosages of AAV9-52389 or mock (M).

FIGS. 5A and 5B show results of microarray analysis results of the indicated repressors (52322, 52364, 52366, 52389, 57880, 57890). FIG. 5A shows results 7 days after administration to mouse cortical neurons of the repressors carried by an AAV vector (AAV) at $1\times10^5$ vg/cell. Results are discussed in Example 3. The numbers above each graph represent the number of genes whose expression increased (up arrow) or decreased (repression) (down arrow). FIG. 5B shows the microarray analysis results comparing two repressors 57880 and 65888 with identical helices. The data for the 57880 protein is shown on the top row while the data for the 65888 protein is shown on the bottom row. 65888 has some potential phosphate contacts removed from the zinc finger backbone (see Table 2) and the data demonstrates a substantial increase in specificity in the 65888 protein (57880 upregulated 75 genes and repressed 110 gene in these experimental conditions while 65888 upregulated 3 genes and repressed 4, including tau) while maintaining similar tau repression activity in mouse cortical neurons.

FIGS. 6A and 6B are graphs depicting mRNA expression in cells using genetic repressors carried by AAV vector (AAV9) where expression of the repressor is driven by the indicated promoter (CMV, synapsin (SYN1), alpha-calcium/calmodulin-dependent protein kinase promoter (CamKII), and a 229 bp fragment of the methyl CpG-binding protein 2 promoter (MeCP2). FIG. 6A shows expression in MCNs. FIG. 6B shows expression in primary hippocampal neurons.

FIGS. 7A through 7D show mRNA (human tau and ZFP) levels in human iPSC-derived neurons. FIG. 7A is a schematic showing partial sequence of human and mouse MAPT target sites (SEQ ID NO:31 32, and 48-51, respectively, from left to right). FIG. 7B shows graphs showing mRNA expression in the iPSCs 18 days after administration of the indicated repressors carried by an AAV vector at the indicated dosages. FIG. 7C shows graphs showing mRNA expression in the iPSCs 18 days after administration of the indicated repressor (52366) carried by an AAV vector with the indicated promoters. FIG. 7D is a series of microarray plots using exemplary ZFP TFs in the human iPSC-derived neurons, and indicates that the ZFP TFs are highly specific. The cells were exposed to 1E5 of AAV6 comprising the ZFP-TF donor for 19 days prior to analysis.

FIGS. 8A through 8I1 show efficient neuronal transduction of ZFP-TFs and in vivo effects on mRNA (tau and ZFP) expression in mouse subjects using various AAV vectors to deliver the tau repressors. See, Example 6. FIG. 8A shows efficient transduction of the motor cortex (top panels), hippocampus (middle panels) and cerebellum (bottom panels) following AAV administration either IV (right panels) or ICV (left panels). FIG. 8B shows potent tau reduction (~50-70% reduction) via both ICV and IV administration of key tauopathy regions, including motor cortex (left panel, top row), brainstem (right panel, top row) and hippocampus (bottom left panel). FIG. 8C shows tau mRNA reduction (~40-70% reduction) throughout the brain and spinal cord following IV or ICV administration of AAV-ZFP-TF vectors. FIG. 8D shows levels of tau (MAPT) mRNA and FIG. 8E shows levels of the repressor (ZFP) mRNA for each hippocampal section. FIG. 8F are graphs depicting robust repression of tau throughout the CNS and spinal cord following administration of the tau repressors described herein (left panel shows 52389 repressor and right panel shows 57890 repressor) using AAV vectors. FIG. 8H are graphs showing total mouse tau protein levels in CSF (top row, left panel), cortex (top row, right panel) and hippocampus (top row, far right graph) of animals receiving the indicated compositions ("VEH" refers to control animals administered vehicle only; "172V" refers to animals receiving the irrelevant control ZFP-TF that does not bind to MAPT carried on AAV vector; "389V" refers to the 52389 repressor carried on an AAV construct; and "890V" refers to the 57890 repressor described herein carried on an AAV construct). Also shown (bottom row) is the statistically analysis showing the correlation between CSF and the levels in the cortex (right panel) and hippocampus (left panel).

FIGS. 9A through 9D depict further analysis of in vivo modulation (repression) of MAPT using statistical analysis as described in Example 6. FIG. 9A shows ANOVA followed by Sidak's post-test analyses for all slices (top panel shows tau, bottom panel shows ZFP). FIG. 9B shows average maximal tau reduction (top panel shows tau, bottom panel shows ZFP). FIG. 9C shows a high correlation between MAPT and ZFP-TF levels in animals treated with the 52322 MAPT repressor. FIG. 9D shows a high correlation between MAPT and ZFP-TF levels in animals treated with the 52389 MAPT repressor.

FIG. 10A shows the expression of tau 6 weeks after injection and demonstrates a decrease in all animals that received the ZFP-TF, regardless of promoter chosen. Asterisks indicate significance of the signal as compared to the PBS control (p<0.0001 for all promoters). FIG. 10B shows the expression of the ZFP-TF from the various promoters where highest ZFP-TF expression was detected in the animals treated with the CAMKII driven vector. The presence of activated astrocytes was measured for each treatment group (FIG. 10C) through detection of GFAP. In this experiment, the MeCP2 promoter resulted in no GFAP elevation compared to PBS-injected animals, SYN1 resulted in 4.0-fold higher GFAP levels (P<0.0001), CMV resulting in 3.2-fold higher levels (P<0.01), and CAMKII resulted in levels 2.4-fold higher (P<0.05). Similarly, the presence of microglia was also determined (FIG. 10D) in the treatment groups where the MeCP2 promoter resulted in no significant changes in IBA1 levels compared to PBS-injected animals, SYN1 resulted in 4.7-fold higher IBA1 levels (P<0.0001), CMV resulting in 3.0-fold higher levels (P<0.05), and CAMKII resulted in levels 3.2-fold higher (P<0.001).

FIGS. 12A through 12F depict the histological demonstrations of tau reduction in the hippocampus and connected brain regions. AAVs comprising the tau-specific ZFP-TF driven by the CMV promoter were delivered to the hippocampus to valuate endogenous tau protein reduction by immunofluorescent staining. The ZFP-TFs were linked to a fluorescent protein Venus for detection, and animals were sacrificed 6 weeks following injection. FIG. 12A is a cross section of the hippocampus and delineates 4 boxed regions for closer study. FIG. 12B is a close up of Box 1 from FIG. 12A and shows GFP/DAPI staining (left panel); GFP/tau/DAPI (middle panel) and tau (right panel). FIG. 12C is a graph of fluorescence intensity across Box 1, demonstrating a reduction in tau in the ipsilateral side of the section (right panel). FIG. 12D shows a close up of Box 2, while FIG. 12E is a close up of Box 3, demonstrating a decrease in tau staining on the ipsilateral side (right panel). FIG. 12F shows Box 4 where the top panel shows GFP (indication of ZFP-TF) signal in the ipsilateral side of the injection with a concomitant decrease in tau staining (lower panel). The lower middle panel also shows a graphical depiction of the decrease in tau staining. The lower left and right panels show staining in ipsilateral (left) and contralateral (right) sections. The data are discussed in greater detail in the Examples.

FIGS. 13A through 13J demonstrate the safety and sustained expression of the ZFP-TF for six months in the hippocampus in vivo. FIG. 13A depicts the signal for transduced cells in the hippocampus as a whole at the 6-week time point, indicating the expression of the ZFP-TF and GFP alone vectors are nearly the same. FIG. 13B shows similar results specifically for astrocytes while FIG. 13C shows the results for the microglia. FIG. 13D shows the transduction data similar to FIG. 13A, except for the 6-month time point. Similarly, FIG. 13E shows the astrocyte data for the 6-month time point and FIG. 13F shows the microglia data for the 6-month time point. FIG. 13G demonstrates that the mean thickness of a region of the hippocampus is maintained in the various treatment groups, demonstrating no overt neuronal toxicity from long-term expression of the ZFP-TF. FIG. 13H shows the coverage of the injections in the anterior (left panel) and posterior (right panel) hippocampus. The data are discussed in greater detail in the Examples. FIG. 13I are graphs showing normalized expression levels in subjects treated with the indicated ZFs (tau in top left, ZFs in top middle, VG/cell in top right GFPA (glial fibrillary acid protein, a marker for astrocytes) in bottom left, IBA1 (ionized calcium-binding adapter molecule 1, a marker of microglia) in bottom middle, and NeuN (a well-recognized marker of post-mitotic neurons that is highly conserved among different species, (Wang et al., (2015) Sci Reports 5:17383, doi 10.1038/srep17383)) in bottom right). FIG. 13J are graphs showing normalized expression levels of the indicated proteins in subjects treated with the indicated compositions ("PBS" refers to no tau modulator; "89V 6 weeks" refers to mice treated with the 52389 Venus construct sampled at 6 weeks, and "89V 11m" refers to 52389 Venus construct sampled at 11 months (tau, ZFP, GFAP, IBA1 from left to right in top panels; NeuN, MAP1, MAP1A, MAP2 from left to right in bottom panels).

FIGS. 14A through 14F are micrographs of brain sections of APP/PS1 mice treated with the ZFP-TFs. In these images, GFP is green in color, RFP is red in color and antibodies specific for Aβ are labeled with a secondary antibody (blue). FIGS. 14A and 14C are images of a wild type cortex (CTX) where the left CTX was treated with the irrelevant ZFP-TF (FIG. 14A) and the right CTX was treated with AAV encoding the fluorescent protein tRFP (FIG. 14C). FIGS. 14B and 14D are images of brain cortexes from APP/PS1 mice, where the left CTX was treated with the AAV encoding the tau-specific ZFP-TF ("389dV", FIG. 14B) or AAV encoding the tRFP (FIG. 14D). The images illustrate a reduction in dystrophic neurites (identifiable as punctate staining around the Aβ plaques and indicated by arrows) in the CTX treated with the tau-specific ZFP-TF. FIGS. 14E and 14F are higher magnification images of two examples of the APP/PS1 CTX sections treated either with the tau-specific ZFP-TF (FIG. 14E) or the tRFP (FIG. 14F) where there are more dystrophic neurites (indicated by arrows) in the tRFP treated section than the 389 ZFP-TF treated section.

DETAILED DESCRIPTION

Figure 1D:
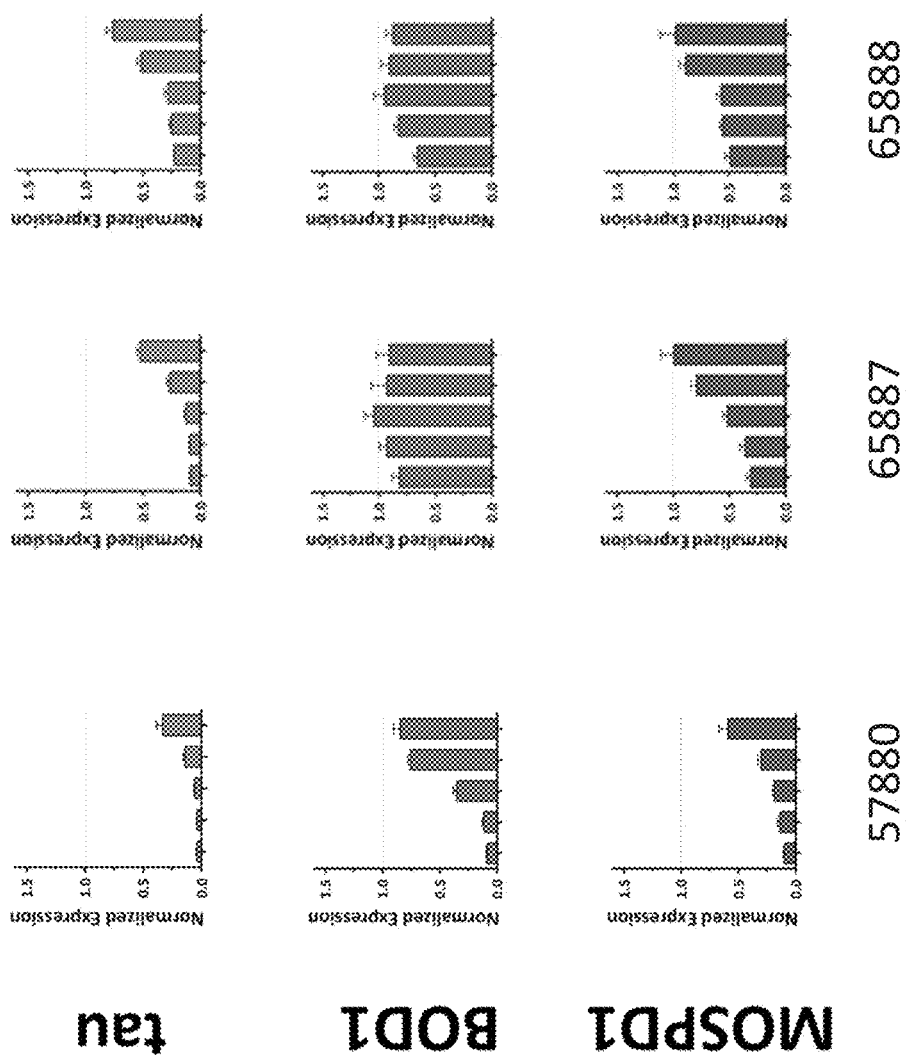

Disclosed herein are compositions and methods for the prevention and/or treatment of tauopathies. In particular, the compositions and methods described herein are used to repress the expression of a MAPT (tau) protein to prevent or treat tauopathies such as Alzheimer's Disease (AD), Frontotemporal Dementia, Progressive Supranuclear Palsy, seizure disorders and/or Corticobasal Degeneration. The MAPT repressors (e.g., MAPT-modulating transcription factors, such as MAPT-modulating transcription factors comprising zinc finger proteins (ZFP TFs), TALEs (TALE-TF), and/or CRISPR/Cas-TFs), modify the CNS such that the effects and/or symptoms of the tauopathy is reduced or eliminated, for example by reducing the aggregation of tau in the brain of a subject with a tauopathy (e.g., AD) and reducing the occurrence of neural tangles. In preferred embodiments, the MAPT-modulating transcription factors are delivered to the brain by a viral vector such as an AAV. AAV has been shown to be well suited for brain delivery, so use of these viral vectors to deliver MAPT modulating transcription factors is especially useful for the treatment of diseases such as Alzheimer's Disease associated with the inappropriate expression and thereby aggregation of tau protein.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of 10' or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

"TtAgo" is a prokaryotic Argonaute protein thought to be involved in gene silencing. TtAgo is derived from the bacteria *Thermus thermophilus*. See, e.g., Swarts et al., (2014) Nature 507(7491):258-261, G. Sheng et al., (2014) Proc. Natl. Acad. Sci. U.S.A. 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

DNA-binding domains such as sgRNAs, zinc finger binding domains or TALE DNA binding domains can be "engineered" to bind to a predetermined nucleotide sequence, for example via design of a sgRNA that binds to a selected target site or by engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering DNA-binding domains are design and selection. A "designed" zinc finger protein or TALE is a protein not occurring in nature whose design/composition results principally from rational criteria. Rational criteria for design include application of substitution rules and computerized algorithms for processing information in a database storing information of existing ZFP designs and binding data. A "selected" zinc finger protein or TALE is a protein not found in nature whose production results primarily from an empirical process such as phage display, interaction trap or hybrid selection. See, for example, U.S. Pat. Nos. 8,586,526; 6,140,081; 6,453,242; 6,746,838; 7,241,573; 6,866,997; 7,241,574; and 6,534,261; see also International Patent Publication No. WO 03/016496.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain", (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "genetic modulator" refers to any molecule that alters the expression and/or sequence of one or more genes. Non-limiting examples of genetic modulators include transcription factors (such as artificial transcription factors as described herein) that bind to the target gene and alter its expression and nucleases that modify the sequence of the target gene, which in turn alters its expression (e.g., inactivation of the target via insertions and/or deletions). Thus, a genetic modulator may be a genetic repressor (that represses and/or inactivates gene expression) or a genetic activator.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion molecule in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site. With respect to a fusion molecule in which a Cas DNA-binding domain (e.g., single guide RNA) is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al., (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Tau and Alzheimer's Disease

The tau protein is encoded by the MAPT gene which comprises 16 exons. Interestingly, exons 1, 4, 5, 7, 9, 11 and 12 are constitutively expressed whereas exons 2, 3, and 10 can be present in tau protein species derived from alternatively spliced variants, leading to the presence of six different tau protein isoforms in the adult brain. Tau binds to microtubules via 3 or 4 repeated tubulin-binding motifs in the C-terminal half of the protein, and is thought to stabilize the tubules where tau4R (4 tubulin binding motifs) is thought to interact more strongly with microtubules that tau3R. The ratio of 3R to 4R is generally stable but can be affected in pathological states. The tau form that interacts with microtubules is phosphorylated and it appears that hyperphosphorylation causes the tau to detach from microtubules. Hyperphosphoylated tau can be sequestered in the cell, which then leads to conformational changes in the protein and to aggregation. These aggregates may be the initial step in the formation of pathogenic neurofibrillary tangles (NFTs), however, hyperphosphorylated tau may be pathogenic in a soluble form as well as when present in the tangles (Bodea et al., (2016) *J of Neurochem* 138 (Suppl 1): 71-94). NFTs are restricted to the entorhinal cortex and medial temporal lobe in the early stages of AD, and by the time of severe clinical symptoms of the disease present, NFTs are widespread throughout the brain. Coincident with the presence of abundant NFTs, widespread distribution of amyloid plaques also occurs. In fact, it appears that the amyloid deposition in the cortex leads to an increase in the speed of tau propagation and the spread of NFT to distal regions of the brain. As tau tangles spread, there is a concomitant increase in neuronal loss (Pooler et al., (2015) *Acta Neuropathol Commun* 3:14, doi:10.1186/s40478-015-0199-x).

Tau has 95 amino acid residues that are capable of being phosphorylated, and several kinases have been identified that may be responsible for tau phosphorylation, which may be possible target candidates for new therapeutics, including glycogen synthase-3, cyclin-dependent kinase 5, members of the MAPK family, extracellular-regulated kinase, c-Jun N-terminal kinase and microtubule-affinity regulating kinase (Bodea (2016) ibid).

Amyloid β protein (Aβ) is the major constituent of senile plaques, which together with NFTs, are the hallmarks of a neuropathological confirmation of Alzheimer's Disease. Aβ is a peptide that has between 39 and 42 amino acid chains; the 42 amino acids form aggregates more avidly and is thought to be implicated in the pathogenesis of the disease and is the basis of the amyloid hypothesis (the proposal that accumulation of Aβ in the brain is the primary cause of AD, see review Hardy and Selkoe (2002) *Science* 297:353). Aβs are products of the proteolytic cleavage of amyloid precursor protein (APP), a ubiquitous, glycosylated, sulfated, and phosphorylated integral membrane protein (Sorrentino et al., (2014) *FEBS Lett* 588:641-652). However, it is becoming clear that the pathogenesis leading to AD is extremely complex and that the pathogenesis of Aβ accumulation may play a role in abnormal tau behavior (Ando et al., (2016) *PLoS Genet* 12(3):e1005917.

Reduction of tau in the brain has been shown to improve the pathology of AD. Regulated suppression of a tau transgene expression in a murine AD model demonstrated a reduction of transgene associate tau aggregates and a decrease in the concentration of hyperphosphorylated tau and NFT. In fact, this work also showed a loss in overall NFT, indicating that the accumulation of NFT may be reversible (Polydoro et al., (2013) *J of Neurosci* 33(33): 13300-13311). Additionally, studies performed with an intracellular anti-tau antibody delivered via AAV directly through intrahippocampal administration demonstrated a reduction in insoluble tau species, NFT and a rescue of the hippocampal atrophy that is observed in the untreated mouse model (Liu et al., (2016) *J Neurosci* 36(49): 12425-12435).

DNA-Binding Domains

The methods described herein make use of compositions, for example tau-modulating transcription factors, comprising a DNA-binding domain that specifically binds to a target sequence in a tau (MATP) gene. Any polynucleotide or polypeptide DNA-binding domain can be used in the compositions and methods disclosed herein, for example DNA-binding proteins (e.g., ZFPs or TALEs) or DNA-binding polynucleotides (e.g., single guide RNAs). Thus, genetic modulators (repressors) of tau genes are described.

In certain embodiments, the tau-repressor, or DNA binding domain therein, comprises a zinc finger protein. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

Tau target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A ZFP can be operably associated (linked) to one or more transcriptional regulatory (e.g., repression domains) to form a ZF-TF (e.g., repressor). Methods and compositions can also be used to increase the specificity of a ZFP for its intended target relative to other unintended cleavage sites, known as off-target sites for example by mutations to the ZFP backbone as described in U.S. patent application Ser. No. 15/685,580. Thus, tau repressors described herein can comprise mutations in one or more of their DNA binding domain backbone regions and/or one or more mutations in their transcriptional regulatory domains. These ZFPs can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-3388; Dujon et al., (1989) *Gene* 82:115-118; Perler et al., (1994) *Nucleic Acids Res.* 22, 1125-1127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 31:2952-2962; Ashworth et al., (2006) *Nature* 441:656-659; Paques et al., (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remade et al., (1999) *EMBO Journal* 18 (18): 5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs or may be positioned between the ZFPs (attached to both ZFPs).

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein. In certain embodiments, the TALE DNA-binding protein comprises binds to 12, 13, 14, 15, 16, 17, 18, 19, 20 or more contiguous nucleotides of a tau target site as shown in Table 1 or 2 (SEQ ID NO:1 to 6 or 33). The RVDs of the TALE DNA-binding protein that binds to a tau target site may be naturally occurring or non-naturally occurring RVDs. See, U.S. Pat. Nos. 8,586,526 and 9,458,205.

The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et al., (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al., (1989) *Mol Gen Genet* 218: 127-136 and WO2010079430).

TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al., (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch et al., (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and NG binds to T. These DNA binding repeats have been assembled into proteins with new combinations and numbers of repeats, to make artificial transcription factors that are able to interact with new sequences. In addition, U.S. Pat. No. 8,586,526 and U.S. Patent Publication No. 2013/0196373, incorporated by reference in their entireties herein, describe TALEs with N-cap polypeptides, C-cap polypeptides (e.g., +63, +231 or +278) and/or novel (atypical) RVDs.

Exemplary TALE are described in U.S. Pat. Nos. 8,586, 526 and 9,458,205, incorporated by reference in their entireties.

In certain embodiments, the DNA binding domains include a dimerization and/or multimerization domain, for example a coiled-coil (CC) and dimerizing zinc finger (DZ). See, U.S. Patent Publication No. 2013/0253040.

In still further embodiments, the DNA-binding domain comprises a single-guide RNA of a CRISPR/Cas system, for example sgRNAs as disclosed in 20150056705.

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7.; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

Type II CRISPR systems have been found in many different bacteria. BLAST searches on publically available genomes by Fonfara et al., ((2013) *Nuc Acid Res* 42(4): 2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al., (2012) *Science* 337:816). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et al., ibid and Cong et al., (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam et al., *Stem Cells and Development* 22(4):595-610 (2013)) and has been useful for zebrafish embryo genomic editing in vivo (see Hwang et al., (2013) *Nature Biotechnology* 31 (3):227) with editing efficiencies similar to ZFNs and TALENs.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al., 2006. *Biol. Direct* 1: 7; Hale et al., 2008. *RNA*, 14: 2572-2579). RNA analysis indicates that CRISPR locus transcripts are cleaved within the repeat sequences to release ~60- to 70-nt RNA intermediates that contain individual invader targeting sequences and flanking repeat fragments (Tang et al., 2002. *Proc. Natl. Acad. Sci.* 99: 7536-7541; Tang et al., 2005. *Mol. Microbiol.* 55: 469-481; Lillestol et al., 2006. *Archaea* 2: 59-72; Brouns et al., 2008. *Science* 321: 960-964; Hale et al., 2008. *RNA*, 14: 2572-2579). In the archaeon *Pyrococcus furiosus*, these intermediate RNAs are further processed to abundant, stable ~35- to 45-nt mature psiRNAs (Hale et al., 2008. *RNA*, 14: 2572-2579).

The requirement of the crRNA-tracrRNA complex can be avoided by use of an engineered "single-guide RNA" (sgRNA) that comprises the hairpin normally formed by the annealing of the crRNA and the tracrRNA (see Jinek et al., (2012) *Science* 337:816 and Cong et al., (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et al., (2013) *Nature Biotechnology* 31 (3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In certain embodiments, the sgRNA comprises a sequence that binds to 12, 13, 14, 15, 16, 17, 18, 19, 20 or more contiguous nucleotides of a tau target site as shown in Table 1 or 2 (SEQ ID NO:1 to 6 or 33). In some embodiments, the RNAs comprise 22 bases of complementarity to a target and of the form G[n19], followed by a protospacer-adjacent motif (PAM) of the form NGG or NAG for use with a S. pyogenes CRISPR/Cas system. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et al., (2013) Nature Biotech doi:10.1038/nbt.2647). Tails may be of +67 to +85 nucleotides, or any number therebetween with a preferred length of +85 nucleotides. Truncated sgRNAs may also be used, "tru-gRNAs" (see Fu et al., (2014) Nature Biotech 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2013, ibid) using a S. pyogenes Cas9. Additional PAM sequences may also include those lacking the initial G (Sander and Joung (2014) Nature Biotech 32(4):347). In addition to the S. pyogenes encoded Cas9 PAM sequences, other PAM sequences can be used that are specific for Cas9 proteins from other bacterial sources. For example, the PAM sequences shown below (adapted from Sander and Joung, ibid, and Esvelt et al., (2013) Nat Meth 10(11):1116) are specific for these Cas9 proteins:

| Species | PAM |
|---|---|
| S. pyogenes | NGG |
| S. pyogenes | NAG |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a S. pyogenes CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-S. pyogenes bacteria, the same guidelines may be used where the alternate PAMs are substituted in for the S. pyogenes PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et al., (2014) Nature Biotech doi:10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In certain embodiments, the Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes (including safe harbor genes) are disclosed for example, in U.S. Publication No. 2015/0056705.

Thus, the nuclease comprises a DNA-binding domain in that specifically binds to a target site in any gene into which it is desired to insert a donor (transgene) in combination with a nuclease domain that cleaves DNA.

Tau Gene Modulators

The tau DNA-binding domains may be fused to or otherwise associate with any additional molecules (e.g., polypeptides) for use in the methods described herein. In certain embodiments, the methods employ fusion molecules comprising at least one DNA-binding molecule (e.g., ZFP, TALE or single guide RNA) and a heterologous regulatory (functional) domain (or functional fragment thereof).

In certain embodiments, the functional domain of the tau modulator comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. See, e.g., U.S. Publication No. 2013/0253040, incorporated by reference in its entirety herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, Neuroreport 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO* 18, 6439-6447). Additional exemplary activation domains include, Oct 1, Oct-2A, Sp1, AP-2, and CTF1 (Seipel et al., *EMBO* 111, 4961-4968 (1992) as well as p300, CBP, PCAF, SRC1 PvALF, AtHD2A and ERF-2. See, for example, Robyr et al., (2000) *Mol. Endocrinol.* 14:329-347; Collingwood et al., (1999) *J. Mol. Endocrinol.* 23:255-275; Leo et al., (2000) *Gene* 245:1-11; Manteuffel-Cymborowska (1999) *Acta Biochim. Pol.* 46:77-89; McKenna et al., (1999) *J. Steroid Biochem. Mol. Biol.* 69:3-12; Malik et al., (2000) *Trends Biochem. Sci.* 25:277-283; and Lemon et al., (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al., (2000) *Gene* 245:21-29; Okanami et al., (1996) *Genes Cells* 1:87-99; Goff et al., (1991) *Genes Dev.* 5:298-309; Cho et al., (1999) *Plant Mol. Biol.* 40:419-429; Ulmason et al., (1999) *Proc. Natl. Acad. Sci. USA* 96:5844-5849; Sprenger-Haussels et al., (2000) *Plant J.* 22:1-8; Gong et al., (1999) *Plant Mol. Biol.* 41:33-44; and Hobo et al., (1999) *Proc. Natl. Acad. Sci. USA* 96:15,348-15,353.

Exemplary repression domains that can be used to make tau repressors include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al., (1999) *Cell* 99:451-454; Tyler et al., (1999) *Cell* 99:443-446; Knoepfler et al., (1999) *Cell* 99:447-450; and Robertson et al., (2000) *Nature Genet.* 25:338-342. Additional exemplary repression domains include, but are not limited to, ROM2 and AtHD2A. See, for example, Chem et al., (1996) *Plant Cell* 8:305-321; and Wu et al., (2000) *Plant J.* 22:19-27.

In some instances, the domain is involved in epigenetic regulation of a chromosome. In some embodiments, the domain is a histone acetyltransferase (HAT), e.g. type-A, nuclear localized such as MYST family members MOZ, Ybf2/Sas3, MOF, and Tip60, GNAT family members Gcn5 or pCAF, the p300 family members CBP, p300 or Rtt109 (Berndsen and Denu (2008) *Curr Opin Struct Biol* 18(6): 682-689). In other instances the domain is a histone deacetylase (HDAC) such as the class I (HDAC-1, 2, 3, and 8), class II (HDAC IIA (HDAC-4, 5, 7 and 9), HDAC IIB (HDAC 6 and 10)), class IV (HDAC-11), class III (also known as sirtuins (SIRTs); SIRT1-7) (see Mottamal et al., (2015) *Molecules* 20(3):3898-3941). Another domain that is used in some embodiments is a histone phosphorylase or kinase, where examples include MSK1, MSK2, ATR, ATM, DNA-PK, Bub 1, VprBP, IKK-α, PKCβ1, Dik/Zip, JAK2, PKCS, WSTF and CK2. In some embodiments, a methylation domain is used and may be chosen from groups such as Ezh2, PRMT1/6, PRMTS/7, PRMT 2/6, CARM1, set?/9, MLL, ALL-1, Suv 39h, G9a, SETDB1, Ezh2, Set2, Dotl, PRMT 1/6, PRMT 5/7, PR-Set7 and Suv4-20h. Domains involved in sumoylation and biotinylation (Lys9, 13, 4, 18 and 12) may also be used in some embodiments (review see Kousarides (2007) *Cell* 128:693-705).

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al., (2000) *Proc. Natl. Acad. Sci. USA* 97:3930-3935. Likewise, CRISPR/Cas TFs and nucleases comprising a sgRNA nucleic acid component in association with a polypeptide component function domain are also known to those of skill in the art and detailed herein.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

In certain embodiments, the fusion molecule comprises a DNA-binding domain and a nuclease domain to create functional entities that are able to recognize their intended nucleic acid target through their engineered (ZFP or TALE or sgRNA) DNA binding domains and create nucleases (e.g., zinc finger nuclease or TALE nucleases or CRISPR/Cas nucleases) cause the DNA to be cut near the DNA binding site via the nuclease activity. This cleavage results in inactivation (repression) of a tau gene. Thus, tau repressors also include tau nucleases.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains, sgRNAs in association with nuclease domains) or, alternatively, the DNA-binding domain of a naturally-occurring nuclease may be altered to bind to a selected target site (e.g., a meganuclease that has been engineered to bind to site different than the cognate binding site).

The nuclease domain may be derived from any nuclease, for example any endonuclease or exonuclease. Non-limiting examples of suitable nuclease (cleavage) domains that may be fused to tau DNA-binding domains as described herein include domains from any restriction enzyme, for example a Type IIS Restriction Enzyme (e.g., FokI). In certain embodiments, the cleavage domains are cleavage half-domains that require dimerization for cleavage activity. See, e.g., U.S. Pat. Nos. 8,586,526; 8,409,861; and 7,888,121, incorporated by reference in their entireties herein. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing.

The nuclease domain may also be derived any meganuclease (homing endonuclease) domain with cleavage activity may also be used with the nucleases described herein, including but not limited to I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In certain embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al., (2013) *Nat Comm:* 1-8 DOI: 10.1038/ncomms2782).

In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:*42(4):2591-2601, doi: 10.1093/nar/gkt1224).

In addition, the nuclease domain of the meganuclease may also exhibit DNA-binding functionality. Any TALENs may be used in combination with additional TALENs (e.g., one or more TALENs (cTALENs or FokI-TALENs) with one or more mega-TALs) and/or ZFNs.

In addition, cleavage domains may include one or more alterations as compared to wild-type, for example for the formation of obligate heterodimers that reduce or eliminate off-target cleavage effects. See, e.g., U.S. Pat. Nos. 7,914,796; 8,034,598; and 8,623,618, incorporated by reference in their entireties herein.

Nucleases as described herein may generate double- or single-stranded breaks in a double-stranded target (e.g., gene). The generation of single-stranded breaks ("nicks") is described, for example in U.S. Pat. Nos. 8,703,489 and 9,200,266, incorporated herein by reference which describes how mutation of the catalytic domain of one of the nucleases domains results in a nickase.

Thus, a nuclease (cleavage) domain or cleavage half-domain can be any portion of a protein that retains cleavage activity, or that retains the ability to multimerize (e.g., dimerize) to form a functional cleavage domain.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Publication No. 2009/0111119. Nuclease expression constructs can be readily designed using methods known in the art.

Expression of the fusion proteins (or component thereof) may be under the control of a constitutive promoter or an inducible promoter, for example the galactokinase promoter which is activated (de-repressed) in the presence of raffinose and/or galactose and repressed in presence of glucose. Non-limiting examples of preferred promoters include the neural specific promoters NSE, Synapsin, CAMKiia and MECPs. Non-limiting examples of ubiquitous promoters include CAS and Ubc. Further embodiments include the use of self-regulating promoters (via the inclusion of high affinity binding sites for the tau DNA-binding domain) as described in U.S. Patent Publication No. 2015/0267205).

Delivery

The proteins and/or polynucleotides (e.g., tau modulators) and compositions comprising the proteins and/or polynucleotides described herein may be delivered to a target cell by any suitable means including, for example, by injection of proteins, via mRNA and/or using an expression construct (e.g., plasmid, lentiviral vector, AAV vector, Ad vector, etc.). In preferred embodiments, the repressor is delivered using an AAV vector, including but not limited to AAV9 (see U.S. Pat. No. 7,198,951), an AAV vector as described in U.S. Pat. No. 9,585,971 and/or an AAV vector as described in U.S. Provisional Patent Application No. 62/503,121.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences. Thus, when one or more tau modulators (e.g., repressors) are introduced into the cell, the sequences encoding the protein components and/or polynucleotide components may be carried on the same vector or on different vectors. When multiple vectors are used, each vector may comprise a sequence encoding one or multiple tau modulators (e.g., repressors) or components thereof. In preferred embodiments, the vector system is an AAV vector, for example AAV9 or an AAV variant described in U.S. Pat. No. 9,585,971 and/or U.S. Provisional Patent Application No. 62/503,121.

Conventional viral and non-viral based gene transfer methods can be used to introduce nucleic acids encoding engineered tau modulators in cells (e.g., mammalian cells) and target tissues. Such methods can also be used to administer nucleic acids encoding such repressors (or components thereof) to cells in vitro. In certain embodiments, nucleic acids encoding the repressors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al., (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); International Patent Publication NO. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV")

vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; International Patent Publication No. WO 93/24641; Kotin, Human Gene Therapy 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV 8.2, AAV9, and AAV rh10 and pseudotyped AAV such as AAV2/8, AAV2/5, AAV2/9 and AAV2/6 can also be used in accordance with the present invention. Novel AAV serotypes capable of crossing the blood-brain barrier can also be used in accordance with the present invention (see e.g. U.S. Pat. No. 9,585,971). In preferred embodiments, an AAV9 vector (including variants and pseudotypes of AAV9) is used.

Replication-deficient recombinant adenoviral vectors (Ad) can be produced at high titer and readily infect a number of different cell types. Most adenovirus vectors are engineered such that a transgene replaces the Ad Ela, Elb, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and w2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, intrathecal, intracisternal, intracerebroventricular, or intracranial infusion, including direct injection into the brain including into any region of the brain such as the hippocampus, cortex, striatum, etc.) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the compositions as described herein (e.g., polynucleotides and/or proteins) are delivered directly in vivo. The compositions (cells, polynucleotides and/or proteins) may be administered directly into the central nervous system (CNS), including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, subdermal, intrathecal, intracisternal, intracerebroventricular and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668 and 8,092,429, relating to delivery of compositions (including expression vectors) to the brain and U.S. Patent Publication No. 2006/0239966, incorporated herein by reference in their entireties.

The effective amount to be administered will vary from patient to patient and according to the mode of administration and site of administration. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. In certain embodiments, To deliver ZFPs using adeno-associated viral (AAV) vectors directly to the human brain, a dose range of $1\times10^{10}$-$5\times10^{15}$ (or any value therebetween) vector genome per striatum can be applied. As noted, dosages may be varied for other brain structures and for different delivery protocols. Methods of delivering AAV vectors directly to the brain are known in the art. See, e.g., U.S. Pat. Nos. 9,089,667; 9,050,299; 8,337,458; 8,309,355; 7,182,944; 6,953,575; and 6,309,634.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with at least one tau modulator (e.g., repressor) or component thereof and re-infused back into the subject organism (e.g., patient). In a preferred embodiment, one or more nucleic acids of the tau modulator (e.g., repressor) are delivered using AAV9. In other embodiments, one or more nucleic acids of the tau modulator (e.g., repressor) are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Pat. No. 8,597,912) in the stem cells, or those that are disrupted in a caspase, again using caspase-6 specific ZFNs for example. These cells can be transfected with the ZFP TFs or TALE TFs that are known to regulate a tau gene.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory et al., (1996) *Proc. Natl. Acad. Sci. USA* 93:11382-11388; Dull et al., (1998) *J. Virol.* 72:8463-8471; Zuffery et al., (1998) *J. Virol.* 72:9873-9880; Follenzi et al., (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used. In a preferred embodiment, the methods and composition are delivered directly to a brain cell, for example in the striatum.

Models of CNS Disorders

Studies of CNS disorders can be carried out in animal model systems such as non-human primates (e.g., Parkinson's Disease (Johnston and Fox (2015) *Curr Top Behav Neurosci* 22: 221-35); Amyotrophic lateral sclerosis (Jackson et al., (2015) *J. Med Primatol:* 44(2):66-75), Huntington's Disease (Yang et al., (2008) *Nature* 453(7197):921-4); Alzheimer's Disease (Park et al., (2015) *Int J Mol Sci* 16(2):2386-402); Seizure (Hsiao et al., (2016) *E Bio Med* 9:257-77), canines (e.g. MPS VII (Gurda et al., (2016) *Mol Ther* 24(2):206-216); Alzheimer's Disease (Schutt et al., (2016) *J Alzheimers Dis* 52(2):433-49); Seizure (Varatharajah et al., (2017) *Int J Neural Syst* 27(1):1650046) and mice (e.g. Seizure (Kadiyala et al., (2015) *Epilepsy Res* 109:183-96); Alzheimer's Disease (Li et al., (2015) *J Alzheimers Dis Parkin* 5(3) doi 10:4172/2161-0460), (review: Webster et al., (2014) *Front Genet* 5 art 88, doi:10.3389f/gene.2014.00088). These models may be used even when there is no animal model that completely recapitulates a CNS disease as they may be useful for investigating specific symptom sets of a disease. The models may be helpful in determining efficacy and safety profiles of a therapeutic methods and compositions (genetic repressors) described herein.

Applications

Tau modulators (e.g., tau repressors) as described herein comprising MAPT-binding molecules (e.g., ZFPs, TALEs, CRISPR/Cas systems, Ttago, etc.) as described herein, and the nucleic acids encoding them, can be used for a variety of applications. These applications include therapeutic methods in which a MAPT-binding molecule (including a nucleic acid encoding a DNA-binding protein) is administered to a subject using a viral (e.g., AAV) or non-viral vector and used to modulate the expression of a target gene within the subject. The modulation can be in the form of repression, for example, repression of tau expression that is contributing to an AD disease state. Alternatively, the modulation can be in the form of activation when activation of expression or increased expression of an endogenous cellular gene can ameliorate a diseased state. In still further embodiments, the modulation can be repression via cleavage (e.g., by one or more nucleases), for example, for inactivation of a MAPT gene. As noted above, for such applications, the MAPT-binding molecules, or more typically, nucleic acids encoding them are formulated with a pharmaceutically acceptable carrier as a pharmaceutical composition.

The MAPT-binding molecules, or vectors encoding them, alone or in combination with other suitable components (e.g. liposomes, nanoparticles or other components known in the art), can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically, retro-orbitally (RO), intracranially (e.g., to any area of the brain including but not limited to the hippocampus and/or cortex) or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and $K_d$ of the particular MAPT-binding molecule employed, the target cell, and the condition of the patient, as well as the body weight or surface area of the patient to be treated. The size of the dose also is determined by the existence, nature, and extent of any adverse side-effects that accompany the administration of a particular compound or vector in a particular patient The following Examples relate to exemplary embodiments of the present disclosure in which the MAPT-modulator comprises a zinc finger protein. It will be appreciated that this is for purposes of exemplification only and that other MAPT-modulators (e.g., repressors) can be used, including, but not limited to, TALE-TFs, a CRISPR/Cas system, additional ZFPs, ZFNs, TALENs, additional CRISPR/Cas systems, homing endonucleases (meganucleases) with engineered DNA-binding domains. It will be apparent that these modulators can be readily obtained using methods known to the skilled artisan to bind to the target sites as exemplified below. Similarly, the following Examples relate to exemplary embodiments in which the delivery vehicle is any AAV vector but it will apparent that any viral (Ad, LV, etc.) or non-viral (plasmid, mRNA, etc.) can be used to deliver the tau repressors described herein.

EXAMPLES

Example 1: MAPT Repressors

A screen of approximately 185 zinc finger proteins engineered essentially as described in U.S. Pat. No. 6,534,261; U.S. Patent Publication Nos. 2015/0056705; 2011/0082093; 2013/0253040; and 2015/0335708 was performed and the ZFPs bound to their MAPT target sites. Zinc finger proteins 52288, 52322, 52364, 52366, 52389, 57880, 57890 and 65888 (see Tables 1 through 3 below) targeted to mouse MAPT were selected for further study. The phosphate contact mutants listed for 65888 are as previously described (see e.g. U.S. patent application Ser. No. 15/685,580). Table 1 shows the recognition helices of the DNA binding domain of these ZFPs, and the target sequences of these ZFPs. A set of ZFPs were also made to target MAPT sequences shared between the mouse and human genes. These are shown in Table 2. Table 3 shows parent and derivative ZFP TFs where the ZFP backbone has been mutated at the indicated locations to remove potential non-specific phosphate contacts. The ZFPs were evaluated by standard SELEX analysis and shown to bind to their target sites.

TABLE 1 mouse MAPT-specific repressor designs

| SBS #, Target | Design | | | | | |
|---|---|---|---|---|---|---|
| | F1 | F2 | F3 | F4 | F5 | F6 |
| SBS#52364 cgACAGAAGGCGAG gacagaagaggaca (SEQ ID NO: 1) | RSDNLAR (SEQ ID NO: 7) | DRSHLAR (SEQ ID NO: 8) | QSGNLAR (SEQ ID NO: 9) | QSNTRIM (SEQ ID NO: 10) | N/A | N/A |
| SBS#52389 ccGTTGCGCCTGAT tGATGCCcagctcc (SEQ ID NO: 2) | ERGTLAR (SEQ ID NO: 11) | TSANLSR (SEQ ID NO: 12) | TSGNLTR (SEQ ID NO: 13) | HRTSLTD (SEQ ID NO: 14) | RSHSLLR (SEQ ID NO: 15) | HPSARKR (SEQ ID NO: 16) |
| SBS#52322 gtGGCGGAGACTGA GAGcgcgcgcggcc (SEQ ID NO: 3) | RSANLTR (SEQ ID NO: 17) | DSSHLEL (SEQ ID NO: 18) | DRSNLTR (SEQ ID NO: 19) | DRSHLTR (SEQ ID NO: 20) | DRSHLAR (SEQ ID NO: 8) | N/A |
| SBS#57930 cgGCAGAAGGTGGG cGGTGGCggcggcg (SEQ ID NO: 44) | DRSHLTR (SEQ ID NO: 20) | LKQHLTR (SEQ ID NO: 37) | RSAHLSR (SEQ ID NO: 25) | TSGHLSR (SEQ ID NO: 26) | QSGNLAR (SEQ ID NO: 9) | QSGDLTR (SEQ ID NO: 35) |
| SBS#57947 gcGGCGGCgGCAGA AGGTGGGcggtggC (SEQ ID NO: 45) | RSAHLSR (SEQ ID NO: 25) | TSGHLSR (SEQ ID NO: 26) | QSGNLAR (SEQ ID NO: 9) | QSGDLTR (SEQ ID NO: 35) | DRSHLSR (SEQ ID NO: 38) | DRSHLAR (SEQ ID NO: 8) |

TABLE 2 human/mouse MAPT-specific repressor designs

| SBS #, Target | Design | | | | | |
|---|---|---|---|---|---|---|
| | F1 | F2 | F3 | F4 | F5 | F6 |
| SBS#52366 ctTCTGTCGATTAT CAGgtaagcgccgc (SEQ ID NO: 4) | RSDNLSE (SEQ ID NO: 21) | TSSNRKT (SEQ ID NO: 22) | TSGNLTR (SEQ ID NO: 13) | DRSALAR (SEQ ID NO: 23) | RNSDRTK (SEQ ID NO: 24) | N/A |
| SBS#57880 ctGGTGGGtGGCGG AGACTGAgagcgcg (SEQ ID NO: 5) | DSSHLEL (SEQ ID NO: 18) | DRSNLTR (SEQ ID NO: 19) | DRSHLTR (SEQ ID NO: 20) | DRSHLAR (SEQ ID NO: 8) | RSAHLSR (SEQ ID NO: 25) | TSGHLSR (SEQ ID NO: 26) |
| SBS#57890 tgGTGCTGGAGCTG GTGGGTggcggaga (SEQ ID NO: 6) | LRHHLTR (SEQ ID NO: 27) | RRFTLSK (SEQ ID NO: 28) | RSDVLSE (SEQ ID NO: 29) | KHSTRRV (SEQ ID NO: 30) | RSDVLSE (SEQ ID NO: 29) | RLYTLHK (SEQ ID NO: 30) |
| SBS#52288 agGGGCGGGCAGCG aggcctgggcgggc (SEQ ID NO: 33) | RSADLTR (SEQ ID NO: 34) | QSGDLTR (SEQ ID NO: 35) | RSDHLSE (SEQ ID NO: 36) | RSAHLSR (SEQ ID NO: 25) | N/A | N/A |
| SBS#65976 ctCCAGAAGGGGAT CATGACctcctcac (SEQ ID NO: 46) | DRSNLSR (SEQ ID NO: 39) | LRQNLIM (SEQ ID NO: 40) | TSANLTV (SEQ ID NO: 41) | RSDHLSR (SEQ ID NO: 42) | QSGNLAR (SEQ ID NO: 9) | QRNDRKS (SEQ ID NO: 43) |
| 65976 Phos contact mutants | Qm5 | none | Qm5 | none | Qm5 | none |

ZFPs including one or more mutations in the backbone regions as described in U.S. patent application Ser. No. 15/685,580 (e.g., mutations at made at position (−5), (−9) and/or position (−14) relative to the DNA binding helix for example R or K to A, L, S, N, E, Y or Q) were also prepared (see, e.g., 65888, 57930, 65918, 65920, 65894, 57947, 65,968, 65887, 65860 and 65976 in Tables 1-3). All ZFPs described herein were operably linked to a KRAB repression domain to form ZFP-TFs and all repressed MAPT expression.

Exemplary ZFP TFs were transfected into mouse Neuro2a cells or primary mouse cortical neurons. After 24 hours, total RNA was extracted and the expression of MAPT and two reference genes (ATP5b, RPL38) was monitored using real-time RT-qPCR. As shown in FIG. 1, the ZFP-TFs were found to be effective in repressing MAPT expression with a diversity of dose-response and MAPT repression activity (see FIG. 1B).

ZFP-TF tau repressors were engineered that included mutations to the backbone region. Table 3 depicts exemplary ZFP-TF repressors (and their parent compounds). The results with these optimized ZFP TFs (e.g. exemplary results shown comparing 65888 to 57880) demonstrated dramatically improved specificity (by over 10-fold) without affecting activity in primary neurons (tau repression, see FIG. 1B). Further, two derivatives of the 57880 parent, 65887 and 65888, were tested in Neuro2A cells for repression activity for the BOD1 and MOSPD1 off targets (see FIG. 1D), where off-target repression by the proteins comprising phosphate contact mutations in the ZFP backbone were reduced. See, also, U.S. patent application Ser. No. 15/685,580.

TABLE 3

Optimized ZFP-TF designs

| SBS #, Target | Design | | | | | |
|---|---|---|---|---|---|---|
| | F1 | F2 | F3 | F4 | F5 | F6 |
| SBS# 57930 cgGCAGAAGGTGGG cGGTGGCggcggcg (SEQ ID NO: 44) [Parent] | DRSHLTR (SEQ ID NO: 20) | LKQHLTR (SEQ ID NO: 37) | RSAHLSR (SEQ ID NO: 25) | TSGHLSR (SEQ ID NO: 26) | QSGNLAR (SEQ ID NO: 9) | QSGDLTR (SEQ ID NO: 35) |
| SBS# 65918 cgGCAGAAGGTGGG cGGTGGCggcggcg (SEQ ID NO: 44) | DRSHLTR (SEQ ID NO: 20) | LKQHLTR (SEQ ID NO: 37) | RSAHLSR (SEQ ID NO: 25) | TSGHLSR (SEQ ID NO: 26) | QSGNLAR (SEQ ID NO: 9) | QSGDLTR (SEQ ID NO: 35) |
| 65918 Phos contact mutants | Qm5 | none | none | none | Qm5 | none |
| SBS# 65920 cgGCAGAAGGTGGG cGGTGGCggcggcg (SEQ ID NO: 44) | DRSHLTR (SEQ ID NO: 20) | LKQHLTR (SEQ ID NO: 37) | RSAHLSR (SEQ ID NO: 25) | TSGHLSR (SEQ ID NO: 26) | QSGNLAR (SEQ ID NO: 9) | QSGDLTR (SEQ ID NO: 35) |
| 65920 Phos contact mutants | Qm5 | none | Qm5 | none | Qm5 | none |
| SBS# 57890 tgGTGCTGGAGCTG GTGGGTggcggaga (SEQ ID NO: 6) [Parent] | LRHHLTR (SEQ ID NO: 27) | RRFTLSK (SEQ ID NO: 28) | RSDVLSE (SEQ ID NO: 29) | KHSTRRV (SEQ ID NO: 30) | RSDVLSE (SEQ ID NO: 29) | RLYTLHK (SEQ ID NO: 30) |
| SBS# 65894 tgGTGCTGGAGCTG GTGGGTggcggaga (SEQ ID NO: 6) | LRHHLTR (SEQ ID NO: 27) | RRFTLSK (SEQ ID NO: 28) | RSDVLSE (SEQ ID NO: 29) | KHSTRRV (SEQ ID NO: 30) | RSDVLSE (SEQ ID NO: 29) | RLYTLHK (SEQ ID NO: 30) |
| 65894 Phos contact mutants | Qm5 | none | none | none | Qm5 | none |
| SBS# 57947 gcGGCGGCgGCAGA AGGTGGGcggtggc (SEQ ID NO: 45) [parent] | RSAHLSR (SEQ ID NO: 25) | TSGHLSR (SEQ ID NO: 26) | QSGNLAR (SEQ ID NO: 9) | QSGDLTR (SEQ ID NO: 35) | DRSHLSR (SEQ ID NO: 38) | DRSHLAR (SEQ ID NO: 8) |
| SBS# 65968 gcGGCGGCgGCAGA AGGTGGGcggtggc (SEQ ID NO: 45) | RSAHLSR (SEQ ID NO: 25) | TSGHLSR (SEQ ID NO: 26) | QSGNLAR (SEQ ID NO: 9) | QSGDLTR (SEQ ID NO: 35) | DRSHLSR (SEQ ID NO: 38) | DRSHLAR (SEQ ID NO: 8) |
| 65968 Phos contact mutants | Qm5 | none | Qm5 | none | Qm5 | none |
| SBS# 57880 ctGGTGGGtGGCGG AGACTGAgagcgcg (SEQ ID NO: 5) [Parent] | DSSHLEL (SEQ ID NO: 18) | DRSNLTR (SEQ ID NO: 19) | DRSHLTR (SEQ ID NO: 20) | DRSHLAR (SEQ ID NO: 8) | RSAHLSR (SEQ ID NO: 25) | TSGHLSR (SEQ ID NO: 26) |

TABLE 3-continued

Optimized ZFP-TF designs

| SBS #, Target | Design | | | | | |
|---|---|---|---|---|---|---|
| | F1 | F2 | F3 | F4 | F5 | F6 |
| SBS# 65888 ctGGTGGGtGGCGG AGACTGAgagcgcg (SEQ ID NO: 5) | DSSHLEL (SEQ ID NO: 18) | DRSNLTR (SEQ ID NO: 19) | DRSHLTR (SEQ ID NO: 20) | DRSHLAR (SEQ ID NO: 8) | RSAHLSR (SEQ ID NO: 25) | TSGHLSR (SEQ ID NO: 26) |
| 65888 Phos contact mutants | Qm5 | none | Qm5 | none | Qm5 | none |
| SBS# 65887 ctGGTGGGtGGCGG AGACTGAgagcgcg (SEQ ID NO: 5) | DSSHLEL (SEQ ID NO: 18) | DRSNLTR (SEQ ID NO: 19) | DRSHLTR (SEQ ID NO: 20) | DRSHLAR (SEQ ID NO: 8) | RSAHLSR (SEQ ID NO: 25) | TSGHLSR (SEQ ID NO: 26) |
| 65887 Phos contact mutants | none | none | Qm5 | none | Qm5 | none |
| SBS# 52389 ccGTTGCGCCTGAT tGATGCCcagctcc (SEQ ID NO: 2) [Parent] | ERGTLAR (SEQ ID NO: 11) | TSANLSR (SEQ ID NO: 12) | TSGNLTR (SEQ ID NO: 13) | HRTSLTD (SEQ ID NO: 14) | RSHSLLR (SEQ ID NO: 15) | HPSARKR (SEQ ID NO: 16) |
| SBS# 65860 ccGTTGCGCCTGAT tGATGCCcagctcc (SEQ ID NO: 2) | ERGTLAR (SEQ ID NO: 11) | TSANLSR (SEQ ID NO: 12) | TSGNLTR (SEQ ID NO: 13) | HRTSLTD (SEQ ID NO: 14) | RSHSLLR (SEQ ID NO: 15) | HPSARKR (SEQ ID NO: 16) |
| 65860 Phos contact mutants | none | none | none | none | Qm5 | none |

Example 2: Tau Repression in Mouse Neurons

All ZFP repressors were cloned into rAAV2/9 vectors using a CMV promoter to drive expression. Virus was produced in HEK293T cells, purified using a CsCl density-gradient, and titered by real time qPCR according to methods known in the art. The purified virus was used to infect cultured primary mouse cortical neurons at 3E5, 1E5, 3E4, and 1E4 VG/cell. After 7 days, total RNA was extracted and the expression of MAPT and two reference genes (ATP5b, EIF4a2) was monitored using real-time RT-qPCR.

Figure 2C:
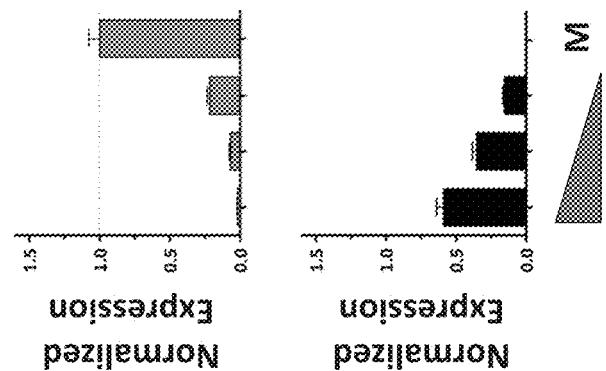
FIGS. 2A through 2C depict protein levels (tau, GAPDH and ZFP) in MCNs treated with the indicated repressor (52389) carried by an AAV9 vector.
Figure 2B:
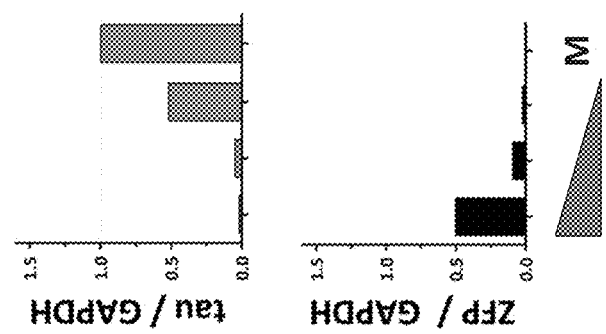
Figure 2A:
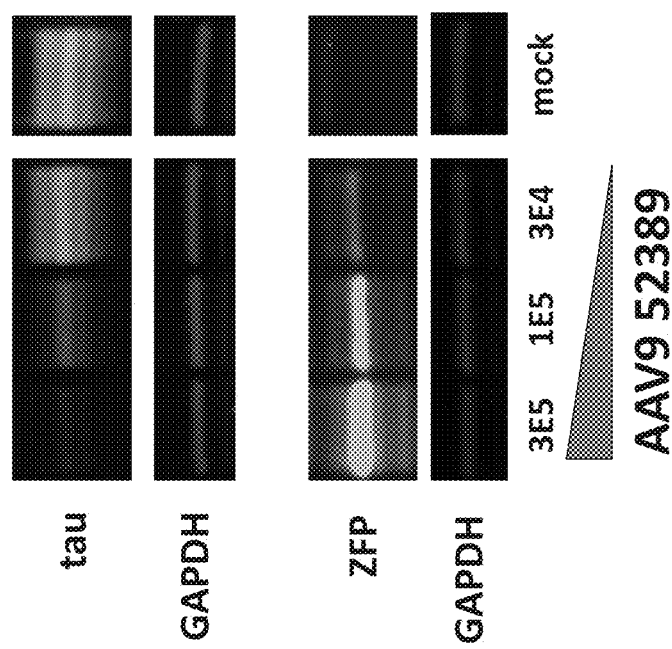

As shown in FIG. 1C, all ZFP-TF encoding AAV vectors were found to effectively repress mouse MAPT over a broad range of infected doses, with some ZFPs reducing the target by greater than 95% at multiple doses. In contrast, no MAPT repression was observed for a rAAV2/9 CMV-GFP virus tested at equivalent doses, or mock-treated neurons (see FIG. 1).

rAAV2/9 encoding CMV-52389-KRAB was used to infect mouse cortical neurons at 3E5, 1E5, and 3E4 VG/cell. After 10 days, total protein was extracted from one set of replicates; a parallel group of infections was used for total RNA extraction. Equal amounts of total cell lysate were probed by western blot for total tau protein (anti-tau-5), 52389-KRAB (anti-ZNF10), and GAPDH (anti-GAPDH) (see FIG. 2A). Quantitative fluorescence was measured using the LiCOR Odyssey system, revealing 98% tau protein reduction at the 3E5 VG/cell dose compared to mock-treated neurons (see FIG. 2). The expression of MAPT, 52389-KRAB, and two reference genes (ATP5b, EIF4a2) was monitored using real-time RT-qPCR. MAPT transcript levels were reduced by 98% at the 3E5 VG/cell group relative to mock-treated neurons (see FIG. 2).

Thus, genetic modulators (e.g., repressors) as described herein, including those that bind to the target sites as shown in Tables 1 and 2, were functional repressors when formulated as plasmids, in mRNA form, in Ad vectors and/or in AAV vectors.

Example 3: Specificity of MAPT Repression

The global specificity of the ZFP-TFs shown in Tables 1 and 2 was evaluated by microarray analysis in mouse Neuro2A cells. In brief, 300 ng of ZFP-TF encoding mRNA was transfected into 150,000 Neuro2A cells in biological quadruplicate. After 24 hours, total RNA was extracted and processed via the manufacturer's protocol (Affymetrix Genechip MTA1.0). Robust Multi-array Average (RMA) was used to normalize raw signals from each probe set. Analysis was performed using Transcriptome Analysis Console 3.0 (Affymetrix) with the "Gene Level Differential Expression Analysis" option. ZFP-transfected samples were compared to samples that had been treated with an irrelevant ZFP-TF (that does not bind to MAPT target site). Change calls are reported for transcripts (probe sets) with a >2 fold difference in mean signal relative to control, and a P-value<0.05 (one-way ANOVA analysis, unpaired T-test for each probeset).

Figure 3:
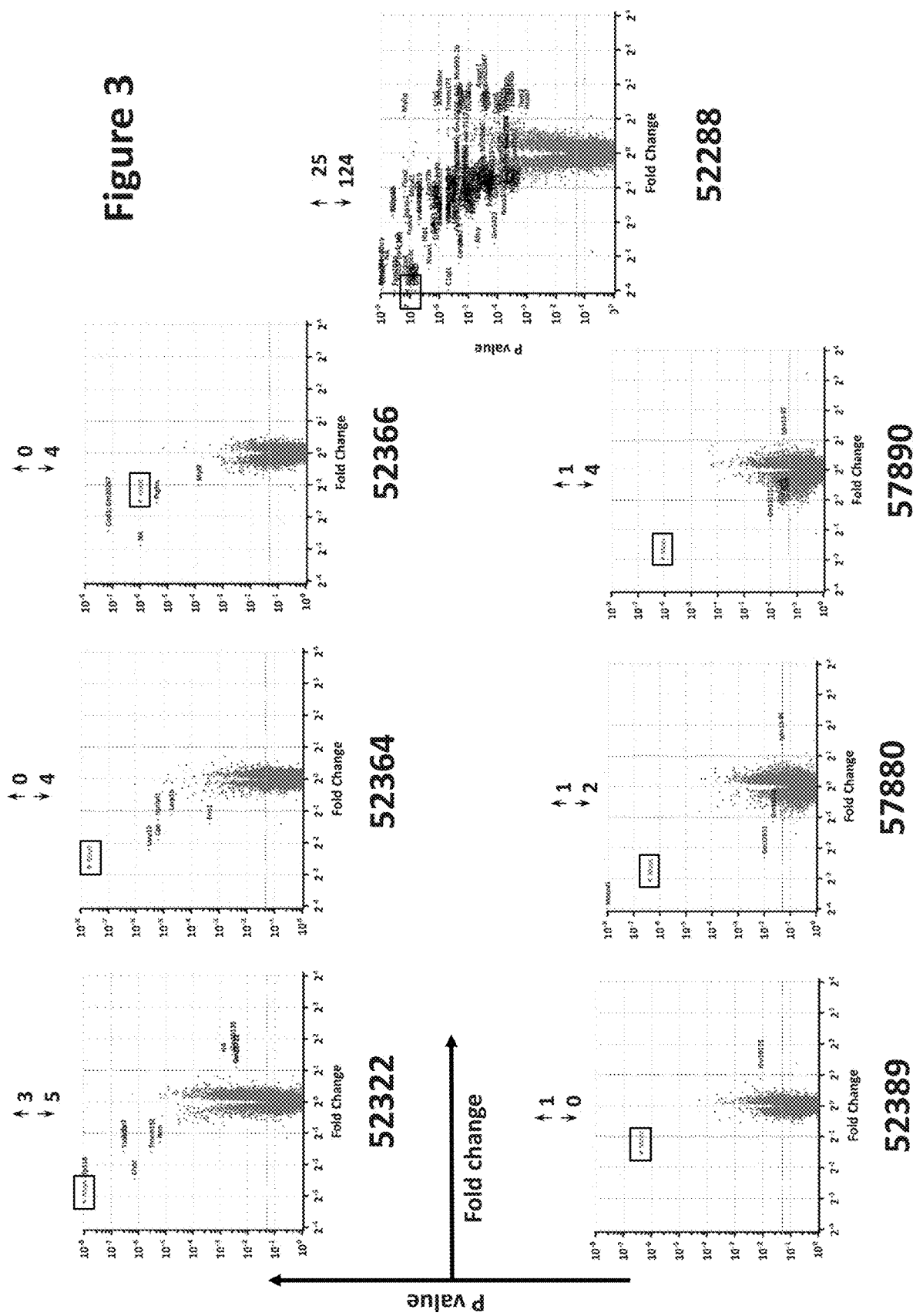
FIG. 3 shows results of microarray analysis results showing specificity of the indicated repressors (52322, 52364, 52366, 52389, 57880, 57890 or 52288) for the MAPT gene. Analysis was performed 24 hours after administration to Neuro2A cells of the repressors in mRNA form at 300 ng. Results are discussed in Example 3. The numbers above each graph represent the number of genes whose expression increased (up arrow) or decreased (repression) (down arrow).

As shown in FIG. 3, SBS #52322 repressed 5 genes in addition to MAPT, and caused an increase in 3 others. SBS #52364 and #52366 repressed 4 genes in addition to MAPT, whereas SBS #52389 caused repression of only the MAPT gene and an increase of 1 gene. SBS #57880 reduced 2 genes in addition to MAPT, and increase 1 gene. SBS #57890 reduced 4 genes in addition to MAPT, and increased 1 gene. SBS #52288 repressed 124 genes in addition to MAPT and increased expression of 25 genes.

Figure 4:
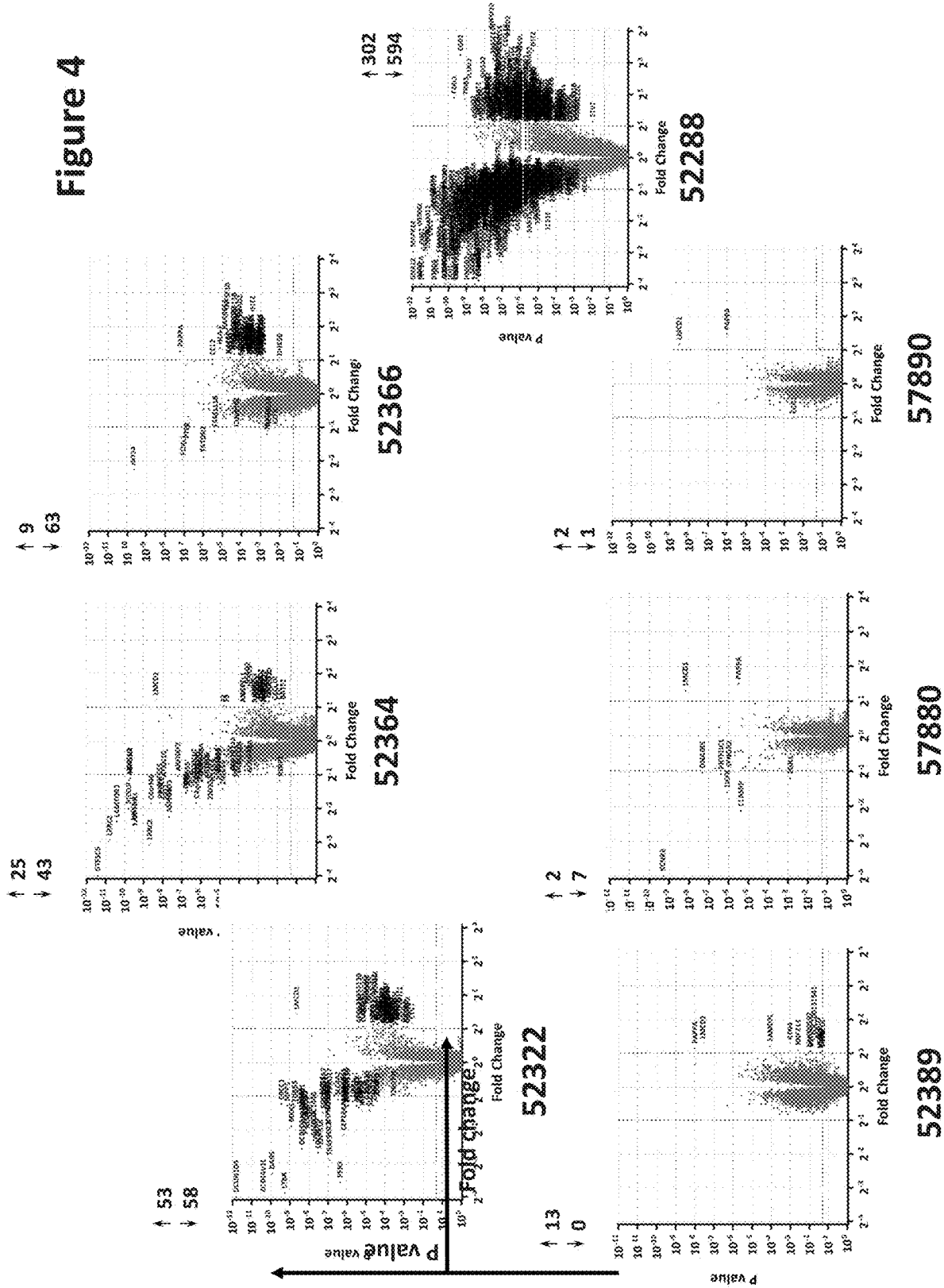
FIG. 4 shows results of microarray analysis results of the indicated repressors (52322, 52364, 52366, 52389, 57880, 57890, 52288) 24 hours after administration to primary human fibroblasts of the repressors in mRNA form at 300 ng. Results are discussed in Example 3. The numbers above each graph represent the number of genes whose expression increased (up arrow) or decreased (repression) (down arrow).

ZFP-TF specificity was also assessed in primary human fibroblasts, which are more sensitive to transfection and allow for evaluating specificity at even higher effective ZFP-TF levels. Four biological replicates of each treatment were used, consisting of 300 ng of ZFP-TF encoding mRNA transfected into 150,000 human fibroblasts. After 24 hours, total RNA was extracted and processed via the manufacturer's protocol (Affymetrix Human Primeview). Processing and analysis were as described for Neuro2A cells. Importantly, human fibroblasts do not express MAPT, therefore no change in MAPT levels was detected. Based on the fold-change criterion previously outlined, SBS #52322 repressed 58 genes and caused an increase in 53 others. SBS #52364 repressed 43 genes and increased 25 genes. SBS #52366 repressed 63 and caused an increase in 63 others. SBS #52389 did not repress any genes, and increased 13 others. SBS #57880 reduced 7 genes, and increased 2. SBS #57890 reduced 1 gene, and increased 2, while SBS #52288 repressed 594 genes while increasing the expression of 302 genes (see FIG. 4).

ZFP-TF specificity was further assessed in primary mouse cortical neurons following AAV delivery of the ZFP-TFs. Six biological replicates of each treatment were used, consisting of rAAV2/9 encoding the CMV-ZFP-TF infected at 1E5 VG/cell into 160 k primary mouse cortical neurons. After 7 days, total RNA was extracted and processed via the manufacturer's protocol (Affymetrix Genechip MTA1.0). Processing and analysis were as described for Neuro2A and fibroblasts cells.

Based on the fold-change criterion previously outlined, SBS #52322 repressed 80 genes in addition to MAPT, and caused an increase in 19 others. SBS #52364 repressed 29 genes in addition to MAPT, and increased 2 genes. SBS #52389 repressed 1 gene in addition to MAPT. SBS #57880 reduced 60 genes in addition to MAPT, and increased 3. SBS #57890 only repressed MAPT, and increased 1 gene (see FIG. 5).

Experiments were also carried out to examine the effect on specificity that modification(s) (as described herein U.S. patent application Ser. No. 15/685,580) of potential phosphate contacts from the zinc finger backbone. Two exemplary ZFP tau repressing proteins were compared (57880 and 65888) that have identical helix domains (see Table 3), but 65888 has mutations in the zinc finger backbone to remove potential phosphate contacting amino acid residues.

Figure 5B:
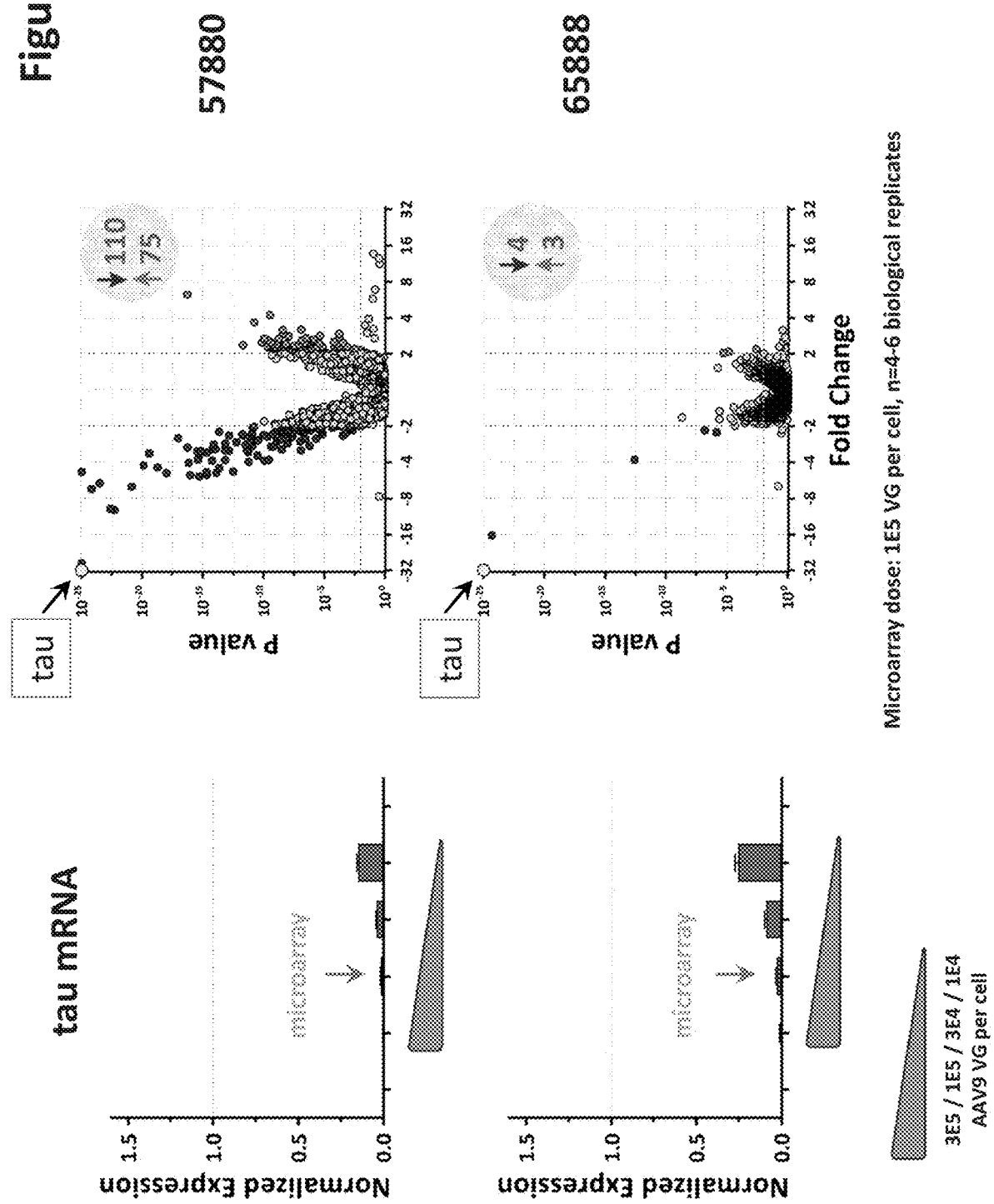

As shown in FIG. 5B, the number of genes that were either up and down regulated by 57800 (75 and 110, respectively) were markedly reduced (3 upregulated and 4 down regulated, including tau) by the 65888 protein, demonstrating increased specificity by modifications to the backbone region.

Example 4: Neuronal Promoters for CNS-Restricted ZFP-TF Expression

Three neuronal promoters were evaluated for their ability to express ZFP-TFs in primary mouse neurons: a 469 bp fragment of the human SynapsinI promoter (SYN1; Kúgler et al., (2001) *Methods Mol Med* 53:139-50), a 375 bp fragment of the alpha-calcium/calmodulin-dependent protein kinase promoter (CamKII; Dittgen et al., (2004) *Proc Natl Acad Sci USA* 101(52):18206-11),), and a 229 bp fragment of the methyl CpG-binding protein 2 promoter (MeCP2; Adachi et al., (2005) *Hum Mol Genet* 14(23):3709-22).). Each fragment was cloned in place of the CMV promoter used in Example 2, and rAAV2/9 was manufactured for each promoter construct driving 52389-KRAB linked by a 2A peptide sequence to enable co-expression of both proteins (Nagai et al., (2002) *Nat Biotechnol* 20(1):87-90 and M. D. Ryan et al., (1991) *J. Gen. Virol.* 72 p. 2727).

The purified virus was used to infect cultured primary mouse cortical neurons at 3E5, 1E5, 3E4, and 1E4 VG/cell. After 7 days, total RNA was extracted and the expression of MAPT and two reference genes (ATP5b, EIF4a2) was monitored using real-time RT-qPCR.

Figure 6B:
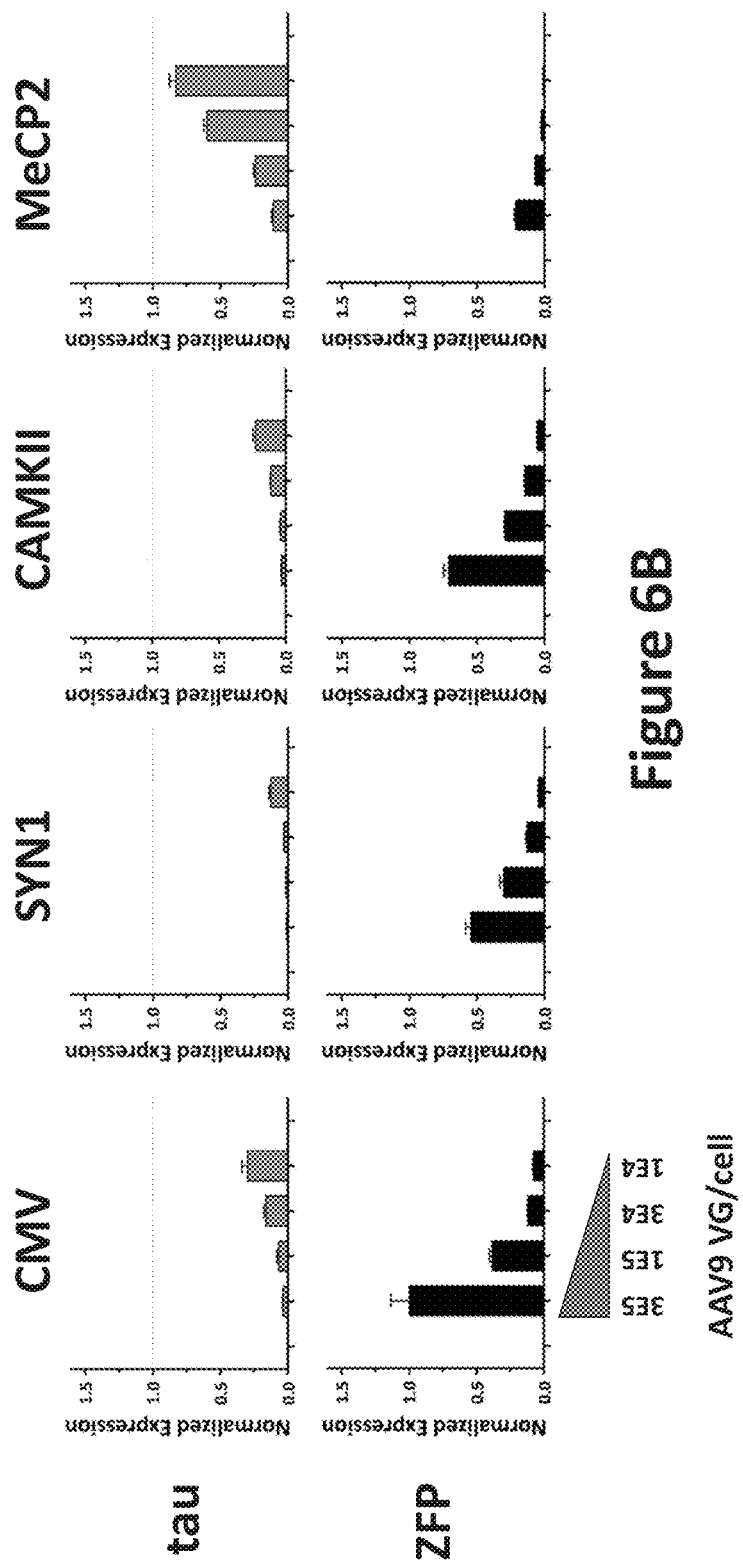

All promoters resulted in ZFP expression, with both SYN1 and CamKII achieving similar transcript levels to CMV. In contrast, MeCP2 was expressed at roughly 10-fold lower levels. MAPT was also repressed over the broad range of infected doses, with SYN1 showing the strongest response, followed by CAMKII, then CMV, and finally MeCP2 with the weakest levels of MAPT repression. At the top dose of 3E5 VG/cell, all promoters were capable of repressing MAPT by >90%, with SYN1 showing the strongest MAPT reduction of 99.4% (~175× fold lower) compared to mock-treated neurons (see FIG. 6A).

The purified virus was also used to infect cultured primary hippocampal neurons and samples were analyzed and processed as described for cortical neurons. All neuronal promoters resulted in ZFP expression and MAPT repression with the same rank order of activity, similar degree of repression, and dose-response profiles observed in primary cortical neurons (see FIG. 6B).

Collectively, these results suggest that any of the neuronal promoters would be sufficient to achieve ZFP expression and MAPT repression in the primary regions of interest for MAPT-related indication, namely the hippocampus and cortex.

Further, the use of a strong neuronal promoter (such as SYN1 or CAMKII) can be employed to reduce the level of a highly expressed transcript target, when adequate delivery of the ZFP-TF is a limiting (for example via intravenous or intrathecal delivery), and/or in a case where a low-affinity ZFP-TF might be selected to minimize off-target gene regulation. Conversely, a weaker neuronal promoter (such as MeCP2) can be selected when the target gene of interest is expressed at moderate to low levels, when sufficient delivery to the target regions is non-limiting (for example direct intracranial delivery), and/or to minimize off-target activity of a high-affinity ZFP-TF.

Example 5: Repression of Human MAPT in iPS-Derived Neurons

Figure 7C:
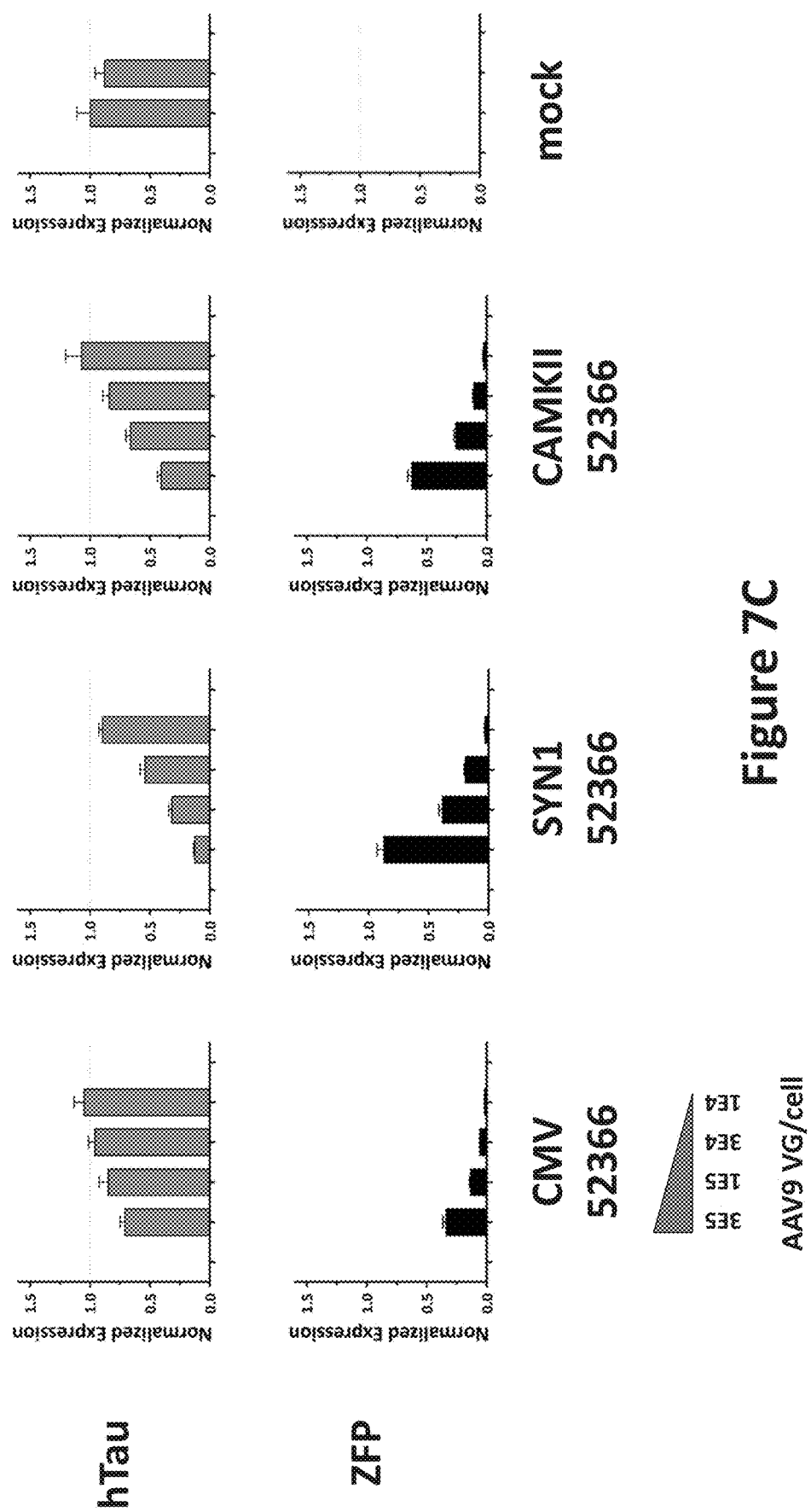

Based on a standard SELEX specificity analysis of all ZFPs described herein, the ZFPs listed in Tables 2 and 3 were predicted to tolerate mismatches at the one (in the case of SBS #57890 and SBS #52366) or two (in the case of SBS #57880) non-conserved positions in the human MAPT sequence (see FIG. 7A).

Exemplary ZFP-TFs in Tables 2 and 3 were cloned into an AAV vector (AAV6, AAV9 AAV2/9, or variants thereof) with the 469 bp SYN1 promoter fragment described in Example 4. rAAV virus was produced in HEK293T cells, purified using a CsCl density-gradient, and titered by qPCR. The purified virus was used to infect human iPS-derived neurons at 3E5, 1E5, 3E4, and 1E4 VG/cell (iCell Neurons, Cellular Dynamics International Inc). After 18 or 19 days, total RNA was extracted and expression of human MAPT, ZFP-KRAB, and three reference genes (ATP5b, EIF4a2, GAPDH) was assessed using real-time RT-qPCR. Similar levels of ZFPs were expressed for each virus across the range of doses tested.

Figure 7D:
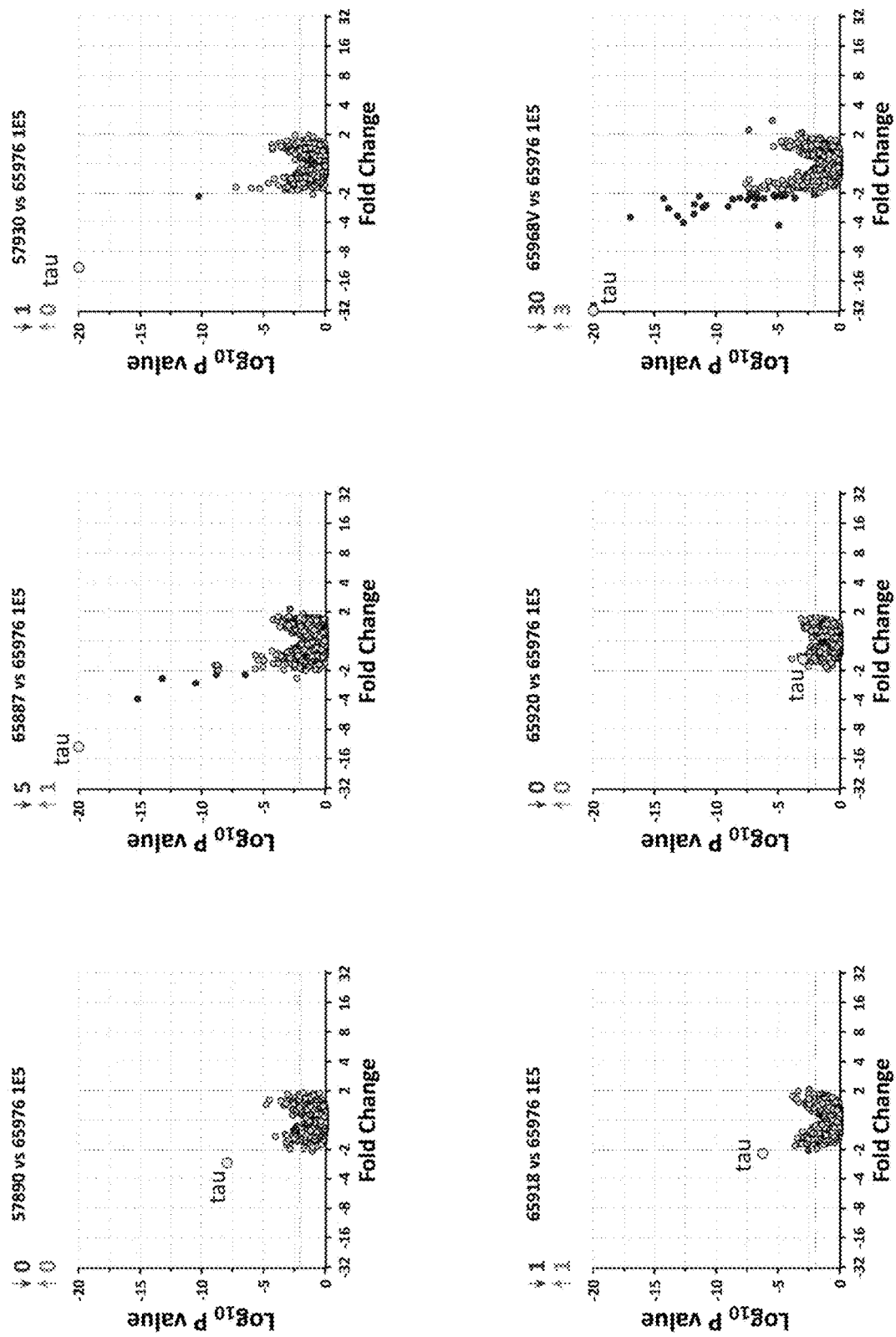

Exemplary results are shown in FIG. 7. At the top dose of 3E5 VG/cell, 57880-KRAB repressed human MAPT by 95%, 52366-KRAB resulted in 87% MAPT reduction, and 57890-KRAB lowered MAPT by 45% compared to mock-infected cells (see FIG. 7B). Similar results were obtained for the other transcription factors described herein (e.g., ZFP-TFs as shown in Tables 1 through 3). One explanation for the reduced human MAPT repression activity of SBS #57890—compared to the behavior observed for mouse MAPT—is its exceptional degree of genome-wide specificity, consistent with a poor tolerance for mismatches in its target site (see Example 3).

The CMV, SYN1, and CAMKII promoters were evaluated for ZFP-TF expression and MAPT repression of human MAPT using the ZFP-TF 52366. rAAV2/9 was manufactured for each promoter construct driving 52366-KRAB and used to infect human iPS-derived neurons as described. The SYN1 promoter resulted in the highest levels of ZFP expression and MAPT reduction (5% of mock-treated neurons) compared to CAMKII (40% of mock) and CMV (71% of mock) (see FIG. 7C).

The human iPS derived neurons were also subject to microarray analysis as described above to analyze the amount of off target repression in a population of 19,959 coding transcripts. In each case, the ZFP-TFs were compared to the 65976 protein based on the fold-change criterion previously outlined, and the plots indicate the change in profile for the test ZFP-TF (see FIG. 7D). The results indicate that several of the human tau ZFP-TFs are highly specific in human neurons.

Example 6: In Vivo MAPT Repression Driven by AAV-Delivered ZFP TFs

Various ZFP-TFs as described herein were delivered using various different AAV vectors to the mouse hippocampus to evaluate repression of MAPT in vivo. AAVs encoding Tau repressors were administered either intravenously (IV) or intracerebroventricularly (ICV) with 57890.T2A. Venus or intracranially (IC) by stereotactic injection.

In brief, for AAV 2/9, a total dose of 8E9 VGs of rAAV2/9-CMV-ZFP-TF per hemisphere was administered by stereotactic injection via dual, bilateral 2 injections. For AAV vectors described in U.S. Pat. No. 9,585,971, AAV vectors were administered intracerebroventricularly (ICV) or intravenously (IV) at total doses of 1E12. AAV vectors as described in U.S. Provisional Patent Application No. 62/503,121 were administered ICV at 1E12 vg or 2E12 vg/animal for IV.

The animals were sacrificed four (IV and ICV) or five weeks (IC) post-injection. For the IV and ICV treated animals, the right hemisphere was dissected into the various brain regions for RT-qPCR analysis, and the left hemisphere was used for histology. For the IC treated animals, each hippocampus was sectioned into three pieces for RT-qPCR analysis (A, Anterior; B, middle; C, posterior hippocampus). MAPT and ZFP-TF expression was also analyzed by real time RT-qPCR and normalized to the geometric mean of three housekeeping genes (ATP5b, EIF4a2 and GAPDH).

The data showed that the AAV vectors efficiently transduced neuronal targets when administered intracerebroventricularly or intravenously and that the ZFP-TFs resulted in potent and sustained tau reduction throughout the CNS (brain and spinal cord, including in frontal cortex, anterior cortex, posterior cortex, hippocampus, brain stem, striatum, thalamus, midbrain, cerebellum, lumbar spinal cord, thoracic spinal cord and cervical spinal cord). FIGS. 8A to 8C show exemplary results using ZFP-TFs SBS #52322, SBS #52389 and SBS #57890 following administration of AAV vectors described in 62/503,121 ("SGMO" in FIG. 8B) as compared to AAV9 ("9" in FIG. 8B). The micrograph depicted in FIG. 8A was taken 4 weeks after delivery of the SGMO vector, with doses of 1e11 vg/mouse for ICV delivery and 2e12 vg/mouse for IV delivery. FIG. 8C depicts the changes in tau mRNA levels following a single administration via ICV or IV dosing from the same experiment. The same results were found for all additional ZFP-TFs tested.

FIGS. 8D and 8E show exemplary results using AAV2/9 vector and demonstrated that for intracranial delivery to the hippocampus, both 52389-KRAB and 52322-KRAB were able to repress MAPT efficiently (see FIG. 8D). Coverage was assessed by the relative ZFP expression levels across the three slices for each hemisphere. This analysis revealed that, while many slices had excellent coverage, several had little or no ZFP-TF expression, suggesting non-uniform coverage throughout the hippocampus for several animals following intracranial stereotaxic delivery (see FIG. 8E). Similar results were obtained with other ZFP-TFs as described herein.

Figure 8G:
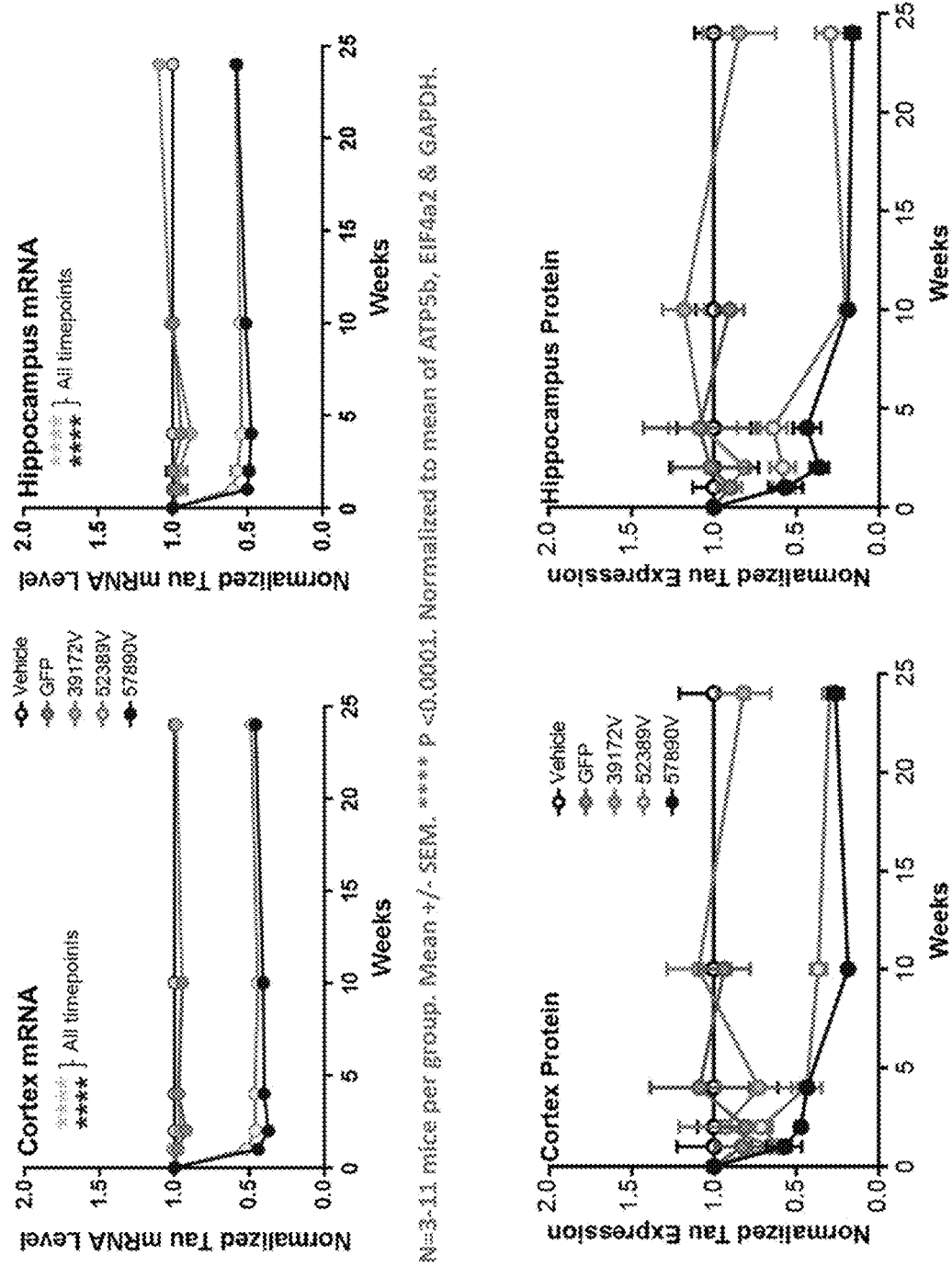
FIG. 8G are graphs depicting tau repression is rapid and sustained over months in cortex (left panels) and hippocampus (right panels) of animals administered the indicated compositions ("GFP" refers to the GFP control; "172" refers to the irrelevant control ZFP-TF that does not bind to MAPT; "52389" refers to the 52389 repressor carried on an AAV construct; "57890" refers to the 57890 repressor described herein carried on an AAV construct; and "PBS" refers to the control of animals receiving only PBS). The top row in FIG. 8G depicts Tau mRNA expression and the bottom row depicts normalized Tau protein levels.
Figure 10A:
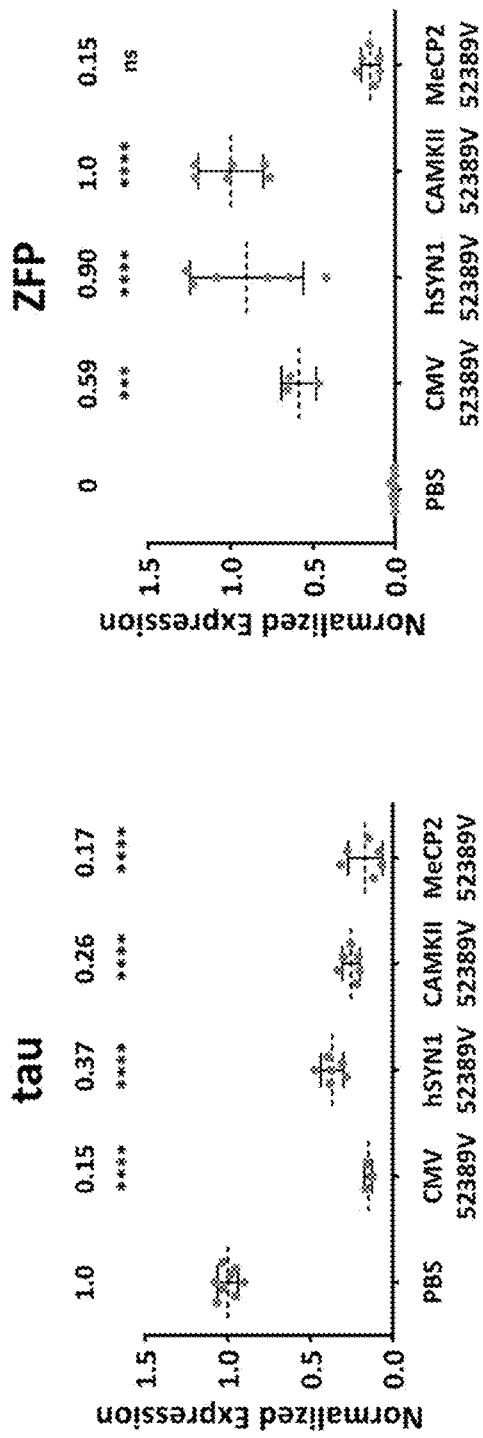
FIGS. 10A through 10D are graphs depicting MAPT (tau) mRNA repression following treatment with the tau-specific ZFP-TF in vivo following injection into the hippocampus. In this experiment, four different promoters (CMV, SNY1, CAMKII or MeCP2) were used to drive the expression of the ZFP-TF-venus construct.
Figure 10B:
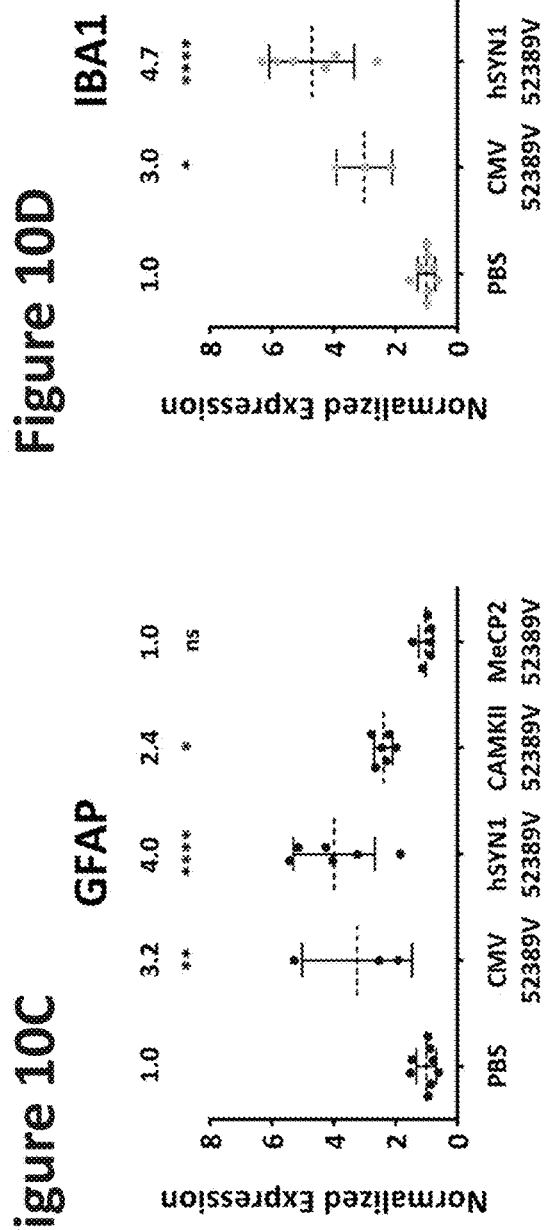
Figure 10C:
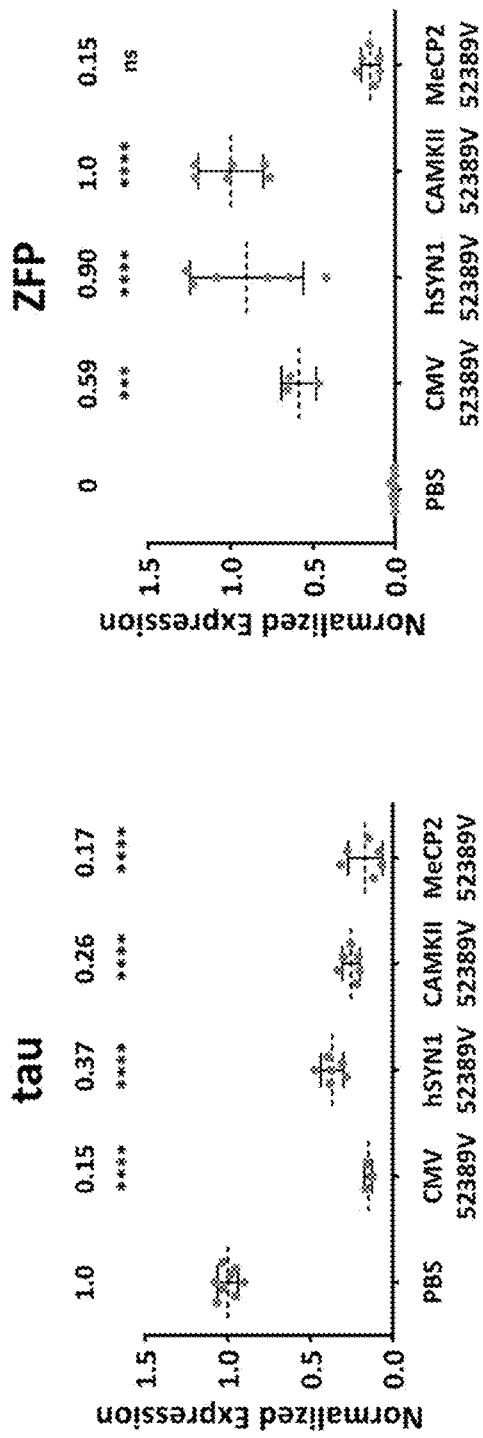
Figure 10D:
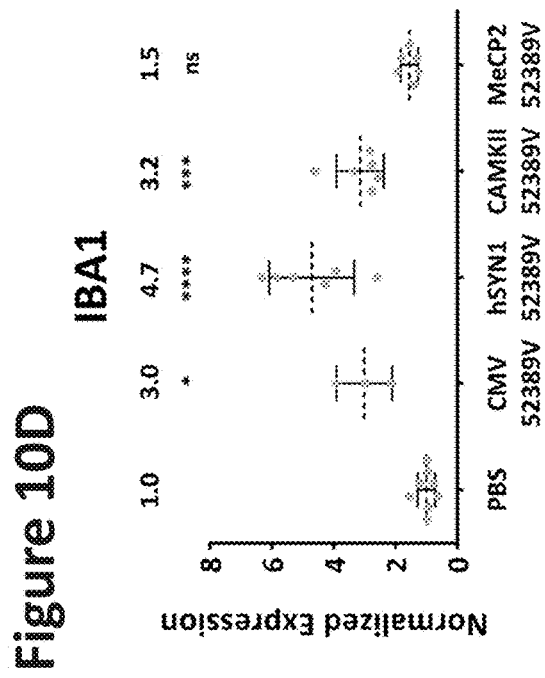

In addition, tau repressors as described herein delivered using the AAV vector described in U.S. Pat. No. 9,585,971 also significantly repressed tau in the CNS (including spinal cord). Exemplary results are shown in FIGS. 8F-8H. For all ZFP-TFs described herein, repression in the CNS was rapid and sustained over time, both at the mRNA protein levels. Furthermore, CSF levels of tau correlate with brain levels and thus can be used as an indicator of tau repressor function (see, exemplary FIG. 8H).

In sum, any tau repressor as described herein, delivered by any AAV vector by any route effectively modulates (represses) tau for sustained periods.

To further understand the degree of ZFP-TF induced MAPT repression in the hippocampus, three analysis methods were used. First, ZFP-TF and MAPT expression values from all six slices from each animal in a treatment group were averaged and compared to the PBS group by ANOVA followed by Sidak's post-test. Highly significant ($P<0.0001$) MAPT repression was observed for both 52322 (mean MAPT reduction 66%) and 52389 (mean MAPT reduction 55%) (see FIG. 9A).

Second, the section from each animal with the highest level of ZFP-TF expression was identified and used to calculate the average maximal tau reduction under an ideal coverage scenario. Again, highly significant ($P<0.0001$) MAPT repression was observed for all ZFP-TFs tested. Exemplary results, shown in FIG. 9B, show reduction by over 70% using 52322 (mean MAPT reduction 73%) and 52389 (mean MAPT reduction 89%).

Third, the correlation between MAPT and ZFP-TF levels (expressed here as the absolute value of ZFP copies/ng of RNA input in the RT-qPCR reaction) was assessed. A highly significant relationship was observed for both 52322 ($P<0.0001$, $R^2=0.53$) and 52389 ($P<0.0001$, $R^2=0.82$) (see FIGS. 9C and 9D).

Tau reduction in the P301L mutant human tau (P301L) transgenic mouse model of tauopathy (rTg4510, Jackson Labs) is also assessed following administration of genetic repressors as described herein. In addition, the clinical and therapeutic effectiveness of the repressors is evaluated in this and other mouse models of AD (e.g., APPswe/PS1d9, Jackson Labs) to determine whether there is a reduction in biomarkers and symptoms of tauopathies, including one or more the following: neurotoxicity, gliosis, dystrophic neurites, spine loss, excitotoxicity, cortical and hippocampal shrinkage, dendritic tau accumulation, cognitive (e.g., the radial arm maze and the Morris water maze, fear conditioning, etc.), and motor deficits. See, e.g., Bryan et al., (2009) Chapter 1: Transgenic Mouse Models of Alzheimer's Disease: Behavioral Testing and Considerations in *Methods of Behavior Analysis in Neuroscience*. 2nd edition, ed. Buccafusco, Boca Raton (Fla.): CRC Press/Taylor & Francis. Additionally, chemically induced seizure models, for example, wild-type mice treated with excitotoxic compounds such as pentylenetetrazole (PTZ, see e.g. Meyers et al., (1975) Epilepsia 16(2):257-67) or kainate (Ferraro et al., (1997) *Mamm Genome* 8:200-208, are also assessed at 4-8 weeks following administration of genetic repressors as described herein, to determine whether tau reduction confers a protective effect against seizure, including, fatality related to seizure, prolonged latency to seizure, and/or reduction in seizure severity.

Tau modulators (e.g., repressors) as described herein were delivered using non-viral or viral (e.g., AAV) vectors as described herein directly into the brain, for example by intracranial injection into the hippocampus or cortex, intracerebroventricular or intravenous delivery. After a period of time post-administration of the repressors (1-11 months post-repressor administration), brains were harvested, sectioned and subjected to immunohistochemistry analysis and/or imaging analysis (e.g., 2-photon imaging) to assess neuronal viability, gliosis, dystrophic neurites, spine density, cortical and hippocampal thickness, tau mRNA expression and tau protein levels.

Mice receiving the repressors showed an 80-90% or more repression of tau (mRNA and protein) in ZFP expressing neurons 8 weeks after administration of the ZFP repressors. No significant neuronal loss or elevated gliosis was seen after long-term (6 months) tau knock-down. Mouse tau repression also protective against neuritic dystrophies. Thus, the tau modulators (e.g., repressors) as described herein provide in vivo clinical and therapeutic benefits to subjects with tauopathies.

Example 7: In Vivo MAPT Repression and Protein Knockdown Driven by AAV-Delivered ZFP TFs Expressed from Neuronal Promoters Recombinant AAV vectors encoding ZFP-TFs 2A-Venus constructs as described herein driven by the CMV, SYN1, CAMKII, or MeCP2 promoters described in Example 5 were delivered to the mouse hippocampus to evaluate MAPT mRNA and protein reduction in vivo. In brief, a total dose of 2.4E10 VGs per hemisphere was administered by stereotactic injection to adult wild-type mice via dual, bilateral 1.5 µL injections. The animals were sacrificed six weeks post-injection and each hippocampus was finely homogenized with a razor blade, and the resulting tissue was distributed into two equal amounts. One half was taken for mRNA analysis, wherein MAPT, ZFP-TF, GFAP, and IBA1 expression was analyzed by real time RT-qPCR and normalized to the geometric mean of three housekeeping genes (ATP5b, EIF4a2 and GAPDH). The other half was taken for quantitative tau protein analysis by ELISA, and exemplary results are presented in FIG. 10. Relative to control-treated animals, tau mRNA was reduced by at least 85% following administration of the AAV ZFP-TF. Exemplary results following administration of rAAV9-CMV-52389V were as follows: 63% reduction in tau expression by the rAAV9-SYN1-52389V; 74% reduction in tau expression by the rAAV9-CAMKII-52389V; and 83% reduction by the rAAV9-MeCP2-52389V construct (P<0.0001 for all promoters). Mean ZFP expression was found to be highest for the vector encoding the CAMKII promoter (set to a value of 1), lowest for the MeCP2 promoter (15% of the CAMKII levels), and intermediate for the CMV (59% of CAMKII levels) and SYN1 (90% of CAMKII levels) promoters.

The presence of microglia and activated astrocytes was also assessed using RT-qPCR reagents for IBA1 and GFAP, respectively. The MeCP2 promoter resulted in no significant changes in IBA1 levels compared to PBS-injected animals, SYN1 resulted in 4.7-fold higher IBA1 levels (P<0.0001), CMV resulting in 3.0-fold higher levels (P<0.05), and CAMKII resulted in levels 3.2-fold higher (P<0.001). Similarly, the MeCP2 promoter resulted in no GFAP elevation compared to PBS-injected animals, SYN1 resulted in 4.0-fold higher GFAP levels (P<0.0001), CMV resulting in 3.2-fold higher levels (P<0.01), and CAMKII resulted in levels 2.4-fold higher (P<0.05).

Figure 11:
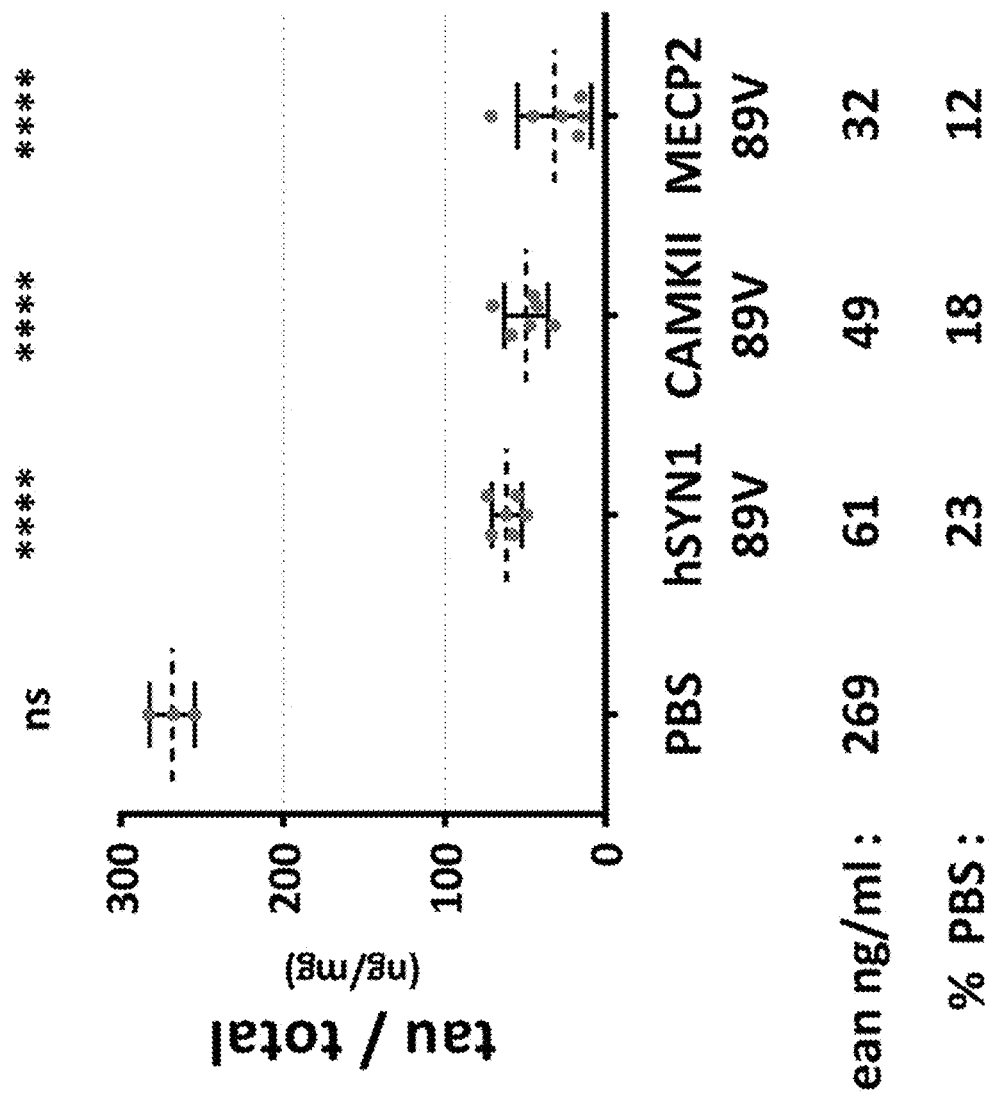
FIG. 11 is a graph showing the reduction in tau protein expression in the groups described in FIG. 10. Compared to PBS-injected control levels (269 ng/ml), the rAAV9-SYN1-52389V construct resulted in 23% of control levels (61 ng/ml, P<0.0001), the rAAV9-CAMKII-52389V construct yielded 18% of control levels (49 ng/ml, P<0.0001), the rAAV9-SYN1-52389V construct had 12% of control levels (32 ng/ml, P<0.0001). Thus, neuronal promoters are capable of driving >80% tau mRNA and protein reduction throughout the mouse hippocampus.

Robust reduction in total tau protein was also observed for all three neuronal promoter constructs (exemplary results using SBS 52389 shown in FIG. 11). Compared to PBS-injected control levels (269 ng/ml), the rAAV9-SYN1-52389V construct resulted in 23% of control levels (61 ng/ml, P<0.0001), the rAAV9-CAMKII-52389V construct yielded 18% of control levels (49 ng/ml, P<0.0001), the rAAV9-SYN1-52389V construct had 12% of control levels (32 ng/ml, P<0.0001). Similar or high levels of reduction are obtained with other ZFP-TFs as described herein (e.g., 57890, 65894, 57930, 65918, 65920, 57880, 65887, 65888, 57947, 65968, 52322, 52364, 52366, 52288, 52389 and/or 65860).

Thus, neuronal promoters are capable of driving >80% tau mRNA and protein reduction throughout the mouse hippocampus.

Example 8: Histological Evidence of Tau Reduction Throughout the Hippocampus and Connected Brain Regions Artificial transcription factors as described herein were delivered to the mouse hippocampus to evaluate repression of tau in vivo by immunofluorescence staining. A total dose of 2.4E10 VGs of rAAV-CMV-ZFP-TF (rAAV2/9, rAAV6, etc.) was administered by stereotactic injection via dual, unilateral 1.5 µL injections to adult wild-type mice. The ZFP-TFs were linked to a fluorescent Venus protein to localize TF expression. The animals were sacrificed six weeks post-injection and the entire brain was collected and sectioned for histological staining for nuclei (DAPI), tau and GFP using standard methods. Fluorescent activated cell sorting (FACS) analysis was also performed. In brief, to evaluate the tau knock-down efficiency in AAV ZFP-dVenus transduced cells, we dissociated hippocampi injected with AAV CMV ZFP-dVenus using a papain dissociation kit (Worthington Biochem. Corp.) according to the manufacturer manual and then analyzed the cell suspension using flow cytometry (Miltenyi MACSQuant VYB Flow Cytometer). dVenus or GFP expressing cells in the same samples were then separated by FACS using the green 488 nm laser (BioRadS3 Cell Sorter; 30 k-50 k GFP positive cells per sample). After sorting, cells were spun down by centrifugation for 10 min at 1,000×g and resuspended in 100 µl RNA (ThermoFisher) for RNA analysis.

Exemplary results are shown in FIG. 12 (animal injected with rAAV2/9-CMV-ZFP-TF SBS #52389). FIG. 12A shows a cross section of the mouse brain through the anterior hippocampus and identifies four regions boxed and numbered 1-4. Injection was into the left hemisphere (the ipsilateral side) which results in higher fluorescence in the left side of the cross section. The subsequent panels are close up images of each of these boxes. The boxes are described below:

Box 1 (FIG. 12B) shows quantitation of fluorescence intensity across the retrosplenial cortex where ZFP-TF expression is clearly demarcated between the ipsilateral and contralateral hemispheres. In the left panel of FIG. 12B, the fluorescent signal was higher on the ipsilateral side of the midline ("ipsi") than on the contralateral side ("contra"). ZFP expression here likely arises from hippocampal axonal projections. The majority of the signal on the right side of the panel was due to the DAPI staining of the nuclei. The middle image shows overall fluorescence with anti-Tau tagged antibodies where the signal in the ipsilateral (left) side of the panel was nearly all due to GFP signal while the signal on the contralateral (right) side of the panel was mostly due to the presence of Tau and to underlying DAPI staining. The right panel of 12B shows a cross sectional box that was analyzed for quantification of the tau signal (depicted in FIG. 12C). The figure shows reduced tau-specific fluorescence from the injected (treated) side ("ipsi" versus "contra").

Box 2, FIG. 12D (ipsilateral) and Box 3, FIG. 12E (contralateral) are images from the hippocampus showing tau reduction in the ipsilateral (treated) side versus the contralateral side, tau knockdown was particularly clear in the dentate gyrus on the contralateral side versus ipsilateral (indicated by the arrow).

Box 4 is region of the hypothalamus where there was focal ZFP expression in the ipsilateral side (top panel shows GFP fluorescence, left oval) and bulk tau fluorescence (bottom panel) shows ~50% reduction in total tau signal (see graph between the ipsilateral side and the contralateral side). Similar results are obtained using AAV constructs comprising ZFP-TFs as described in Tables 1, 2 and 3.

Thus, the ZFP-TFs as described herein repress tau expression in vivo.

Figure 13G:
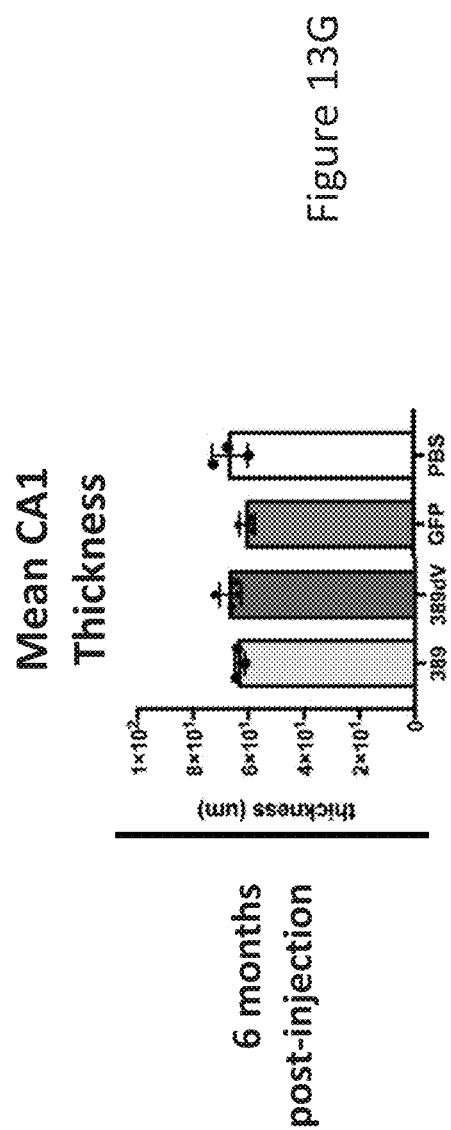
Figure 13H:
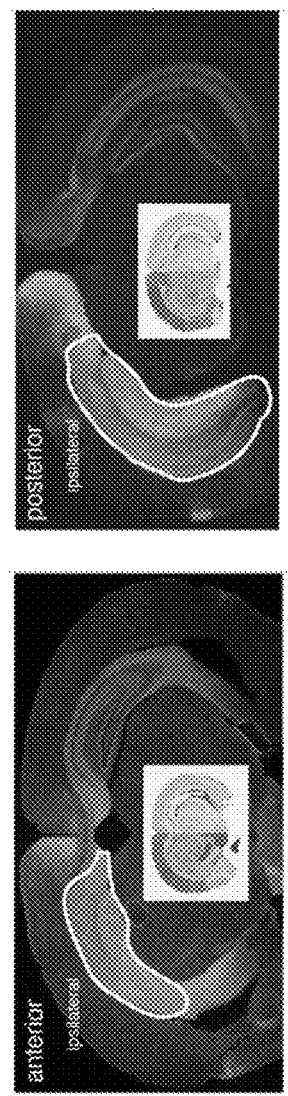
Figure 13I:
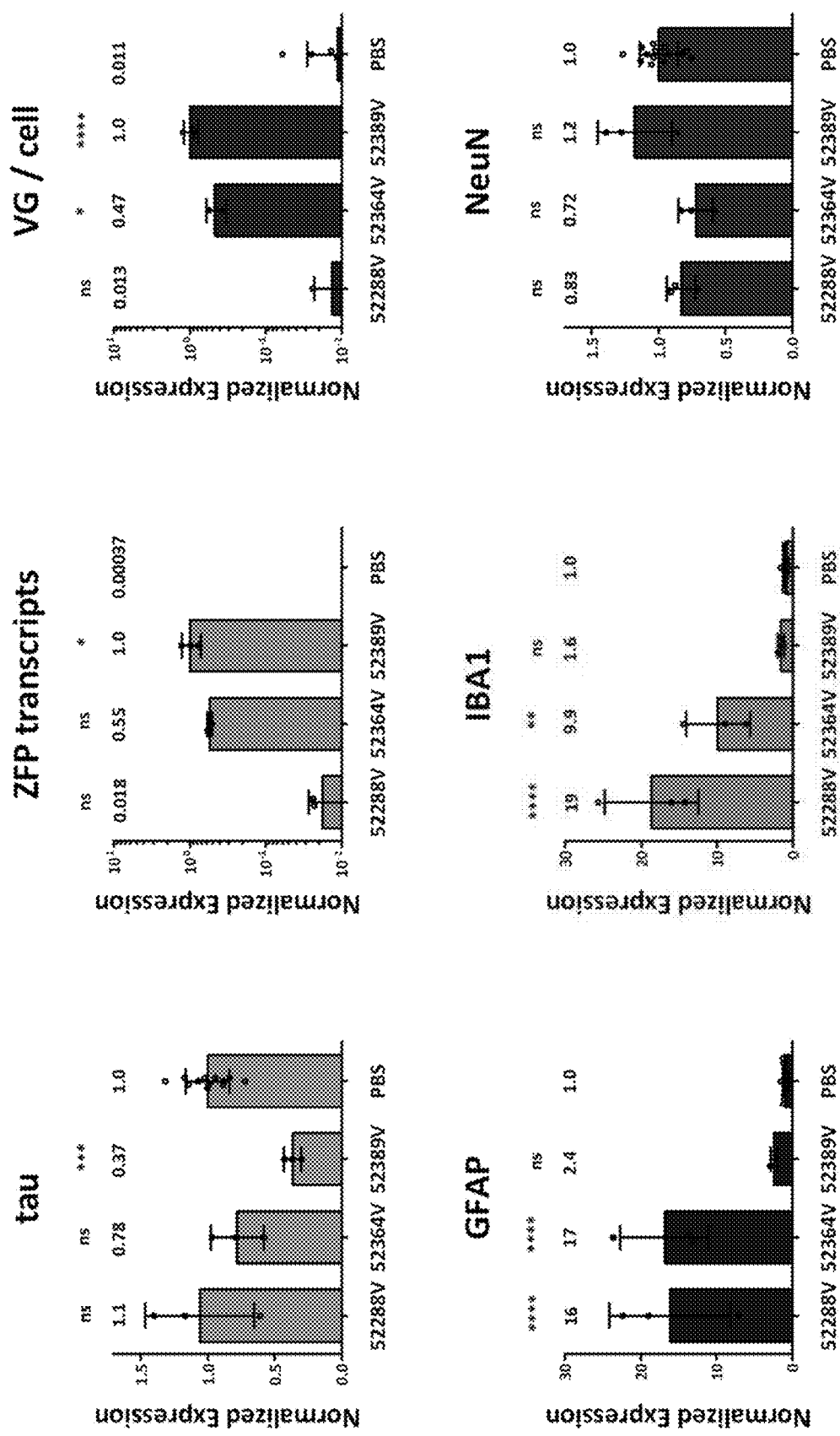
Figure 13J:
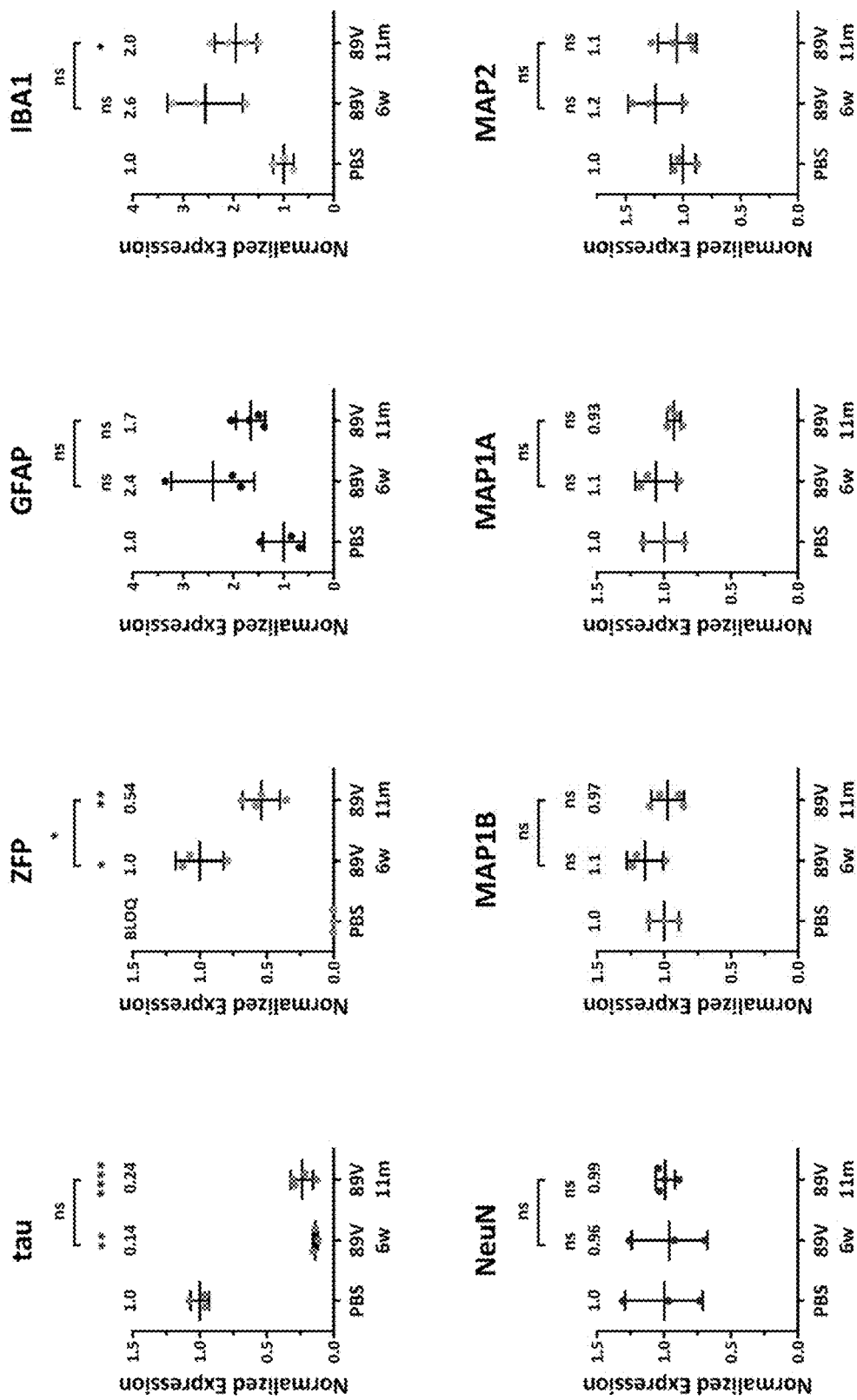
Figure 13J:
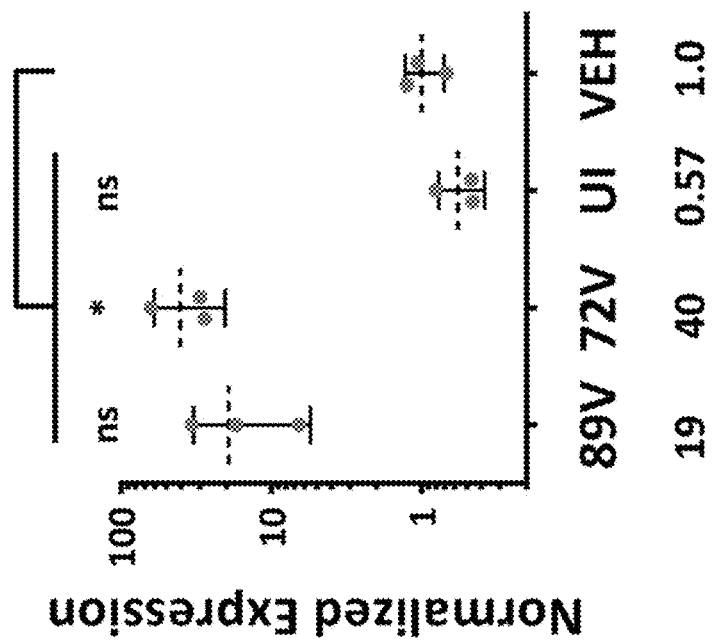
Figure 14E:
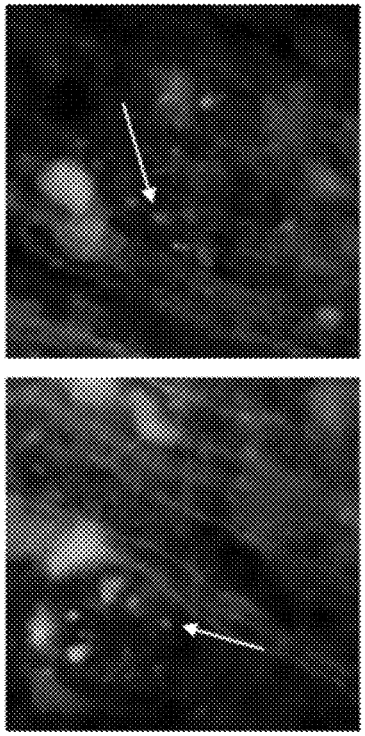
Figure 14F:
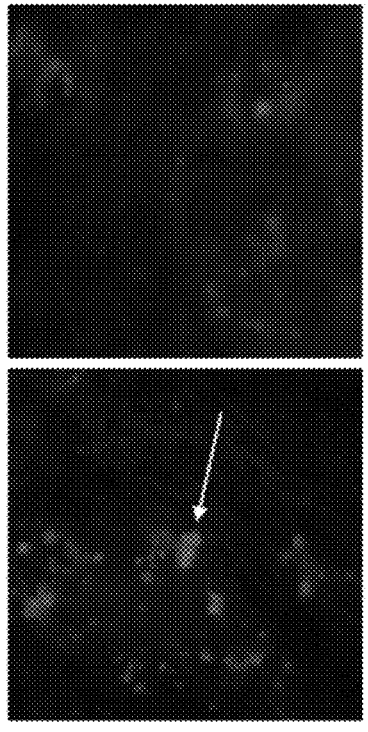

Example 9: In Vivo Safety, Tau Reduction, and Sustained Expression of a ZFP-TF in the Mouse Hippocampus To assess the safety of both short- and long-term hippocampal expression of a tau targeted artificial transcription factors described herein, ZFP-TFs as described herein were delivered in vivo to the mouse hippocampus to monitor ZFP expression as well as astrocytes and microglia responses, and gross hippocampal anatomy. In one experiment, a total dose of 2.4E10 VGs of rAAV2/9-CMV-52389-2A-Venus ("389dV"), rAAV2/9-CMV-ZFP-TF ("389"), rAAV2/9-CMV GFP ("GFP"), or PBS ("PBS") was administered by stereotactic injection via dual, unilateral 1.5 µL injections to adult wild-type mice. Two cohorts were sacrificed either at six weeks or at six months post-injection and the entire brain was collected and sectioned for histological staining for nuclei (DAPI), GFP, GFAP (to detect activated astrocytes), and IBA1 (to detect microglia) using standard methods and the results are shown in FIG. 13. FIG. 13H comprises images depicting the fluorescence of two regions of the hippocampus demonstrating that following the injections tau was repressed in both the anterior and posterior areas of the hippocampus.

For the 6-week time point (FIG. 13A), depicting signal for the transduced cells in the hippocampus, the signal for the ZFP-TF is nearly the same as for the GFP vector. FIG. 13B shows the results for the astrocytes and also shows nearly the same results across the three treatments, as also seen in the hippocampal microglia (FIG. 13C).

For the 6-month time point, the data in FIG. 13D demonstrates very similar levels of fluorescence for the GFP and ZFP TF vectors as seen in the 6-week time point, suggesting that there was not a large change in the amount of transduced cells in the hippocampus over time. FIG. 13E also shows that the signal between the different treatments was very similar and did not change significantly between the 6-week time point and the 6-month time point (FIG. 13B versus 13E—note the difference in the y axis between the two figures). The microglia at the 6-month time point after treatment with the AAV vectors are nearly the same, with a slight decrease in the PBS treated samples.

A measurement of the mean CA1 (one of the hippocampal regions) thickness shows no significant change after 6 months of ZFP expression (FIG. 13G), demonstrating no overt neuronal toxicity from long-term expression of the ZFP.

An additional analysis was performed where the ZFP-TFs were administered as above except that only PBS and the 52288, 52364 and 52389 constructs, linked to 2a-Venus were compared. Dosing was as described in Example 6. After dosing, animals were sacrificed at 4 weeks, and the data is presented in FIG. 13I. The data presented shows that treatment with the 52288 construct resulted in substantially attenuated vector genomes and ZFP expression compared to the other constructs, and did not repress tau expression in any significant way. It did however result in elevated levels of GFAP and IBA1. The ZFP 52364 had higher vector genome levels and ZFP expression than the 52288 construct, but led to similarly high levels of GFAP and IBA1, and did not significantly repress tau expression. In contrast, the 52389 construct was able to cause a significant drop in tau expression without impacting GFAP or IBA1 expression.

The lack of tau reduction in vivo and elevated neuroinflammatory biomarkers for ZFPs 52288 and 52364 correlate with the ZFP specificity profiles assessed in Neuro2A cells, human fibroblasts, and primary neurons (FIGS. 3, 4, 5), showing that highly specific ZFPs significantly reduced tau expression and were tolerable in vivo.

Part of the dosing groups receiving PBS or the 52389-2a-Venus were extended for 11 months. In addition to analyzing the amount of tau repression, samples were also analyzed for mRNA expression levels of the amount of ZFP expressed, and any change in the amount of transcripts encoding GFAP, IBA1, NeuN, MAP1A, MAP1B, and MAP2. In brief, each hippocampus was finely homogenized with a razor blade, and the resulting tissue was distributed into two equal amounts. One half was taken for mRNA analysis, wherein MAPT, ZFP, GFAP, IBA1, NeuN, MAP1A, MAP1B, and MAP2 expression was analyzed by real time RT-qPCR and normalized to the geometric mean of three housekeeping genes (ATP5b, EIF4a2 and GAPDH). Exemplary results are presented in FIG. 13J which also includes the 6-week data for comparison. The data demonstrates that in general there was not a large change in most data sets analyzed between the 6-week and 11-month time frames. There was a decrease detected however in the amount of ZFP expression detected. No significant compensatory changes were observed for three other Microtubule Associated Proteins (MAP1A, MAP1B, and MAP2), nor was there any reduction in NeuN levels, consistent with the preservation of hippocampal volume in ZFP-treated hemispheres assessed six months after ZFP delivery. Additional experiments were performed using ZFP-TFs as described herein and produced similar results.

Thus, the results demonstrate that, following a single administration, ZFP expression persists over time in vivo and does not result in toxicity to the CNS of the subject, and that ZFP-mediated tau reduction in the adult hippocampus is sustained and well-tolerated for at least 11 months.

Figure 17:
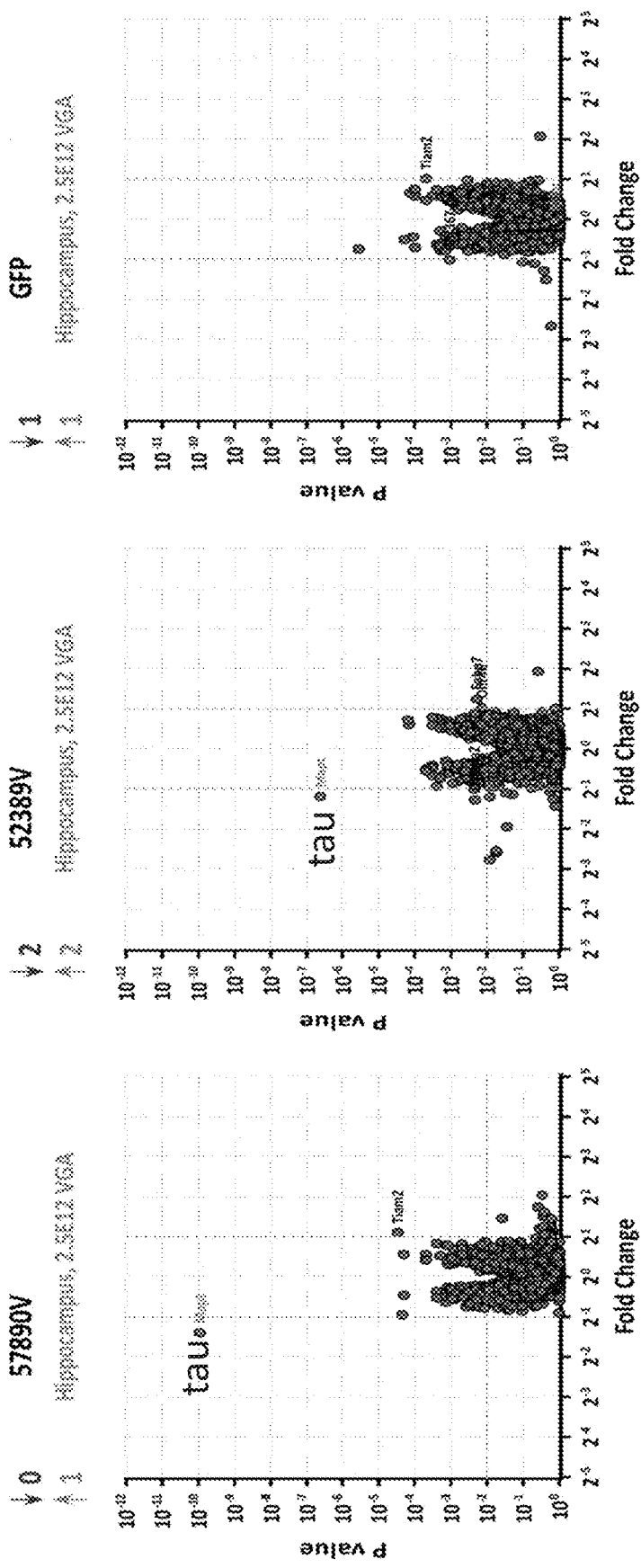
FIG. 17 depicts exemplary results of a microarray analysis on hippocampal tissue derived from mice treated with ZFP-TFs. The ZFP-TFs were delivered to the animals using AAVs described herein (2.5 e12 vg/animal) via retro-orbital delivery. The mice were treated and sacrificed at ten weeks, and the results depicted are data compared to an irrelevant ZFP-TF control.

Another study was performed using C57BL/6 wild type mice (8 week old females) where the ZFP-TFs were delivered using AAVs described herein via retro-orbital delivery. 2.5e12 viral genomes (vg) per animal was used and the animals were sacrificed ten weeks later. Microarray analysis was performed on the hippocampal tissue from the treated mice, where the data shown is in comparison to an irrelevant ZFP-TF delivered the same way. FIG. 17 shows that tau was specifically repressed by the 57890V and 52389V proteins as compared to treatment with a GFP encoding AAV. These data demonstrate that the specificity of these proteins observed in vitro is also found in vivo.

Example 10: Tau Reduction in Mouse Model of AD

Studies were performed in a mouse model of AD in addition to those done above in wild type mice. APP/PS1 mice (reviewed in Li et al., ibid) were treated with the ZFP-TFs as described herein to analyze efficacy in this model.

In brief, in one experiment, 4 APP/PS1 mice and 2 wild type controls were treated at 4.5 months of age. Single injections were performed introducing 3 μL of AAV composition into the opposite cortices (CTX) of the brain. The left CTX of each mouse received 3 μL of AAV9 comprising the ZFP-TF linked to GFP driven by the SynapsinI promoter (either an irrelevant ZFP-TF control ("172"; AAV9 syn1-172v)) or the 52389 ZFP-TF ("389"; AAV9 syn1-389v). The right CTX of each mouse received 3 μL of AAV9 comprising a RFP expression construct driven by the SynapsinI promoter ("AAV9 syn1-tRFP").

Figure 15:
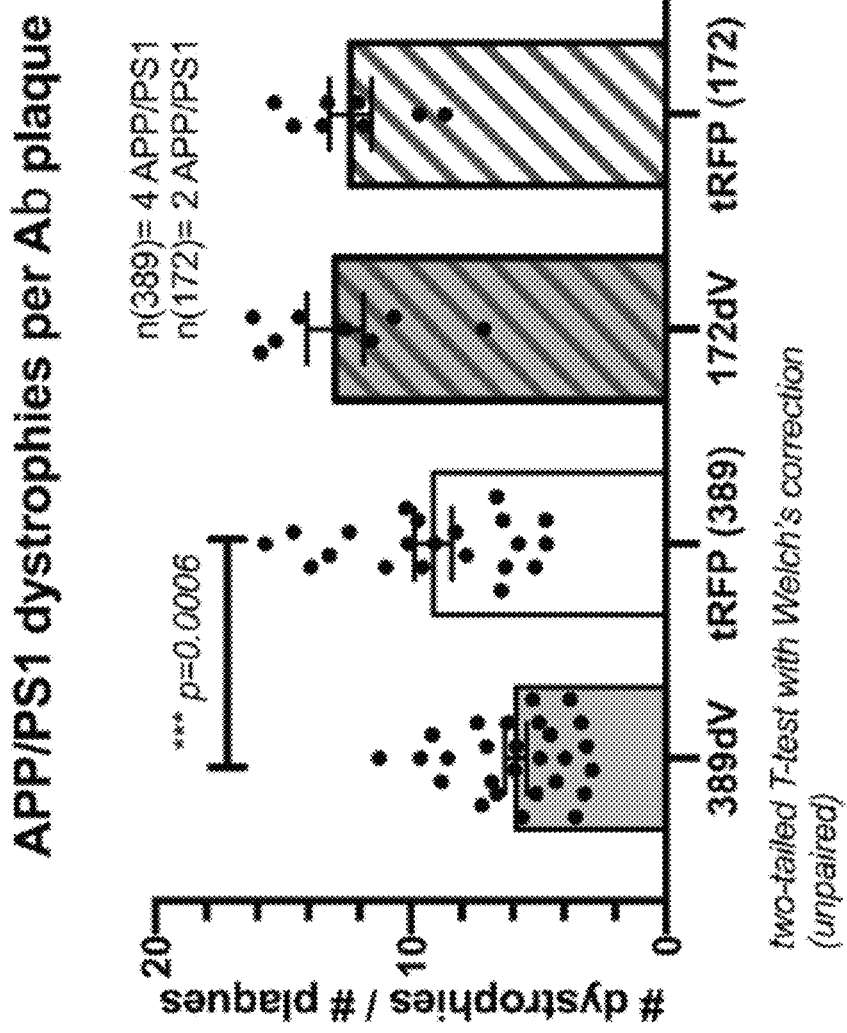
FIG. 15 is a graph showing a quantitative representation of the number of dystrophic neurites per Aβ plaque in the APP/PS1 mice. Each dot represents the average number of dystrophic neurites per plaque for all plaques in one cortical section; 3-5 sections were analyzed per hemisphere per mouse. As can be seen, there was a statistically significant reduction in dystrophic neurites in the CTX treated with the 389dV ZFP-TF as compared to the CTX treated with the tRFP (left-most (gray) bar is 389dV treated, second from left (white) bar is tRFP treated). Also shown is a comparison of the CTX in mice treated with the irrelevant ZFP-TF ("172dV", gray striped bar, $2^{nd}$ from right bar) or tRFP (white striped bar, right-most bar). As can be seen, there was no difference in the number of dystrophic neurites/plaque between these samples.
Figure 16:
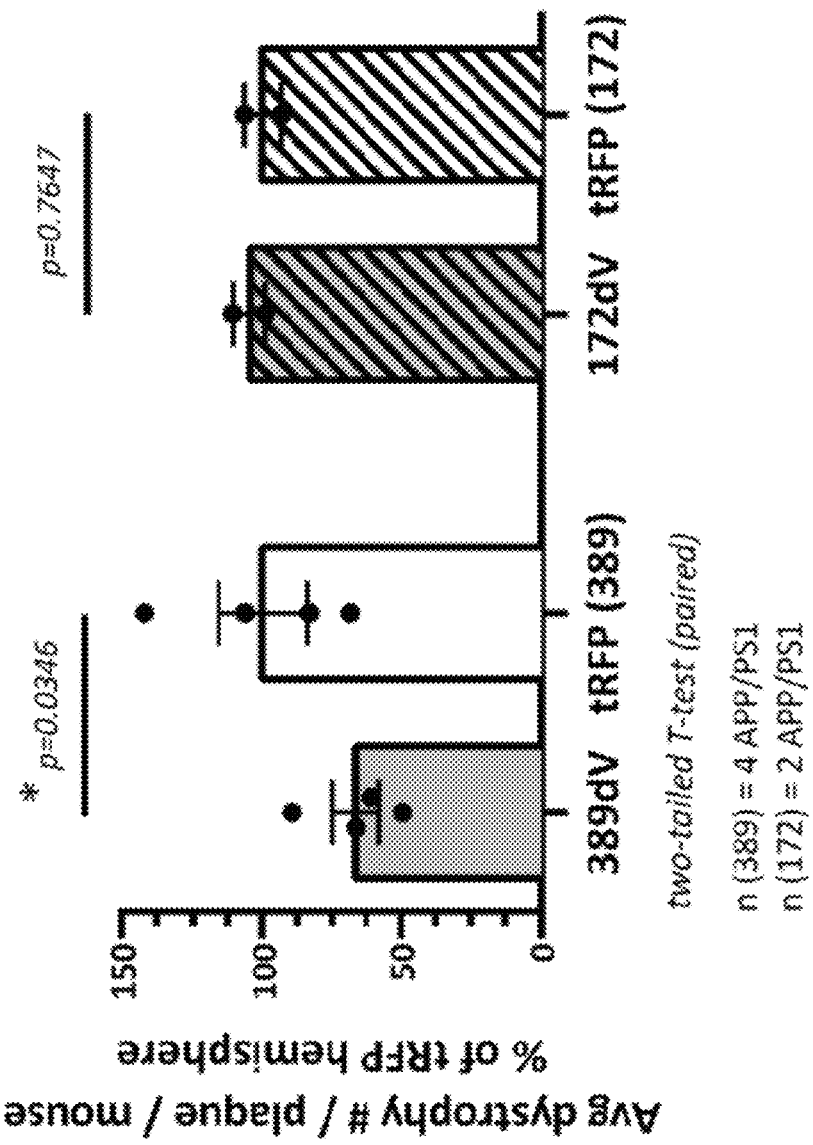
FIG. 16 is a graph depicting a quantitative comparison of the data represented in FIG. 15 accounting for the variation amongst animals in baseline dystrophic neurites per plaque. The number of dystrophies per Aβ plaque were averaged for each ZFP-TF treated hemisphere or the contralateral tRFP-treated hemisphere and compared using a paired two-tailed T-test. The values for each cohort were scaled to the mean of the tRFP-treated side (set to 100%). Using this paired analysis, dystrophic neurites were found to be significantly reduced (mean 34% reduction) for the 52389V-treated cohort (left most (gray) bar is 389dV treated, second from left (white) bar is tRFP treated), but not for the cohort treated with an irrelevant ZFP-TF (172dV, second from right (gray striped) bar; tRFP, right most (white striped) bar).

Eleven (11) weeks following treatment, the 7-month old mice were perfused with 4% PFA/PBS. The whole brains were then removed and post-fixed for 2 days with 4% PFA/PBS at 4° C. The tissue was then cryoprotected in a 30% sucrose/PBS solution. 50 μm coronal sections were analyzed for immunofluorescent labeling for tRFP, GFP, and amyloid beta ("Aβ"). 3 brain sections were analyzed per mouse and 3-5 images of each section were taken. Dystrophic neurites were counted in the Aβ-rich plaques such that between 121 and 256 plaques were analyzed per animal. 708 plaques were counted for the AAV9 syn1-389v treated CTX, and 287 were counted for the AAV9 syn1-tRFP CTX. Exemplary data are presented in FIGS. 14A-D, and showed a statistically significant difference in the number of dystrophic neurites per numbers of Aβ plaques in the cortices treated with the 52389 ZFP-TF as compared to the tRFP treated cortices (FIGS. 15 and 16). In contrast, there was no difference in dystrophies per plaque in the animals treated with the irrelevant ZFP-TF. In addition, the number and volume of plaques was unchanged in both treated and untreated animals. Further experiments performed using other AAV vectors, modes of administration and/or ZFP-TFs as described herein produced similar results.

Thus, the tau genetic repressors described herein provide clinical and therapeutic benefit for tauopathies such as AD, as shown by studies in known mouse models of AD.

Example 11: Tau Reduction In Vivo in a Primate Brain

Primate tau-specific ZFP-TFs are tested in cynomolgus monkeys (*M. fascicularis*) to observe repression of tau expression in a primate (non-human primate (NHP) model). Cynomolgus monkeys are housed in stainless steel cages equipped with a stainless mesh floor and an automatic watering valve. The study complies with all applicable sections of the Final Rules of the Animal Welfare Act regulations (Code of Federal Regulations, Title 9).

Initial experiments are conducted to determine if the hippocampus of the monkeys can be adequately targeted. Control article (Formulation Buffer, PBS and 0.001% Pluronic F-68, pH 7.1) and test article are thawed and dispensed on Day 1 of the studies where test and control articles are administered via MM-guided delivery of AAV9-GFP or AAV9-ZFP-TFs to the hippocampus.

In the first experiment, AAV9 comprising a hSYN1 driven GFP gene are delivered at 3.84 e11 vg/hemisphere to the left hemisphere and 7.68 e11 vg/hemisphere to the right hemisphere. One animal receives a single dose of test article in a volume of 40 μL in the left and a single dose of 80 μL in the right. A second animal receives two doses of 20 μL in the left, and two doses of 40 μL in the right hemisphere. For both test articles, the dose concentration is 9.6e12 vg/mL. After 14 days, the animals are sacrificed and the brains are hemisected and divided into approximately 17 slices (3 mm each). Slices comprising the hippocampal/entorhinal cortex regions are used to analyze the intrinsic GFP fluorescence and GFP immunohistochemistry. Other slices are used to collect tissue punches for mRNA analysis via qRT-PCR, where levels of tau and housekeeping genes are analyzed. Additionally, some punches are collected and retained for exploratory tau protein analysis. The results show that the hSYN1 promoter is able to drive GFP expression which is detectable in the hippocampal region following delivery.

A second experiment is performed to evaluate the effect of the route of administration on GFP expression and location in the brain. In this study, the GFP transgene is carried by an SB3 AAV particle (see U.S. Provisional application No. 62/503,121), and the dose concentration of the test article is 2.5e13 vg/mL. The dose is administered by intracerebroventricular, intrathecal or intravenous routes, where the dose volume (mL/animal) is approximately 1, 1.5 and 10-16, respectively. 14 days following dosing, the animals are sacrificed and the brains are hemisected as described above. In addition to analyzing the levels of tau and housekeeping genes by qRT-PCR, genes associated with inflammation (GFAP and Iba1) are also analyzed. Exploratory studies are also performed to analyze the levels of tau protein in the brain tissue samples and in the cerebrospinal fluid. These studies show that the dosing routes are all well tolerated and are able to deliver the GFP transgene to the hippocampal region.

Subsequently, a study is performed to analyze the repression of tau expression by artificial transcription factors as described herein in the cynomolgus brain. Three or more ZFP-TFs as described herein (Tables 1 through 3) are tested, where the three ZFPs have been characterized as proteins that have high specificity (0 off targets) and high (>90% repression) in vitro efficacy (ZFP-TF 1); moderate specificity (5-10 off targets) and high in vitro efficacy (ZFP-TF2); and high specificity and moderate (50-60%) in vitro efficacy (ZFP-TF3). The animals are sacrificed at 1, 3 and 6-month time points and analyzed as described above. Significant repression of tau throughout the brain and CSF is observed with no significant neuronal loss.

The studies demonstrate that the tau ZFP-TF reagents repress tau expression (including at therapeutic levels) in a primate brain.

All patents, patent applications and publications mentioned herein are hereby incorporated by reference for all purposes in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A genetic modulator of a human or mouse microtubule associated protein tau (MAPT) gene, the modulator comprising:

A zinc finger protein (ZFP) DNA-binding domain that binds to a target site of at least 12 nucleotides within the MAPT gene, wherein the ZFP DNA-binding domain comprises four, five or six zinc finger domains, each zinc finger domain comprising a recognition helix region, and wherein the ZFP DNA-binding domain comprises the recognition helix regions ordered as F1 to F4, F1 to F5, or F1 to F6 shown in a single row of the table below, wherein the SEQ ID NO of each sequence is indicated in parenthesis:

| F1 | F2 | F3 | F4 | F5 | F6 |
|---|---|---|---|---|---|
| RSDNLAR (7) | DRSHLAR (8) | QSGNLAR (9) | QSNTRIM (10) | | |
| ERGTLAR (11) | TSANLSR (12) | TSGNLTR (13) | HRTSLTD (14) | RSHSLLR (15) | HPSARKR (16) |
| RSANLTR (17) | DSSHLEL (18) | DRSNLTR (19) | DRSHLTR (20) | DRSHLAR (8) | |
| DRSHLTR (20) | LKQHLTR (37) | RSAHLSR (25) | TSGHLSR (26) | QSGNLAR (9) | QSGDLTR (35) |
| RSAHLSR (25) | TSGHLSR (26) | QSGNLAR (9) | QSGDLTR (35) | DRSHLSR (38) | DRSHLAR (8) |
| RSDNLSE (21) | TSSNRKT (22) | TSGNLTR (13) | DRSALAR (23) | RNSDRTK (24) | |
| DSSHLEL (18) | DRSNLTR (19) | DRSHLTR (20) | DRSHLAR (8) | RSAHLSR (25) | TSGHLSR (26) |
| LRHHLTR (27) | RRFTLSK (28) | RSDVLSE (29) | KHSTRRV (30) | RSDVLSE (29) | RLYTLHK (47) |
| RSADLTR (34) | QSGDLTR (35) | RSDHLSE (36) | RSAHLSR (25) | | | and a transcriptional regulatory domain or a nuclease domain.

2. The genetic modulator of claim 1, wherein the transcriptional regulatory domain comprises a repression domain.

3. A polynucleotide encoding the genetic modulator according to claim 1.

4. A gene delivery vehicle comprising the polynucleotide according to claim 3.

5. The gene delivery vehicle of claim 4, wherein the gene delivery vehicle comprises an AAV vector.

6. A pharmaceutical composition comprising one or more polynucleotides according to claim 3.

7. The pharmaceutical composition of claim 6, wherein the genetic modulator comprises a nuclease domain and cleaves the MAPT gene.

8. The pharmaceutical composition of claim 7, further comprising a donor nucleic acid molecule that is integrated into the cleaved MAPT gene.

9. An isolated cell comprising the genetic modulator according to claim 1.

10. An isolated cell comprising the polynucleotide according to claim 3.

11. A kit comprising one or more of gene delivery vehicles according to claim 5 and instructions for use.

12. The genetic modulator of claim 1, wherein the ZFP DNA-binding domain comprises the F1 to F4, F1 to F5, or F1 to F6 recognition helix regions, and the phosphate contact mutations, if present, of the ZFP designated 52288, 52322, 52366, 57890, 57880, 65888, 52364, 52389, 65894, 57930, 65918, 65920, 65887, 57947, 65968, or 65860.

13. The genetic modulator of claim 1, wherein the ZFP DNA-binding domain comprises RSADLTR (SEQ ID NO:34), QSGDLTR (SEQ ID NO:35), RSDHLSE (SEQ ID NO:36), and RSAHLSR (SEQ ID NO:25) for F1 to F4, respectively.

14. The genetic modulator of claim 1, wherein the ZFP DNA-binding domain comprises RSANLTR (SEQ ID NO:17), DSSHLEL (SEQ ID NO:18), DRSNLTR (SEQ ID NO:19), DRSHLTR (SEQ ID NO:20), and DRSHLAR (SEQ ID NO:8) for F1 to F5, respectively.

15. The genetic modulator of claim 1, wherein the ZFP DNA-binding domain comprises RSDNLSE (SEQ ID NO:21), TSSNRKT (SEQ ID NO:22), TSGNLTR (SEQ ID NO:13), DRSALAR (SEQ ID NO:23), and RNSDRTK (SEQ ID NO:24) for F1 to F5, respectively.

16. The genetic modulator of claim 1, wherein the ZFP DNA-binding domain comprises LRHHLTR (SEQ ID NO:27), RRFTLSK (SEQ ID NO:28), RSDVLSE (SEQ ID NO:29), KHSTRRV (SEQ ID NO:30), RSDVLSE (SEQ ID NO:29), and RLYTLHK (SEQ ID NO:47) for F1 to F6, respectively.

17. The genetic modulator of claim 1, wherein the ZFP DNA-binding domain comprises DSSHLEL (SEQ ID NO:18), DRSNLTR (SEQ ID NO:19), DRSHLTR (SEQ ID NO:20), DRSHLAR (SEQ ID NO:8), RSAHLSR (SEQ ID NO:25), and TSGHLSR (SEQ ID NO:26) for F1 to F6, respectively.

18. The genetic modulator of claim 1, wherein the ZFP DNA-binding domain comprises DSSHLEL (SEQ ID NO:18), DRSNLTR (SEQ ID NO:19), DRSHLTR (SEQ ID NO:20), DRSHLAR (SEQ ID NO:8), RSAHLSR (SEQ ID NO:25), and TSGHLSR (SEQ ID NO:26) for F1 to F6, respectively, and a Qm5 mutation in the backbone region of F1, F3, and F5.

19. The genetic modulator of claim 1, wherein the ZFP DNA-binding domain comprises RSDNLAR (SEQ ID NO:7), DRSHLAR (SEQ ID NO:8), QSGNLAR (SEQ ID NO:9), and QSNTRIM (SEQ ID NO:10) for F1 to F4, respectively.

20. The genetic modulator of claim 1, wherein the ZFP DNA-binding domain comprises ERGTLAR (SEQ ID NO:11), TSANLSR (SEQ ID NO:12), TSGNLTR (SEQ ID NO:13), HRTSLTD (SEQ ID NO:14), RSHSLLR (SEQ ID NO:15), and HPSARKR (SEQ ID NO:16) for F1 to F6, respectively.

21. The genetic modulator of claim 1, wherein the ZFP DNA-binding domain comprises LRHHLTR (SEQ ID NO:27), RRFTLSK (SEQ ID NO:28), RSDVLSE (SEQ ID NO:29), KHSTRRV (SEQ ID NO:30), RSDVLSE (SEQ ID NO:29), RLYTLHK (SEQ ID NO:47) for F1 to F6, respectively, and a Qm5 mutation in the backbone region of F1 and F5.

22. The genetic modulator of claim 1, wherein the ZFP DNA-binding domain comprises DRSHLTR (SEQ ID NO:20), LKQHLTR (SEQ ID NO:37), RSAHLSR (SEQ ID NO:25), TSGHLSR (SEQ ID NO:26), QSGNLAR (SEQ ID NO:9), and QSGDLTR (SEQ ID NO:35) for F1 to F6, respectively.

23. The genetic modulator of claim 1, wherein the ZFP DNA-binding domain comprises DRSHLTR (SEQ ID NO:20), LKQHLTR (SEQ ID NO:37), RSAHLSR (SEQ ID NO:25), TSGHLSR (SEQ ID NO:26), QSGNLAR (SEQ ID NO:9), and QSGDLTR (SEQ ID NO:35) for F1 to F6, respectively, and a Qm5 mutation in the backbone region of F1 and F5.

24. The genetic modulator of claim 1, wherein the ZFP DNA-binding domain comprises DRSHLTR (SEQ ID NO:20), LKQHLTR (SEQ ID NO:37), RSAHLSR (SEQ ID NO:25), TSGHLSR (SEQ ID NO:26), QSGNLAR (SEQ ID NO:9), and QSGDLTR (SEQ ID NO:35) for F1 to F6, respectively, and a Qm5 mutation in the backbone region of F1, F3, and F5.

25. The genetic modulator of claim 1, wherein the ZFP DNA-binding domain comprises DSSHLEL (SEQ ID NO:18), DRSNLTR (SEQ ID NO:19), DRSHLTR (SEQ ID NO:20), DRSHLAR (SEQ ID NO:8), RSAHLSR (SEQ ID NO:25), and TSGHLSR (SEQ ID NO:26) for F1 to F6, respectively, and a Qm5 mutation in the backbone region of F3 and F5.

26. The genetic modulator of claim 1, wherein the ZFP DNA-binding domain comprises RSAHLSR (SEQ ID NO:25), TSGHLSR (SEQ ID NO:26), QSGNLAR (SEQ ID NO:9), QSGDLTR (SEQ ID NO:35), DRSHLSR (SEQ ID NO:38), and DRSHLAR (SEQ ID NO:8) for F1 to F6, respectively.

27. The genetic modulator of claim 1, wherein the ZFP DNA-binding domain comprises RSAHLSR (SEQ ID NO:25), TSGHLSR (SEQ ID NO:26), QSGNLAR (SEQ ID NO:9), QSGDLTR (SEQ ID NO:35), DRSHLSR (SEQ ID NO:38), and DRSHLAR (SEQ ID NO:8) for F1 to F6, respectively, and a Qm5 mutation in the backbone region of F1, F3, and F5.

28. The genetic modulator of claim 1, wherein the ZFP DNA-binding domain comprises ERGTLAR (SEQ ID NO:11), TSANLSR (SEQ ID NO:12), TSGNLTR (SEQ ID NO:13), HRTSLTD (SEQ ID NO:14), RSHSLLR (SEQ ID NO:15), and HPSARKR (SEQ ID NO:16) for F1 to F6, respectively, and a Qm5 mutation in the backbone region of F5.

29. The genetic modulator of claim 2, wherein the transcriptional regulatory domain comprises a KRAB domain.

30. The genetic modulator of claim 1, wherein the ZFP DNA-binding domain binds to a target site within a human MAPT gene.

31. The gene delivery vehicle of claim 5, wherein the AAV vector is an AAV2/9 vector.

* * * * *

SEQUENCE LISTING

```
<160> NUMBER OF SEQ ID NOS: 51

<210> SEQ ID NO 1
<211> LENGTH: 28
<212> TYPE: DNA
<213> ORGANISM: Mouse sp.

<400> SEQUENCE: 1
cgacagaagg cgaggacaga agaggaca                                          28

<210> SEQ ID NO 2
<211> LENGTH: 28
<212> TYPE: DNA
<213> ORGANISM: Mouse sp.

<400> SEQUENCE: 2
ccgttgcgcc tgattgatgc ccagctcc                                          28

<210> SEQ ID NO 3
<211> LENGTH: 28
<212> TYPE: DNA
<213> ORGANISM: Mouse sp.

<400> SEQUENCE: 3
gtggcggaga ctgagagcgc gcgcggcc                                          28

<210> SEQ ID NO 4
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 4
cttctgtcga ttatcaggta agcgccgc                                          28

<210> SEQ ID NO 5
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 5
ctggtgggtg gcggagactg agagcgcg                                          28

<210> SEQ ID NO 6
<211> LENGTH: 28
<212> TYPE: DNA
<213> ORGANISM: Unknown
<220> FEATURE:
<223> OTHER INFORMATION: Description of Unknown:
      Human or mouse oligonucleotide
```

```
<400> SEQUENCE: 6
tggtgctgga gctggtgggt ggcggaga                                         28

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Asn Leu Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser His Leu Ala Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Gly Asn Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Asn Thr Arg Ile Met
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Gly Thr Leu Ala Arg
1               5

<210> SEQ ID NO 12
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Thr Ser Ala Asn Leu Ser Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ser Gly Asn Leu Thr Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Arg Thr Ser Leu Thr Asp
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser His Ser Leu Leu Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Pro Ser Ala Arg Lys Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Ala Asn Leu Thr Arg
1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ser Ser His Leu Glu Leu
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Asn Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Arg Ser His Leu Thr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Asn Leu Ser Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Ser Ser Asn Arg Lys Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Asp Arg Ser Ala Leu Ala Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Asn Ser Asp Arg Thr Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Ala His Leu Ser Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ser Gly His Leu Ser Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Arg His His Leu Thr Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Phe Thr Leu Ser Lys
1               5

<210> SEQ ID NO 29
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Val Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys His Ser Thr Arg Arg Val
1               5

<210> SEQ ID NO 31
<211> LENGTH: 19
<212> TYPE: DNA
<213> ORGANISM: Homo sapiens

<400> SEQUENCE: 31
gcagtcaccg ccacccacc                                                    19

<210> SEQ ID NO 32
<211> LENGTH: 19
<212> TYPE: DNA
<213> ORGANISM: Mus sp.

<400> SEQUENCE: 32
tcagtctccg ccacccacc                                                    19

<210> SEQ ID NO 33
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 33
aggggcgggc agcgaggcct gggcgggc                                          28

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Ala Asp Leu Thr Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Gln Ser Gly Asp Leu Thr Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp His Leu Ser Glu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Lys Gln His Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Ser His Leu Ser Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Arg Ser Asn Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Arg Gln Asn Leu Ile Met
1               5

<210> SEQ ID NO 41
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ser Ala Asn Leu Thr Val
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Asp His Leu Ser Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Arg Asn Asp Arg Lys Ser
1               5

<210> SEQ ID NO 44
<211> LENGTH: 28
<212> TYPE: DNA
<213> ORGANISM: Mouse sp.

<400> SEQUENCE: 44
cggcagaagg tgggcggtgg cggcggcg                                          28

<210> SEQ ID NO 45
<211> LENGTH: 28
<212> TYPE: DNA
<213> ORGANISM: Mouse sp.

<400> SEQUENCE: 45
gcggcggcgg cagaaggtgg gcggtggc                                          28

<210> SEQ ID NO 46
<211> LENGTH: 28
<212> TYPE: DNA
<213> ORGANISM: Unknown
<220> FEATURE:
<223> OTHER INFORMATION: Description of Unknown:
      Human or mouse oligonucleotide

<400> SEQUENCE: 46
ctccagaagg ggatcatgac ctcctcac                                          28

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 47

Arg Leu Tyr Thr Leu His Lys
1               5

<210> SEQ ID NO 48
<211> LENGTH: 18
<212> TYPE: DNA
<213> ORGANISM: Homo sapiens

<400> SEQUENCE: 48
acccaccagc tccggcac                                                   18

<210> SEQ ID NO 49
<211> LENGTH: 18
<212> TYPE: DNA
<213> ORGANISM: Mus sp.

<400> SEQUENCE: 49
acccaccagc tccagcac                                                   18

<210> SEQ ID NO 50
<211> LENGTH: 15
<212> TYPE: DNA
<213> ORGANISM: Homo sapiens

<400> SEQUENCE: 50
tctgtcgact atcag                                                      15

<210> SEQ ID NO 51
<211> LENGTH: 15
<212> TYPE: DNA
<213> ORGANISM: Mus sp.

<400> SEQUENCE: 51
tctgtcgatt atcag                                                      15
```